United States Patent [19]

Barriere et al.

[11] Patent Number: 4,668,669

[45] Date of Patent: May 26, 1987

[54] PRISTINAMYCIN II$_B$ DERIVATIVES AND COMPOSITIONS CONTAINING THEM

[75] Inventors: Jean-Claude Barriere, Massy; Claude Cotrel, Paris; Jean-Marc Paris, Vaires sur Marne, all of France

[73] Assignee: Rhone-Poulenc Sante, Courbevoie, France

[21] Appl. No.: 817,548

[22] Filed: Jan. 10, 1986

[30] Foreign Application Priority Data

Jan. 11, 1985 [FR] France .................... 85 00377

[51] Int. Cl.$^4$ .................... A61K 31/42; C07D 498/14; C07K 5/12
[52] U.S. Cl. .................... 514/183; 530/317; 540/455
[58] Field of Search ............ 260/239.3 T; 514/183; 540/455; 530/317

[56] References Cited

U.S. PATENT DOCUMENTS 4,590,004  5/1986  Corbet et al. .................... 530/317

OTHER PUBLICATIONS

Chemical Abstracts, vol. 101, 1984; p. 726, Ref. No. 191457r.
Bulletin Soc. Chimique de France, No. 2, 1968, pp. 585–591.
The Journal of Antibiotics, vol. XXXVII, No. 10, Oct. 1984, pp. 1246–1252.
Chemical Abstract, vol. 100, 1984, p. 564, Ref. No. 209476n.
Noller, "Chemistry of Organic Compounds", 2nd Ed., (Saunders) (1957) pp. 283–286.

Primary Examiner—Robert T. Bond
Attorney, Agent, or Firm—Stevens, Davis, Miller & Mosher

[57] ABSTRACT

Pristinamycin II$_B$ derivatives of formula:

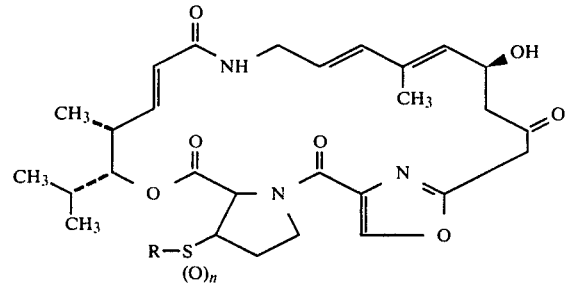

in which R denotes a nitrogen-containing 4 to 7-membered heterocyclic ring optionally substituted by alkyl; or alkyl (2 to 4 C) substituted by 1 or 2 phenyl, cycloalkylamino or N-alkyl-N-cycloalkylamino (3 to 6 ring atoms), alkylamino, dialkylamino or dialkylcarbamoyloxy radicals (the dialkylamino moieties of these 2 latter radicals being capable of forming a 4 to 7-membered cyclic ring optionally substituted by alkyl) or substituted by 1 or 2 nitrogen-containing 4 to 7 membered heterocyclic rings, optionally substituted by alkyl, at least one of the above substituents being a nitrogen-containing substituent capable of forming salts and n is 1 or 2, all the alkyls being linear or branched and containing (unless stated otherwise) 1 to 10 carbon atoms, their isomers, their salts and their preparation. These compounds, optionally in combination with known synergistins or synergistins of formula:

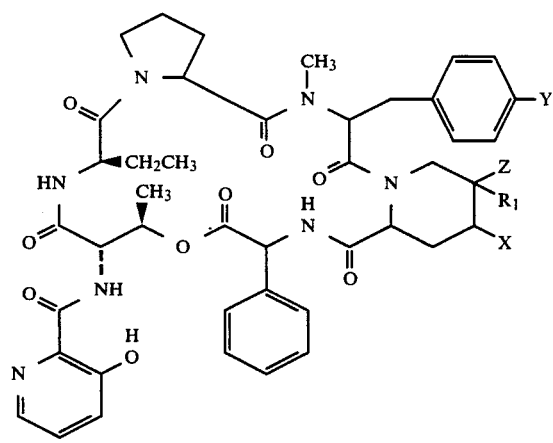

are useful as antimicrobial agents.

10 Claims, No Drawings

PRISTINAMYCIN II$_B$ DERIVATIVES AND COMPOSITIONS CONTAINING THEM

This invention relates to pristinamycin II$_B$ derivatives their preparation, and compositions containing them.

The present invention provides new pristinamycin II$_B$ derivatives, of the formula:

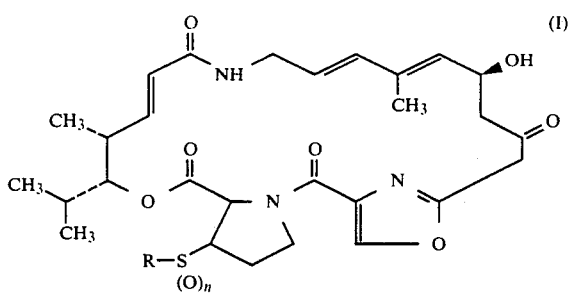

and their acid addition salts, in which R denotes: either a nitrogen-containing 4 to 7-membered heterocyclic ring radical, which may contain 1 or more other hetero atoms chosen from nitrogen, oxygen and sulphur in the form of sulphoxide or sulphone, and unsubstituted or substituted by alkyl; or alkyl of 2 to 4 carbon atoms substituted by 1 or 2 radicals chosen from phenyl, cycloalkylamino of 3 to 6 ring atoms, N-alkyl-N-cycloalkylamino of 3 to 6 ring atoms, alkylamino, dialkylamino and dialkylcarbamoyloxy, the alkyl parts of these 2 latter radicals being unjoined or joined to form, with the nitrogen atom to which they are attached, a saturated or unsaturated 4 to 7-membered heterocyclic ring which may contain another hetero atom chosen from nitrogen, oxygen and sulphur in the form of sulphoxide or sulphone, and unsubstituted or substituted by alkyl, or alkyl of 2 to 4 carbon atoms substituted by one or more nitrogen-containing, 4 to 7-membered heterocyclic rings which may contain 1 or 2 other hetero atoms chosen from nitrogen, oxygen and sulphur in the form of sulphoxide or sulphone, and unsubstituted or substituted by alkyl, these heterocyclic rings being linked to the alkyl by a carbon atom of the ring, at least one of the substituents carried by the said alkyl chain being a nitrogen-containing substituent capable of forming salts, and n is 1 or 2. The alkyl radicals and moieties referred to above are linear or branched and, unless mentioned otherwise, contain 1 to 10 carbon atoms.

The products of formula (I) have isomeric forms and their isomers and their mixtures are included within the scope of the present invention.

When R denotes a heterocyclic radical, this radical can be, for example: 3-azetidinyl, 3-pyrrolidinyl, 3- or 4-piperidyl or 3- or 4-azepinyl.

When R denotes an alkyl radical substituted by a heterocyclic ring radical, the heterocyclic ring radical can be chosen, for example, from the radicals listed above or the 2-azetidinyl, 2-pyrrolidinyl, 2-piperidyl, 2-azepinyl, piperazinyl, 4-alkylpiperazinyl, quinolyl, isoquinolyl or imidazolyl radicals.

When R contains a dialkylamino or dialkylcarbamoyloxy radical in which the alkyl moieties form a heterocyclic ring with the nitrogen atom to which they are attached, this ring can be chosen, for example, from: 1-azetidinyl, 1-pyrrolidinyl, piperidino, 1-azepinyl, morpholino, thiomorpholino in the form of sulphoxide or sulphone, 1-piperazinyl, 4-alkyl-1-piperazinyl, N-alkyl-1-homopiperazinyl, or 1-imidazolyl.

The following compounds of general formula (I) can be mentioned, in particular, by way of example:
26-(3-azetidinyl)sulphinylpristinamycin II$_B$
26-(1-methyl-3-azetidinyl)sulphinylpristinamycin II$_B$
26-(1-ethyl-3-azetidinyl)sulphinylpristinamycin II$_B$
26-(1-isopropyl-3-azetidinyl)sulphinylpristinamycin II$_B$
26-(3-pyrrolidinyl)sulphinylpristinamycin II$_B$
26-(1-methyl-3-pyrrolidinyl)sulphinylpristinamycin II$_B$
26-(1-ethyl-3-pyrrolidinyl)sulphinylpristinamycin II$_B$
26-(1-isopropyl-3-pyrrolidinyl)sulphinylpristinamycin II
26-(3-piperidyl)sulphinylpristinamycin II$_B$
26-(1-methyl-3-piperidyl)sulphinylpristinamycin II$_B$
26-(1-ethyl-3-piperidyl)sulphinylpristinamycin II$_B$
26-(4-piperidyl)sulphinylpristinamycin II$_B$
26-(1-methyl-4-piperidyl)sulphinylpristinamycin II$_B$
26-(1-ethyl-4-piperidyl)sulphinylpristinamycin II$_B$
26-(3-azepinyl)sulphinylpristinamycin II$_B$
26-(4-azepinyl)sulphinylpristinamycin II$_B$
26-(2-cyclopropylaminoethyl)sulphinylpristinamycin II$_B$
26-(2-cyclobutylaminoethyl)sulphinylpristinamycin II$_B$
26-(2-cyclopentylaminoethyl)sulphinylpristinamycin II$_B$
26-(2-cyclohexylaminoethyl)sulphinylpristinamycin II$_B$
26-(N-cyclohexyl-N-methyl-2-aminoethyl)sulphinylpristinamycin II$_B$
26-(2-methylaminoethyl)sulphinylpristinamycin II$_B$
26-(2-ethylaminoethyl)sulphinylpristinamycin II$_B$
26-(2-propylaminoethyl)sulphinylpristinamycin II$_B$
26-(2-isopropylaminoethyl)sulphinylpristinamycin II$_B$
26-(2-butylaminoethyl)sulphinylpristinamycin II$_B$
26-(2-isobutylaminoethyl)sulphinylpristinamycin II$_B$
26-(2-n-decylaminoethyl)sulphinylpristinamycin II$_B$
26-(dimethylaminoethyl)sulphinylpristinamycin II$_B$
26-(2-diethylaminoethyl)sulphinylpristinamycin II$_B$
26-(2-dipropylaminoethyl)sulphinylpristinamycin II$_B$
26-(2-diisopropylaminoethyl)sulphinylpristinamycin II$_B$
26-(2-dibutylaminoethyl)sulphinylpristinamycin II$_B$
26-(2-diisobutylaminoethyl)sulphinylpristinamycin II$_B$
26-(N-ethyl-N-methyl-2-aminoethyl)sulphinylpristinamycin II$_B$
26-[2-(1-azetidinyl)ethyl]sulphinylpristinamycin II$_B$
26-[2-(1-pyrrolidinyl)ethyl]sulphinylpristinamycin II$_B$
26-(2-piperidinoethyl)sulphinylpristinamycin II$_B$
26-[2-(1-azepinyl)ethyl]sulphinylpristinamycin II$_B$
26-(2-morpholinoethyl)sulphinylpristinamycin II$_B$
26-[2-(1-piperazinyl)ethyl]sulphinylpristinamycin II$_B$
26-[2-(4-methyl-1-piperazinyl)ethyl]sulphinylpristinamycin II$_B$
26-[2-(4-methyl-1-homopiperazinyl)ethyl]sulphinylpristinamycin II$_B$
26-[2-(1-imidazolyl)ethyl]sulphinylpristinamycin II$_B$
26-(2-dimethylaminocarbamoyloxyethyl)sulphinylpristinamycin II$_B$
26-(2-diethylaminocarbamoyloxyethyl)sulphinylpristinamycin II$_B$
26-(2-diisopropylaminocarbamoyloxyethyl)sulphinylpristinamycin II$_B$ 26-[2-(4-methyl-1-piperazinyl)carbamoyloxyethyl]sulphinylpristinamycin II$_B$
26-[2-(2-azetidinyl)ethyl]sulphinylpristinamycin II$_B$
26-[2-(3-azetidinyl)ethyl]sulphinylpristinamycin II$_B$
26-[2-(2-pyrrolidinyl)ethyl]sulphinylpristinamycin II$_B$
26-[2-(3-pyrrolidinyl)ethyl]sulphinylpristinamycin II$_B$
26-[2-(2-piperidyl)ethyl]sulphinylpristinamycin II$_B$
26-[2-(3-piperidyl)ethyl]sulphinylpristinamycin II$_B$
26-[2-(4-piperidyl)ethyl]sulphinylpristinamycin II$_B$
26-[2-(2-azepinyl)ethyl]sulphinylpristinamycin II$_B$
26-[2-(3-azepinyl)ethyl]sulphinylpristinamycin II$_B$
26-[2-(4-azepinyl)ethyl]sulphinylpristinamycin II$_B$
26-[2-(3-quinolyl)ethyl]sulphinylpristinamycin II$_B$
26-[2-(4-quinolyl)ethyl]sulphinylpristinamycin II$_B$
26-[2-(1,2,3,4-tetrahydro-2-isoquinolyl)ethyl]sulphinylpristinamycin II$_B$
26-82-(1-isoquinolyl)ethyl]sulphinylpristinamycin II$_B$
26-(2-imidazolylethyl)sulphinylpristinamycin II$_B$
26-(2-cyclopropylamino-1-methylethyl)sulphinylpristinamycin II$_B$
26-(2-cyclobutylamino-1-methylethyl)sulphinylpristinamycin II$_B$
26-(2-cyclopentylamino-1-methylethyl)sulphinylpristinamycin II$_B$
26-(cyclohexylamino-1-methylethyl)sulphinylpristinamycin II$_B$
26-[2-(N-cyclohexyl-N-methyl-amino)-1-methylethyl]sulphinylpristinamycin II$_B$
26-(2-methylamino-1-methylethyl)sulphinylpristinamycin II$_B$
26-(2-ethylamino-1-methylethyl)sulphinylpristinamycin II$_B$
26-(1-methyl-2-propylaminoethyl)sulphinylpristinamycin II$_B$
26-(2-isopropylamino-1-methylethyl)sulphinylpristinamycin II$_B$
26-(2-butylamino-1-methylethyl)sulphinylpristinamycin II$_B$
26-(2-isobutylamino-1-methylethyl)sulphinylpristinamycin II$_B$
26-(1-methyl-2-n-decylaminoethyl)sulphinylpristinamycin II$_B$
26-(2-dimethylamino-1-methylethyl)sulphinylpristinamycin II$_B$
26-(2-diethylamino-1-methylethyl)sulphinylpristinamycin II$_B$
26-(2-dipropylamino-1-methylethyl)sulphinylpristinamycin II$_B$
26-(2-diisopropylamino-1-methylethyl)sulphinylpristinamycin II$_B$
26-(2-dibutylamino-1-methylethyl)sulphinylpristinamycin II$_B$
26-(2-diisobutylamino-1-methylethyl)sulphinylpristinamycin II$_B$
26-[2-(N-ethyl-N-methyl-amino)-1-methylethyl]sulphinylpristinamycin II$_B$
26-[2-(1-azetidinyl)-1-methylethyl]sulphinylpristinamycin II$_B$
26-[1-methyl-2-(1-pyrrolidinyl)ethyl]sulphinylpristinamycin II$_B$
26-(1-methyl-2-piperidinoethyl)sulphinylpristinamycin II$_B$
26-[2-(1-azepinyl)-1-methylethyl]sulphinylpristinamycin II$_B$
26-(1-methyl-2-morpholinoethyl)sulphinylpristinamycin II$_B$
26-[1-methyl-2-(1-piperazinyl)ethyl]sulphinylpristinamycin II$_B$
26-[2-(4-methyl-1-piperazinyl)-1-methylethyl]sulphinylpristinamycin II$_B$
26-[2-(4-methyl-1-homopiperazinyl)-1-methylethyl]sulphinylpristinamycin II$_B$
26-[2-(1-imidazolyl)-1-methylethyl]sulphinylpristinamycin II$_B$ 26-(2-dimethylaminocarbamoyloxy-1-methylethyl)sulphinylpristinamycin II$_B$
26-(2-diethylaminocarbamoyloxy-1-methylethyl)sulphinylpristinamycin II$_B$
26-(2-diisopropylaminocarbamoyloxy-1-methylethyl)-sulphinylpristinamycin II$_B$
26-[2-(4-methyl-1-piperazinyl)carbamoyloxy-1-methylethyl]sulphinylpristinamycin II$_B$
26-[2-(2-azetidinyl)-1-methylethyl]sulphinylpristinamycin II$_B$
26-[2-(3-azetidinyl)-1-methylethyl]sulphinylpristinamycin II$_B$
26-[1-methyl-2-(2-pyrrolidinyl)ethyl]sulphinylpristinamycin II$_B$
26-[1-methyl-2-(3-pyrrolidinyl)ethyl]sulphinylpristinamycin II$_B$
26-[1-methyl-2-(2-piperidyl)ethyl]sulphinylpristinamycin II$_B$
26-[1-methyl-2-(3-piperidyl)ethyl]sulphinylpristinamycin II$_B$
26-[1-methyl-2-(4-piperidyl)ethyl]sulphinylpristinamycin II$_B$
26-[2-(2-azepinyl)-1-methylethyl]sulphinylpristinamycin II$_B$
26-[2-(3-azepinyl)-1-methylethyl]sulphinylpristinamycin II$_B$
26-[2-(4-azepinyl)-1-methylethyl]sulphinylpristinamycin II$_B$
26-[1-methyl-2-(3-quinolyl)ethyl]sulphinylpristinamycin II$_B$
26-[1-methyl-2-(4-quinolyl)ethyl]sulphinylpristinamycin II$_B$
26-[1-methyl-2-(1,2,3,4-tetrahydro-2-isoquinolyl)ethyl]-sulphinylpristinamycin II$_B$
26-[2-(1-isoquinolyl)-1-methylethyl]sulphinylpristinamycin II$_B$
26-(2-imidazolyl-1-methylethyl)sulphinylpristinamycin IIB
26-(2-cyclopropylamino-2-methylethyl)sulphinylpristinamycin II$_B$
26-(2-cyclobutylamino-2-methylethyl)sulphinylpristinamycin II$_B$
26-(2-cyclopentylamino-2-methylethyl)sulphinylpristinamycin II$_B$
26-(2-cyclohexylamino-2-methylethyl)sulphinylpristinamycin II$_B$
26-[2-(N-cyclohexyl-N-methylamino)-2-methylethyl]-sulphinylpristinamycin II$_B$
26-(2-methylamino-2-methylethyl)sulphinylpristinamycin II$_B$
26-(2-ethylamino-2-methylethyl)sulphinylpristinamycin II$_B$ 26-(2-methyl-2-propylaminoethyl)sulphinylpristinamycin II$_B$
26-(2-isopropylamino-2-methylethyl)sulphinylpristinamycin II$_B$
26-(2-butylamino-2-methylethyl)sulphinylpristinamycin II$_B$
26-(2-isobutylamino-2-methylethyl)sulphinylpristinamycin II$_B$
26-(2-methyl-2-n-decylaminoethyl)sulphinylpristinamycin II$_B$
26-(2-dimethylamino-2-methylethyl)sulphinylpristinamycin II$_B$
26-(2-diethylamino-2-methylethyl)sulphinylpristinamycin II$_B$
26-(2-dipropylamino-2-methylethyl)sulphinylpristinamycin II$_B$
26-(2-diisopropylamino-2-methylethyl)sulphinylpristinamycin II$_B$
26-(2-dibutylamino-2-methylethyl)sulphinylpristinamycin II$_B$
26-(2-diisobutylamino-2-methylethyl)sulphinylpristinamycin II$_B$
26-[2-(N-ethyl-N-methyl-amino)-2-methylethyl]sulfinylpristinamycin II$_B$
26-[2-(1-azetidinyl)-2-methylethyl]sulphinylpristinamycin II$_B$
26-[2-methyl-2-(1-pyrrolidinyl)ethyl]sulphinylpristinamycin II$_B$
26-(2-methyl-2-piperidinoethyl)sulphinylpristinamycin IIB
26-[2-(1-azepinyl)-2-methylethyl]sulphinylpristinamycin II$_B$
26-(2-methyl-2-morpholinoethyl)sulphinylpristinamycin II$_B$
26-[2-methyl-2-(1-piperazinyl)ethyl]sulphinylpristinamycin II$_B$
26-[2-(4-methyl)-1-piperazinyl)-2-methylethyl]sulphinylpristinamycin II$_B$
26-[2-(4-methyl-1-homopiperazinyl)-2-methylethyl]sulphinylpristinamycin II$_B$
26-[2-(1-imidazolyl)-2-methylethyl]sulphinylpristinamycin II$_B$
26-(2-dimethylaminocarbamoyloxy-2-methylethyl)sulphinylpristinamycin II$_B$
26-(2-diethylaminocarbamoyloxy-2-methylethyl)sulphinylpristinamycin II$_B$
26-(2-diisopropylaminocarbamoyloxy-2-methylethyl)sulphinylpristinamycin II$_B$
26-[2-(4-methyl-1-piperazinyl)carbamoyloxy-2-methylethyl]sulphinylpristinamycin II$_B$
26-[2-(2-azetidinyl)-2-methylethyl]sulphinylpristinamycin II$_B$
26-[2-(3-azetidinyl)-2-methylethyl]sulphinylpristinamycin II$_B$
26-[2-methyl-2-(2-pyrrolidinyl)ethyl]sulphinylpristinamycin II$_B$
26-[2-methyl-2-(3-pyrrolidinyl)ethyl]sulphinylpristinamycin II$_B$
26-[2-methyl-2-(2-piperidyl)ethyl]sulphinylpristinamycin II$_B$
26-[2-methyl-2-(3-piperidyl)ethyl]sulphinylpristinamycin II$_B$
26-[2-methyl-2-(4-piperidyl)ethyl]sulphinylpristinamycin II$_B$
26-[2-(2-azepinyl)-2-methylethyl]sulphinylpristinamycin II$_B$
26-[2-(3-azepinyl)-2-methylethyl]sulphinylpristinamycin II$_B$
26-[2-(4-azepinyl)-2-methylethyl]sulphinylpristinamycin II$_B$
26-[2-methyl-2-(3-quinolyl)ethyl]sulphinylpristinamycin II$_B$
26-[2-methyl-2-(4-quinolyl)ethyl]sulphinylpristinamycin II$_B$
26-[2-methyl-2-(1,2,3,4-tetrahydro-2-isoquinolyl)ethyl]sulphinylpristinamycin II$_B$
26-[2-(1-isoquinolyl)-2-methylethyl]sulphinylpristinamycin II$_B$
26-(imidazolyl-2-methylethyl)sulphinylpristinamycin II$_B$
26-(2-dimethylamino-3-phenylpropyl)sulphinylpristinainamycin II$_B$
26-(2-dimethylaminobutyl)sulphinylpristinamycin II$_B$
26-(3-azetidinyl)sulphonylpristinamycin II$_B$
26-(1-methyl-3-azetidinyl)sulphonylpristinamycin II$_B$
26-(1-ethyl-3-azetidinyl)sulphonylpristinamycin II$_B$
26-(1-isopropyl-3-azetidinyl)sulphonylpristinamycin II$_B$
26-(3-pyrrolidinyl)sulphonylpristinamycin II$_B$
26-(1-methyl-3-pyrrolidinyl)sulphonylpristinamycin II$_B$
26-(1-ethyl-3-pyrrolidinyl)sulphonylpristinamycin II$_B$
26-(1-isopropyl-3-pyrrolidinyl)sulphonylpristinamycin II$_B$
26-(3-piperidyl)sulphonylpristinamycin II$_B$
26-(1-methyl-3-piperidyl)sulphonylpristinamycin II$_B$
26(1-ethyl-3-piperidyl)sulphonylpristinamycin II$_B$
26-(4-piperidyl)sulphonylpristinamycin II$_B$
26-(1-methyl-4-piperidyl)sulphonylpristinamycin II$_B$
26-(1-ethyl-4-piperidyl)sulphonylpristinamycin II$_B$
26-(3-azepinyl)sulphonylpristinamycin II$_B$
26-(4-azepinyl)sulphonylpristinamycin II$_B$
26-(2-cyclopropylaminoethyl)sulphonylpristinamycin II$_B$
26-(2-cyclobutylaminoethyl)sulphonylpristinamycin II$_B$
26-(2-cyclopentylaminoethyl)sulphonylpristinamycin II$_B$
26-(2-cyclohexylaminoethyl)sulphonylpristinamycin II$_B$
26-(N-cyclohexyl-N-methyl-2-aminoethyl)sulphonylpristinamycin II$_B$
26-(2-methylaminoethyl)sulphonylpristinamycin II$_B$
26-(2-ethylaminoethyl)sulphonylpristinamycin II$_B$
26-(2-propylaminoethyl)sulphonylpristinamycin II$_B$
26-(2-isopropylaminoethyl)sulphonylpristinamycin II$_B$
26-(2-butylaminoethyl)sulphonylpristinamycin II$_B$
26-(2-isobutylaminoethyl)sulphonylpristinamycin II$_B$
26-(2-n-decylaminoethyl)sulphonylpristinamycin II$_B$
26-(2-dimethylaminoethyl)sulphonylpristinamycin II$_B$
26-(2-diethylaminoethyl)sulphonylpristinamycin II$_B$
26-(2-dipropylaminoethyl)sulphonylpristinamycin II$_B$
26-(2-diisopropylaminoethyl)sulphonylpristinamycin II$_B$
26-(2-dibutylaminoethyl)sulphonylpristinamycin II$_B$
26-(2-diisobutylaminoethyl)sulphonylpristinamycin II$_B$
26-(N-ethyl-N-methyl-2-aminoethyl)sulphonylpristinamycin II$_B$ 26-[2-(1-azetidinyl)ethyl]sulphonylpristinamycin $II_B$
26-[2-(1-pyrrolidinyl)ethyl]sulphonylpristinamycin $II_B$
26-(2-piperidinoethyl)sulphonylpristinamycin $II_B$
26-[2-(1-azepinyl)ethyl]sulphonylpristinamycin $II_B$
26-(2-morpholinoethyl)sulphonylpristinamycin $II_B$
26-[2-(1-piperazinyl)ethyl]sulphonylpristinamycin $II_B$
26-[2-(4-methyl-1-piperazinyl)ethyl]sulphonylpristinamycin $II_B$
26-[2-(4-methyl-1-homopiperazinyl)ethyl]sulphonylpristinamycin $II_B$
26-[2-(1-imidazolyl)ethyl]sulphonylpristinamycin $II_B$
26-(2-dimethylaminocarbamoyloxyethyl)sulphonylpristinamycin $II_B$
26-(2-diethylaminocarbamoyloxyethyl)sulphonylpristinamycin $II_B$
26-(2-diisopropylaminocarbamoyloxyethyl)sulphonylpristinamycin $II_B$
26-[2-(4-methyl-1-piperazinyl)carbamoyloxyethyl]sulphonylpristinamycin $II_B$
26-[2-(2-azetidinyl)ethyl]sulphonylpristinamycin $II_B$
26-[2-(3-azetidinyl)ethyl]sulphonylpristinamycin $II_B$
26-[2-(2-pyrrolidinyl)ethyl]sulphonylpristinamycin $II_B$
26-[2-(3-pyrrolidinyl)ethyl]sulphonylpristinamycin $II_B$
26-[2-(2-piperidyl)ethyl]sulphonylpristinamycin $II_B$
26-[2-(3-piperidyl)ethyl]sulphonylpristinamycin $II_B$
26-[2-(4-piperidyl)ethyl]sulphonylpristinamycin $II_B$
26-[2-(2-azepinyl)ethyl]sulphonylpristinamycin $II_B$
26-[2-(3-azepinyl)ethyl]sulphonylpristinamycin $II_B$
26-[2-(4-azepinyl)ethyl]sulphonylpristinamycin $II_B$
26-[2-(3-quinolyl)ethyl]sulphonylpristinamycin $II_B$
26-[2-(4-quinolyl)ethyl]sulphonylpristinamycin $II_B$
26-[2-(1,2,3,4-tetrahydro-2-isoquinolyl)ethyl]sulphonylpristinamycin $II_B$
26-[2-(1-isoquinolyl)ethyl]sulphonylpristinamycin $II_B$
26-(2-imidazolylethyl)sulphonylpristinamycin $II_B$
26-(2-cyclopropylamino-1-methylethyl)sulphonylpristinamycin $II_B$
26-(2-cyclobutylamino-1-methylethyl)sulphonylpristinamycin $II_B$
26-(2-cyclopentylamino-1-methylethyl)sulphonylpristinamycin $II_B$
26-(2-cyclohexylamino-1-methylethyl)sulphonylpristinamycin $II_B$
26-[2-(N-cyclohexyl-N-methylamino)-1-methylethyl)-sulphonylpristinamycin $II_B$
26-(2-methylamino-1-methylethyl)sulphonylpristinamycin $II_B$
26-(2-ethylamino-1-methylethyl)sulphonylpristinamycin $II_B$
26-(1-methyl-2-propylaminoethyl)sulphonylpristinamycin $II_B$
26-(2-isopropylamino-1-methylethyl)sulphonylpristinamycin $II_B$
26-(2-butylamino-1-methylethyl)sulphonylpristinamycin $II_B$
26-(2-isobutylamino-1-methylethyl)sulphonylpristinamycin $II_B$
26-(1-methyl-2-n-decylaminoethyl)sulphonylpristinamycin $II_B$
26-(2-dimethylamino-1-methylethyl)sulphonylpristinamycin $II_B$
26-(2-diethylamino-1-methylethyl)sulphonylpristinamycin $II_B$
26-(2-dipropylamino-1-methylethyl)sulphonylpristinamycin $II_B$
26-(2-diisopropylamino-1-methylethyl)sulphonylpristinamycin $II_B$
26-(2-dibutylamino-1-methylethyl)sulphonylpristinamycin $II_B$
26-(2-diisobutylamino-1-methylethyl)sulphonylpristinamycin $II_B$
26-[2-(N-ethyl-N-methyl-amino)-1-methylethyl[sulphonylpristinamycin $II_B$
26-[2-81-(azetidinyl)-1-methylethyl]sulphonylpristinamycin $II_B$
26-[1-methyl-2-(1-pyrrolidinyl)ethyl]sulphonylpristinamycin $II_B$
26-(1-methyl-2-piperidinoethyl)sulphonylpristinamycin $II_B$
26-[2-(1-azepinyl)-1-methylethyl]sulphonylpristinamycin $II_B$
26-(1-methyl-2-morpholinoethyl)sulphonylpristinamycin $II_B$
26-[1-methyl-2-(1-piperazinyl)ethyl]sulphonylpristinamycin $II_B$
26-[2-(4-methyl-1-piperazinyl)-1-methylethyl]sulphonylpristinamycin $II_B$
26-[2-(4-methyl-1-homopiperazinyl)-1-methylethyl]sulphonylpristinamycin $II_B$
26-[2-(1-imidazolyl)-1-methylethyl]sulphonylpristinamycin $II_B$
26-(2-dimethylaminocarbamoyloxy-1-methylethyl)sulphonylpristinamycin $II_B$
26-(2-diethylaminocarbamoyloxy)-1-methylethyl)-sulphonylpristinamycin $II_B$
26-(2-diisopropylaminocarbamoyloxy-1-methylethyl)-sulphonylpristinamycin $II_B$
26-[2-(4-methyl-1-piperazinyl)carbamoyloxy-1-methylethyl]sulphonylpristinamycin $II_B$
26-[2-(2-azetidinyl)-1-methylethyl]sulphonylpristinamycin $II_B$
26-[2-(3-azetidinyl)-1-methylethyl]sulphonylpristinamycin $II_B$
26-[1-methyl-2-(2-pyrrolidinyl)ethyl]sulphonylpristinamycin $II_B$
26-[1-methyl-2-(3-pyrrolidinyl)ethyl]sulphonylpristinamycin $II_B$
26-[1-methyl-2-(2-piperidyl)ethyl]sulphonylpristinamycin $II_B$
26-[1-methyl-2-(3-piperidyl)ethyl]sulphonylpristinamycin $II_B$
26-[1-methyl-2-(4-piperidyl)ethyl]sulphonylpristinamycin $II_B$
26-[2-(2-azepinyl)-1-methylethyl]sulphonylpristinamycin $II_B$
26-[2-(3-azepinyl)-1-methylethyl]sulphonylpristinamycin $II_B$
26-[2-(4-azepinyl)-1-methylethyl]sulphonylpristinamycin $II_B$
26-[1-methyl-2-(3-quinolyl)ethyl]sulphonylpristinamycin $II_B$
26-[1-methyl-2-[4-quinolyl)ethyl]sulphonylpristinamycin $II_B$
26-[1-methyl-2-(1,2,3,4-tetrahydro-2-isoquinolyl)ethyl]-sulphonylpristinamycin $II_B$ 26-[2-(1-isoquinolyl)-1-methylethyl]sulphonylpristinamycin II$_B$
26-(2-imidazolyl-1-methylethyl)sulphonylpristinamycin II$_B$
26-(2-cyclopropylamino-2-methylethyl)sulphonylpristinamycin II$_B$
26-(2-cyclobutylamino-2-methylethyl)sulphonylpristinamycin II$_B$
26-(2-cyclopentylamino-2-methylethyl)sulphonylpristinamycin II$_B$
26-(2-cyclohexylamino-2-methylethyl)sulphonylpristinamycin II$_B$
26-[2-(N-cyclohexyl-N-methyl-amino)-2-methylethyl]sulphonylpristinamycin II$_B$
26-(2-methylamino-2-methylethyl)sulphonylpristinamycin II$_B$
26-(2-ethylamino-2-methylethyl)sulphonylpristinamycin II$_B$
26-(2-methyl-2-propylaminoethyl)sulphonylpristinamycin II$_B$
26-(2-isopropylamino-2-methylethyl)sulphonylpristinamycin II$_B$
26-(2-butylamino-2-methylethyl)sulphonylpristinamycin II$_B$
26-(2-isobutylamino-2-methylethyl)sulphonylpristinamycin II$_B$
26-(2-methyl-2-n-decylaminoethyl)sulphonylpristinamycin II$_B$
26-(2-dimethylamino-2-methylethyl)sulphonylpristinamycin II$_B$
26-(2-diethylamino-2-methylethyl)sulphonylpristinamycin II$_B$
26-(2-dipropylamino-2-methylethyl)sulphonylpristinamycin II$_B$
26-(2-diisopropylamino-2-methylethyl)sulphonylpristinamycin II$_B$
26-(2-dibutylamino-2-methylethyl)sulphonylpristinamycin II$_B$
26-(2-diisobutylamino-2-methylethyl)sulphonylpristinamycin II$_B$
26-[2-(N-ethyl-N-methyl-amino)-2-methylethyl]sulphonylpristinamycin II$_B$
26-[2-(1-azetidinyl)-2-methylethyl]sulphonylpristinamycin II$_B$
26-[2-methyl-2-(1-pyrrolidinyl)ethyl]sulphonylpristinamycin II$_B$
26-(2-methyl-2-piperidinoethyl)sulphonylpristinamycin II$_B$
26-[2-(1-azepinyl)-2-methylethyl]sulphonylpristinamycin II$_B$
26-(2-methyl-2-morpholinoethyl)sulphonylpristinamycin II$_B$
26-[2-methyl-2-(1-piperazinyl)ethyl]sulphonylpristinamycin II$_B$
26-[2-(4-methyl-1-piperazinyl)-2-methylethyl]sulphonylpristinamycin II$_B$
26-[2-(4-methyl-1-homopiperazinyl)-2-methylethyl]sulphonylpristinamycin II$_B$
26-[2-(1-imidazolyl)-2-methylethyl]sulphonylpristinamycin II$_B$
26-(2-dimethylaminocarbamoyloxy-2-methylethyl)sulphonylpristinamycin II$_B$
26-(2-diethylaminocarbamoyloxy-2-methylethyl)sulphonylpristinamycin II$_B$
26-(2-diisopropylaminocarbamoyloxy-2-methylethyl)sulphonylpristinamycin II$_B$
26-[2-(4-methyl-1-piperazinyl)carbamoyloxy-2-methylethyl]sulphonylpristinamycin II$_B$
26-[2-(2-azetidinyl)-2-methylethyl)sulphonylpristinamycin II$_B$
26-[2-(3-azetidinyl)-2-methylethyl]sulphonylpristinamycin II$_B$
26-[2-methyl-2-(2-pyrrolidinyl)ethyl]sulphonylpristinamycin II$_B$
26-[2-methyl-2-(3-pyrrolidinyl)ethyl]sulphonylpristinamycin II$_B$
26-[2-methyl-2-(2-piperidyl)ethyl]sulphonylpristinamycin II$_B$
26-[2-methyl-2-(3-piperidyl)ethyl]sulphonylpristinamycin II$_B$
26-[2-methyl-2-(4-piperidyl)ethyl]sulphonylpristinamycin II$_B$
26-[2-(2-azepinyl)-2-methylethyl]sulphonylpristinamycin II$_B$
26-[2-(3-azepinyl)-2-methylethyl]sulphonylpristinamycin II$_B$
26-[2-(4-azepinyl)-2-methylethyl]sulphonylpristinamycin II$_B$
26-[2-methyl-2-(3-quinolyl)ethyl]sulphonylpristinamycin II$_B$
26-[2-methyl-2-(4-quinolyl)ethyl]sulphonylpristinamycin II$_B$
26-[2-methyl-2-(1,2,3,4-tetrahydro-2-isoquinolyl)ethyl]sulphonylpristinamycin II$_B$
26-[2-(1-isoquinolyl)-2-methylethyl]sulphonylpristinamycin II$_B$
26-(2-imidazolyl-2-methylethyl)sulphonylpristinamycin II$_B$
26-(2-dimethylamino-3-phenylpropyl)sulphonylpristinamycin II$_B$
26-(2-dimethylaminobutyl)sulphonylpristinamycin II$_B$ According to the invention, the products of general formula (I) can be prepared by oxidation of a derivative of pristinamycin II$_B$, of its salt or of a protected derivative, of general formula:

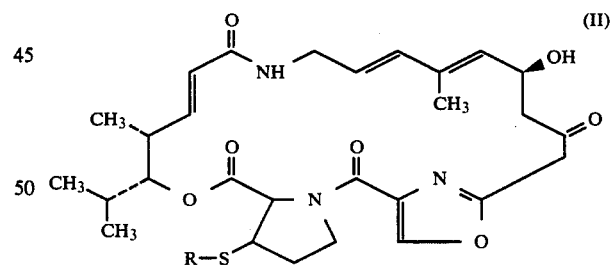

(II)

in which R is defined as above, it being understood that in the cases where R contains a sulphur-containing hetero cyclic ring, the sulphur atom can be in the form of a sulphide, sulphoxide or sulphone.

The reaction is generally carried out by means of an oxidizing agent, optionally prepared in situ, in an aqueous medium or in an organic solvent, preferably a chlorinated solvent (methylene chloride, 1,2-dichloroethane or chloroform, for example) or an alcohol (methanol or tert-butanol, for example) or a mixture of these solvents. Optionally the operation can be carried out under nitrogen.

Among the oxidizing agents which are suitable for preparing a product of general formula (I) in which n=1, it is possible to mention organic peracids: percarboxylic or persulphonic acids (for example peracetic, pertrifluoroacetic, performic, perbenzoic, m-chloroperbenzoic, p-nitroperbenzoic, permaleic, monoperphthalic, percamphoric or p-toluenepersulphonic acids) or inorganic peracids (for example periodic or persulphuric acid).

When the intention is to prepare a product of general formula (I) in which n=2, the operation is advantageously carried out in the presence of selenium dioxide and hydrogen peroxide, using the salt of the product of general formula (II), or in the presence of a peracid such as those referred to above, especially pertrifluoroacetic acid, or m-chloroperbenzoic acid.

When the derivative of pristinamycin $II_B$ of general formula (II) is used in the form of a salt, use is made of the salts formed with organic or inorganic acids, preferably with trifluoroacetic, tartaric, acetic, benzoic, or hydrochloric acids.

When the product of general formula (II) is used in the form of a salt or of a protected derivative, the reaction is advantageously carried out at a temperature between $-40°$ and $50°$ C.

When it is intended to prepare a product of general formula (I) in which n=1, it is also advantageous to operate by starting from the derivative of pristinamycin $II_B$ of general formula (II) in the presence of an alkali metal bicarbonate (for example sodium bicarbonate) at a temperature between $-60°$ and $-40°$ C.

When R contains an alkylamino or cycloalkylamino substituent, it is also possible to utilize a protected derivative of the product of general formula (II). The latter can be protected by any amine-protective group whose introduction and removal do not affect the remainder of the molecule; use is advantageously made of the trifluoroacetyl group which can be removed after the reaction by treatment with an alkali metal bicarbonate (sodium or potassium bicarbonate) in an aqueous solution.

The products of general formula (II) can be prepared by the reaction of a product of general formula:

R—H    (III)

in which R is defined as above, with the product of formula:

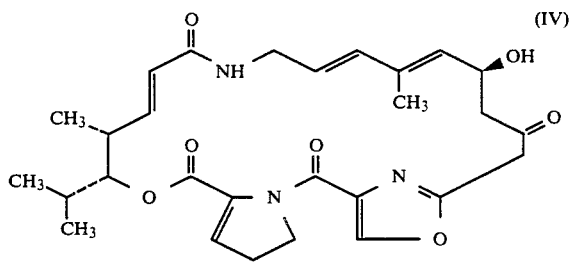

that is to say pristinamycin $II_A$.

The reaction is usually carried out in an organic solvent such as an alcohol such as methanol or ethanol, or a chlorinated solvent such as methylene chloride, 1,2-dichloroethane or chloroform, or in a mixture of these solvents (for example methylene chloride/methanol) at a temperature between $-30°$ and $50°$ C.

Occasionally it may be advantageous to operate in the presence of a tertiary amine, for example triethylamine, or of an ethanolamine (for example dimethylethanolamine), A person skilled in the art will understand that, when R denotes a radical containing a secondary amine group capable of interfering with the reaction, this group will need to be protected beforehand, before the product of general formula (III) is reacted with the product of formula (IV). Any usual means which enables a secondary amine function to be blocked in the form of a labile radical can be used for this purpose. It is especially advantageous to use the trifluoroacetyl radical as a blocking radical which can be removed as described above. In such a case, however, it is not absolutely essential to remove the protective radical, and the protected derivative can be used directly in the oxidation reaction.

According to the invention, the products of general formula (I) in which n is equal to 2 can also be prepared by the oxidation of a product of general formula (I) in which n is equal to 1.

The reaction is carried out under conditions which are similar to the conditions described above for preparing a product of general formula (I) in which n=2 starting from a pristinamycin $II_B$ derivative of general formula (II).

The new products of general formula (I) can be purified by known methods, for example by crystallization, chromatography or successive extractions in an acidic or basic medium. For the person skilled in the art who is aware of the sensitivity of synergistins in an alkaline medium, a "basic medium" is understood to mean a medium which is just alkaline enough to liberate the parent substance from its salt of addition with an acid, that is to say a medium whose pH does not exceed 8.

It is well known that the synergistins obtained by fermentation constitute products which are greatly sought after by medical practitioners for the treatment of many complaints due to Gram-positive bacteria (of the Staphylococci, Streptococci, pneumococci or enterococci type) and Gram-negative bacteria (of the Haemophilus, gonococci, meningococci type). However, these products have the disadvantage of being insoluble in an aqueous medium and consequently can be administered only by oral route, generally in the form of gelatine capsules, coated pills or tablets. In view of this insolubility, it has hitherto been impossible to use the known synergistins when the patient is unable to swallow; this is the case, in particular, in paediatrics and in reanimation, while the activity spectrum of these products would render them a valuable indication in many circumstances, for example in cases of comatose septicaemias.

The new products according to the invention have the considerable advantage of being capable of being dissolved in water, usually in the form of salts, in usable therapeutic doses, and of enhancing, via a synergism phenomenon, the antibacterial action of pristinamycin $I_A$, virginiamycin S or of derivatives of soluble synergistins of general formula:

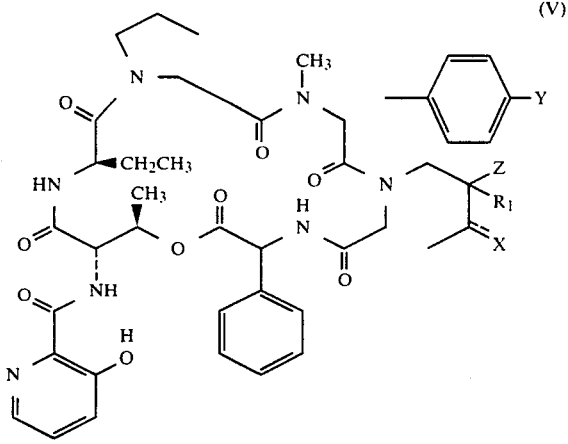

(V)

in which Y denotes a hydrogen atom or a dimethylamino radical and (1) either $===$ denotes a single bond, Z and $R_1$ denote a hydrogen atom and X denotes a radical of general formula:

(VI)

in which:
either $R_2$ denotes a hydrogen atom and $R_3$ denotes a hydroxy or alkyl radical optionally substituted by a carboxy, alkyloxycarbonyl, hydroxy, alkylamino or dialkylamino radical whose alkyl radicals can form, with the nitrogen atom to which they are attached, a 4 to 7-membered hetero-cyclic ring chosen from azetidinyl, pyrrolidinyl, piperidinyl, piperazinyl, N-alkylpiperazinyl or azepinyl rings, or $R_3$ denotes a cycloalkyl radical containing 3 to 7 carbon atoms or a saturated 4 to 7-membered heterocyclic ring chosen from the azetidine, pyrrolidine, piperidine and azepine rings, these heterocyclic rings being optionally capable of being substituted by an alkyl radical on the nitrogen atom, or $R_2$ denotes a formyl or alkylcarbonyl radical and $R_3$ denotes an alkyl radical substituted by a carboxy, alkylamino or dialkylamino radical whose alkyl radicals can form, with the nitrogen atom to which they are attached a 4, to 7-membered heterocyclic ring chosen from azetidinyl, pyrrolidinyl, piperidinyl, piperazinyl, N-alkylpiperazinyl or azepinyl ring, or $R_3$ denotes a 4 to 7-membered heterocyclic ring chosen from the azetidine, pyrrolidine, piperidine and azepine rings, these heterocyclic rings being capable of being substituted by an alkyl radical on the nitrogen atom, or $R_2$ and $R_3$, which are identical or different, denote an alkyl radical optionally substituted by a carboxy, alkyloxycarbonyl, hydroxy, alkylamino or dialkylamino radical whose alkyl radicals optionally form, with the nitrogen atom to which they are attached, a 4 to 7-membered heterocyclic ring chosen from azetidinyl, pyrrolidinyl, piperidinyl, piperazinyl, N-alkylpiperazinyl or azepinyl or $R_2$ and $R_3$ form, together with the nitrogen atom to which they are attached, a 4 to 7-membered heterocyclic ring chosen from the azetidine, pyrrolidine, piperidine, morpholine and piperazine rings, optionally substituted by an alkyl radical, (2) or $===$ denotes a double bond, X denotes an oxygen atom and Z denotes a radical of general formula:

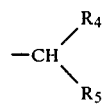

(VII)

defined as follows:
(a) either $R_1$ and $R_5$ each denote a hydrogen atom and $R_4$ denotes a 3-pyrrolidinylthio or 3- or 4-piperidylthio radical (these radicals being optionally substituted by an alkyl radical) or $R_4$ denotes an alkylthio radical substituted by one or two hydroxysulphonyl, alkylamino, or dialkylamino (optionally substituted by a mercapto or dialkylamino radical) radicals, or by one or two rings chosen from piperazino (optionally substituted by an alkyl or mercaptoalkyl radical) morpholino, thiomorpholino, piperidino, 1-pyrrolidinyl, 2-, 3- or 4-piperidyl and 2- or 3-pyrrolidinyl radicals (the latter two rings being optionally substituted by an alkyl radical on the nitrogen atom), (b) or $R_1$ and $R_5$ together form a valency bond and $R_4$ denotes a 3-pyrrolidinylamino, 3- or 4-piperidylamino, 3-pyrrolidinyloxy, 3- or 4-piperidyloxy, 3-pyrrolidinylthio or 3- or 4-piperidylthio radical (these radicals being optionally substituted by an alkyl radical on the nitrogen atom in the ring), or $R_4$ denotes an alkylamino, alkyloxy or alkylthio radical substituted by one or two hydroxysulphonyl, alkylamino, dialkylamino (optionally substituted by a dialkylamino radical), trialkylammonio or 4- or 5-imidazolyl radicals or by one or two rings chosen from piperazino (optionally substituted by an alkyl or mercapto alkyl radical), morpholino, thiomorpholino, piperidino, 1-pyrrolidinyl, 2-, 3- or 4-piperidinyl and 2- or 3-pyrrolidinyl radical (the last two rings being optionally substituted by an alkyl radical on the nitrogen atom), it being understood that the alkyl radicals and alkyl moieties referring to the symbols of the general formula (V) contain 1 to 5 carbon atoms and form a linear or branched chain.

Some of the derivatives of synergistins of general formula (V) can have isomeric forms. It is to be understood that these isomeric forms as well as their mixtures can be advantageously associated with the products of general formula (I).

The products of general formula (V) defined as above under (1), with the exception of those in which $R_2$ denotes a formyl or alkylcarbonyl radical, can be prepared by the action of an amine of general formula:

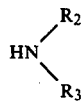

(VIII)

in which $R_2$ and $R_3$ are defined as above, on a synergistin of general formula:

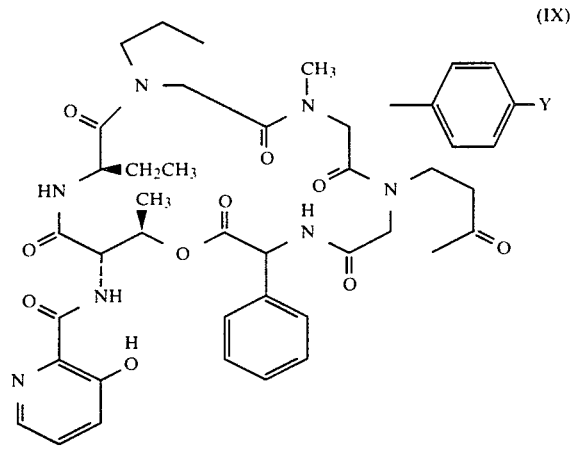 (IX)

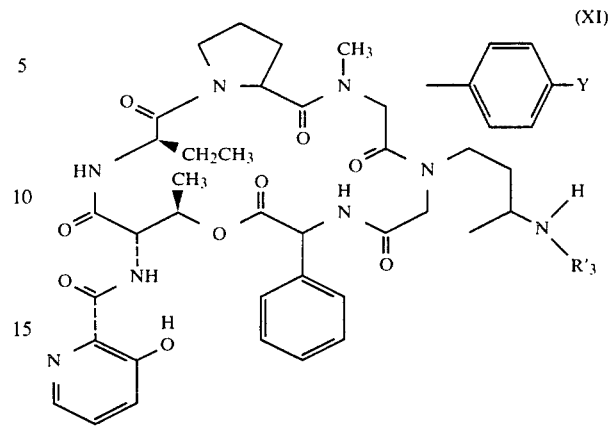 (XI)

in which Y denotes a hydrogen atom (virginiamycin S) or the dimethylamino radical (pristinamycin I$_A$), in the presence of an alkali metal cyanoborohydride.

The operation is generally carried out with an excess of amine of general formula (VIII) in the presence of an alkali metal cyanoborohydride such as sodium cyanoborohydride, in an organic solvent such as an alcohol containing dissolved gaseous hydrogen chloride (methanolic hydrogen chloride or ethanolic hydrogen chloride) at a temperature between 0° C. and the reflux temperature of the reaction mixture, preferably at a temperature in the region of 20° C.

The reaction can be advantageously carried out in the presence of a drying agent such as molecular sieves.

The products of general formula (V) defined as above under (1) in which R$^2$ denotes a formyl or alkylcarbonyl radical and R$_3$ denotes an alkyl radical substituted by a carboxy, alkylamino or dialkylamino radical whose alkyl radicals optionally form, with the nitrogen atom to which they are attached, a 4 to 7-membered heterocyclic ring chosen from azetidinyl, pyrrolidinyl, piperidinyl, piperazinyl, alkyl-piperazinyl or azepinyl ring, or denotes a saturated 4 to 7-membered heterocyclic ring chosen from the azetidine, pyrrolidine, piperidine and azepine rings, these heterocyclic rings being capable of being substituted by an alkyl radical on the nitrogen atom, and Y is defined as above, can be prepared by the action of a product of general formula:

$$R_6-CO-Q \quad (X)$$

in which R$_6$ denotes a hydrogen atom or an alkyl radical and Q denotes a halogen atom or an alkylcarbonyloxy radical, on a product of general formula:

in which Y is defined as before and R'$_3$ has the corresponding definition of R$_3$ which is given above.

The reaction is usually carried out in an organic solvent such as pyridine, in a chlorinated solvent (methylene chloride) or an ether (tetrahydrofuran) in the presence of an acid acceptor such as an organic base such as triethylamine or an inorganic base such as an alkali metal carbonate or bicarbonate such as sodium bicarbonate, the operation being carried out at a temperature between 0° and 80° C.

It is to be understood that, when R'$_3$ denotes a radical containing a secondary amine group, the said group must be protected before the product of general formula (X) is reacted with the product of general formula (XI). The protection is carried out under the conditions described earlier for the preparation of the product of the general formula (II).

It is also to be understood that, when R$_2$ and/or R$_3$ in the general formula (VIII) denote a radical containing a secondary amine group, the latter must be protected beforehand, before the product of general formula (VIII) is reacted with the product of general formula (IX). The blocking and the deblocking are carried out as described earlier.

The products of general formula (V) defined as before under (2), in which Y is defined as before and the other symbols are defined as before under (2) (a) can be prepared by the action of a product of general formula:

$$R'_4-H \quad (XII)$$

in which R'$_4$ has the definition of R$_4$ given earlier under (2) (a), on the product of general formula:

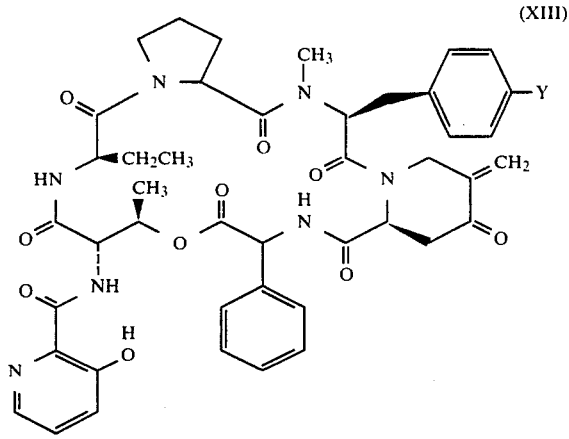

in which Y is defined as before.

The operation is usually carried out in an organic solvent such as an alcohol such as methanol, or a chlorinated solvent such as chloroform, or a mixture of these solvents, at a temperature between 0° C. and the reflux temperature of the reaction mixture, preferably at a temperature in the region of 20° C.

The products of general formula (XIII) can be prepared by the action of an alkali metal borohydride such as sodium cyanoborohydride on a product of general formula:

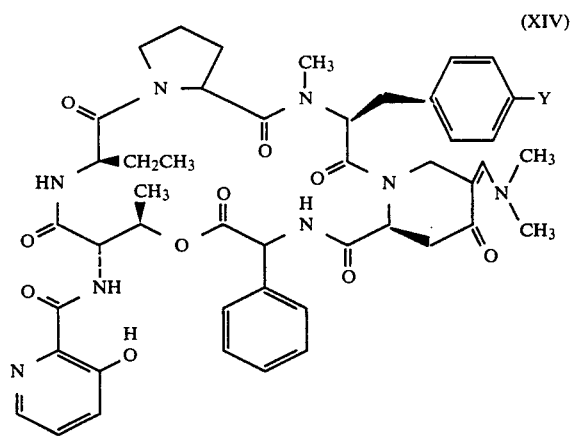

in which Y is defined as before.

The operation is usually carried out in an organic solvent such as an ether such as tetrahydrofuran, or an alcohol, for example isopropanol, in the presence of an acid such as trifluoroacetic acid, at a temperature between 0° C. and the reflux temperature of the reaction mixture, preferably at a temperature in the region of 20° C.

The products of general formula (XIV) can be obtained by the action of a product of formula:

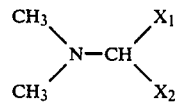

in which either $X_1$ denotes an alkyloxy radical and $X_2$ denotes an alkyloxy or dimethylamino radical, or $X_1$ and $X_2$ both denote a dimethylamino radical, on a product of general formula (IX).

In practice, it is advantageous to react tertbutoxybis(dimethylamino)methane with the product of general formula (IX), the operation being carried out in an organic solvent such as a chlorinated solvent such as 1,2-dichloroethane, or an amide (for example dimethylformamide) at a temperature between 0° and 80° C., preferably at a temperature in the region of 20° C.

The products of general formula (XV) can be prepared according to the methods described by H. Bredereck et al., Chem. Ber., 101, 41 and 3058 (1968) and Chem. Ber., 106, 3725 (1973).

The products of general formula (V) in which Y is defined as before and the other symbols are defined as earlier under (2) (b), except for $R_4$ denoting a 3-pyrrolidinyloxy, 3- or 4-piperidyloxy or alkyloxy radical, optionally substituted as defined under (2) (b), can be prepared by the action of a product of general formula:

$$R''_4-H \qquad (XVI)$$

in which $R''_4$ has the definition of $R_4$ given above, on a product of general formula (XIV) in which Y is defined as earlier.

The reaction is carried out in an organic medium in the presence of an acid (for example acetic acid or a mixture of acetic acid with catalytic quantities of trifluoroacetic acid), in the presence or absence of a solvent, at a temperature beween 0° and 50° C.; preferably at a temperature in the region of 20° C.

Where applicable, the solvent can be chosen from organic solvents such as ethers (tetrahydrofuran), alcohols (ethanol) and chlorinated solvents (methylene chloride or chloroform, for example).

The products of general formula (V) in which Y is defined as before and the other symbols are defined as earlier under (2) (b) can be prepared by the action of a product of general formula:

$$R'''_4-H \qquad (XVII)$$

in which $R'''_4$ is defined as $R_4$ under (2) (b), on a product of general formula:

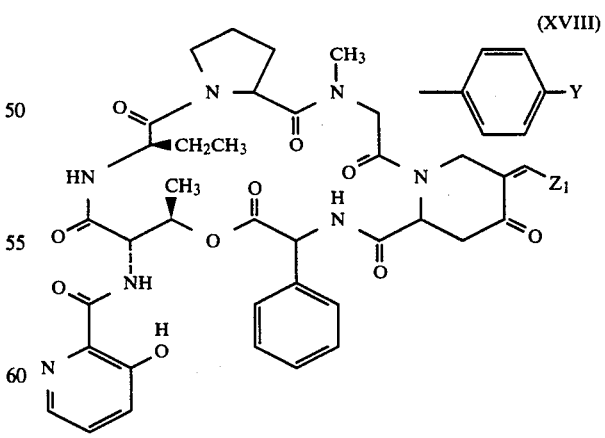

in which Y is defined as before and $Z_1$ denotes a tosyloxy, acetyloxy, trimethylsilyloxy or dialkyloxyphoshoryloxy radical whose alkyl moieties contain 1 to 4 carbon atoms forming a linear or branched chain or $Z_1$ denotes a chlorine atom.

The operation is usually carried out in an organic solvent such as ether such as tetrahydrofuran, an alcohol such as ethanol, or a chlorinated solvent (methylene chloride or chloroform, for example) at a temperature in the region of 20° C. The reaction is carried out in a basic medium, for example in the presence of an alkali metal hydride or an alkali metal alcoholate such as sodium ethoxide or potassium tert-butoxide.

When R'''₄ is different from a substituted alkyloxy or (heterocyclic ring radical)oxy radical, it is also possible to operate either in a neutral medium at a temperature between 0° and 50° C., in one of the solvents mentioned above, or in an acetic medium under conditions identical to those described earlier for the action of a product of general formula (XVI) on a product of general formula (XIV).

The products of general formula (XVIII) can be prepared by acid hydrolysis of a product of general formula (XIV) to obtain a product of general formula:

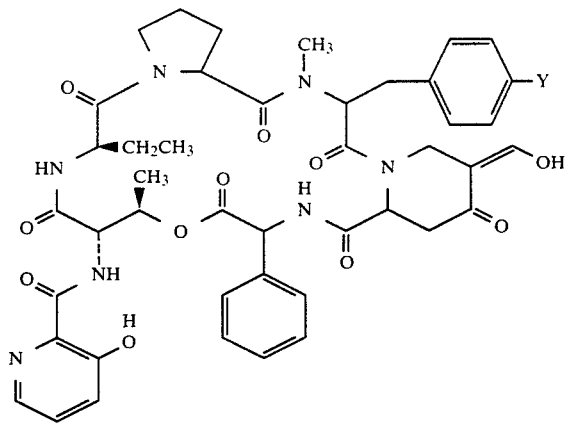

(XIX)

followed:

(α) either by the action of a product of general formula:

Z'₁—X  (XX)

in which X denotes a halogen atom and Z'₁ has the definition given before for Z₁, except for denoting a chlorine atom (β) or by the action of a product of formula:

(C₆H₅)₃PCl₂  (XXI)

to obtain a product of general formula (XVIII) in which Z₁ denotes a chlorine atom.

The hydrolysis of the product of general formula (XIV) to the product of general formula (XVIII) is carried out by means of an aqueous solution of an inorganic acid such as a 0.1N aqueous solution of hydrochloric acid, the operation being carried out at a temperature in the region of 20° C.

The reaction of the product of general formula (XX) with the product of general formula (XIX) is generally carried out in an organic solvent such as methylene chloride in the presence of an acid-acceptor such as an organic base such as triethylamine, or an inorganic base such as an alkali metal carbonate or bicarbonate, for example sodium or potassium bicarbonate. The operation is generally carried out at a temperature between −20° and +20° C.

The reaction of the product of general formula (XXI) with the product of general formula (XIX) is usually carried out in a chlorinated solvent such as methylene chloride at a temperature between −20° and +20° C.

The products of general formulae (III), (VIII), (XII), (XVI) and (XVII) can be prepared according to, or in a similar manner to, the methods described in the examples below, and especially according to:

G. G. Urquart et al., Org. Synth., 21, 36 (1941)
A. I. Vogel, J. Chem. Soc., 1822 (1948)
J. H. Chapman and L. N. Owen, J. Chem. Soc., 579 (1950)
H. R. Snyder et al., J. Am. Chem. Soc., 69, 2672 (1947)
D. D. Reynolds et al., J. Org. Chem., 26, 5125 (1961)
J. W. Haeffele et al., Proc. Sci. Toilet Goods Assoc., 32, 52 (1959)
H. Barrer et al., J. Org. Chem., 27 641 (1962)
J. H. Biel et al., J. Amer. Chem. Soc., 77, 2250 (1955)
when dealing with a product of general formula (III), (XII), (XVI) or (XVII) in which R, R'₄, R''₄ or R'''₄ denotes a substituted alkylthio or (heterocyclic ring radical)thio radical, or according to:
A. J. W. Headlee et al., J. Amer. Chem. Soc., 55, 1066 (1933)
B. K. Campbell and K. N. Campbell, J. Amer. Chem. Soc., 60, 1372 (1938)
R. C. Elderfield et al., J. Amer. Chem. Soc., 68, 1579 (1946)
when dealing with a product of general formula (XIV) or (XVII) in which R''₄ or R'''₄ denotes a substituted alkyloxy or (heterocyclic ring radical)oxy radical, or according to:
J. Amer. Chem. Soc., 54, 1499 (1932) and
J. Amer. Chem. Soc., 54, 3441 (1932),
when dealing with a product of general formula (VIII) or of general formula (III), (XVI) or (XVII) in which R, R''₄ or R'''₄ are substituted alkylamino radicals, or according to:
E. F. Elslager et al., J. Med. Chem., 17, 99 (1974)
L. M. Werbel et al., J. Het. Chem., 10, 363 (1973)
when dealing with a product of general formula (III), (XVI) or (XVII) in which R, R''₄ or R'''₄ are (heterocyclic ring radical)amino radicals.

It is to be understood that in the above methods, when R, R₂, R₃, R'₄, R''₄ or R'''₄ contain a secondary amine group capable of interfering with the reaction, this must first be protected by any known method which does not affect the remainder of the molecule. The protective radical is removed after reaction under the conditions described earlier.

Where applicable, the isomers of the products of general formula (I) and/or the products of general formula (V) can be separated by chromatography or by high performance liquid chromatography.

The products of general formula (V) can be purified as mentioned earlier for the products of general formula (I).

The pristinamycin II$_B$ derivatives of formula (I) and their pharmaceutically acceptable salts exhibit particularly advantageous antibacterial properties in vitro and in vivo.

In vitro, the products of formula (I) have shown themselves to be active towards *Staphylococcus aureus* Smith at concentrations from 4 to 100 μg/cm³. In addition, they have a synergistic effect on the antibacterial action of pristinamycin I$_A$ in concentrations greater than 0.1 and 10 μg/cm³.

In vivo, the products of formula (I) have shown themselves to be active in the mouse in experimental infections with *Staphylococcus aureus* Smith at dosages between 40 mg/kg and dosages greater than 300 mg/kg by the subcutaneous route. When they are combined with pristinamycin $I_A$ in proportions from 10–90% to 90–10%, they have a synergistic effect on the antimicrobial action at dosages between 8 and 200 mg/kg by the subcutaneous route.

The acute toxicity of the products of formula (I), expressed as their $LD_{50}$, is generally between 300 mg/kg and dosages greater than 1 g/kg by the subcutaneous route in the mouse.

The products of special interest are those of formula (I) in which the symbol R denotes:
either a nitrogen-containing 5 or 6-membered heterocyclic ring radical unsubstituted or substituted by an alkyl radical,
or an alkyl chain of 2 to 4 carbon atoms and substituted by 1 or 2 radicals chosen from phenyl, cycloalkylamino of 3 to 6 ring atoms, and N-alkyl-N-cycloalkylamino of 3 to 6 ring atoms, alkylamino, dialkylamino, dialkylcarbamoyloxy (the alkyl moieties of these two latter radicals being unjoined or joined to form, with the nitrogen atom to which they are attached, a saturated or unsaturated 5 or 6-membered heterocyclic ring which may contain another hetero atom chosen from nitrogen, oxygen and sulphur in the form of sulphoxide or sulphone, and unsubstituted or substituted by alkyl), or substituted by a nitrogen-containing 5 or 6-membered heterocyclic ring which may contain another hetero atom chosen from nitrogen, oxygen and sulphur in the form of sulphoxide or sulphone and unsubstituted or substituted by alkyl, this heterocyclic ring being linked to the alkyl by a carbon atom of the ring, it being understood that a least one of the substituents carried by the above alkyl chain is a nitrogen-containing substituent capable of forming salts, and n is 1 or 2; and, among these products, those which are especially active are the products of formula (I) in which R denotes an alkyl chain containing 2 to 4 carbon atoms substituted by 1 or 2 radicals chosen from phenyl, cycloalkylamino of 5 to 6 ring atoms, N-alkyl-N-cycloalkylamino of 5 or 6 ring atoms, alkylamino of 1 to 4 carbon atoms, and dialkylamino (in which the alkyl moieties contain 1 to 3 carbon atoms each or form, with the nitrogen atom to which they are attached, a saturated 5 or 6-membered heterocyclic ring), or R denotes a nitrogen-containing 5 or 6-membered heterocyclic ring unsubstituted or substituted by alkyl of 1 to 4 carbon atoms, at least one of the substituents carried by the alkyl chain being a nitrogen-containing substituent capable of forming salts, and at least one of the radicals carried by this chain is placed in a 1- or 2-position, and n is 1 or 2.

The following derivatives of pristinamycin $II_B$ of formula (I) are of especial interest.
26-(2-diethylamino-1-methylethyl)sulphinylpristinamycin $II_B$
26-[(2R)2-dimethylaminobutyl]sulphinylpristinamycin $II_B$
26-(2-diethylaminopropyl)sulphinylpristinamycin $II_B$
26-(2-diisopropylaminoethyl)sulphonylpristinamycin $II_B$.

For use in therapy, the compounds of formula (I) can be used as such, that is to say in the form of the base, in combination with already known synergistins, but, since the chief advantage of the products of the invention is their solubility in water, it is especially advantageous to use them in the form of pharmaceutically acceptable salts, in combination with known synergistins or with the synergistins of formula (V), dissolved either in the form of pharmaceutically acceptable salts or, where applicable, in the form of the base when the solubility is sufficient for the solution produced to contain (in a volume suitable for a single dose) a quantity of active ingredient which is at least equal to the therapeutically active dose.

Both for the products of formula (I) and for the products of formula (V), the pharmaceutically acceptable salts which can be mentioned are the salts of addition with inorganic acids such as hydrochlorides, hydrobromides, sulphates, nitrates, phosphates, or with organic acids, such as acetates, propionates, succinates, maleates, fumarates, methanesulphonates, p-toluenesulphonates, isethionates, or substitution derivatives of these compounds. There can also be mentioned, as pharmaceutically acceptable salts, the salts with alkali metals (such as sodium and potassium salts), with alkaline-earth metals (such as the magnesium salt), the ammonium salt and salts of addition with nitrogen-containing organic bases (ethanolamine, diethanolamine, trimethylamine, triethylamine, methylamine, propylamine, diisopropylamine, N,N-dimethylethanolamine, benzylamine, dibenzylamine, dicyclohexylbenzylamine, N-benzyl-$\beta$-phenethylamine, N,N'-dibenzylethylenediamine, benzhydrylamine, arginine, leucine, lysine or N-methylglucamine).

Quaternary ammonium salts corresponding to the anions listed above can be mentioned as pharmaceutically acceptable salts for the products of general formula (V) in which Z denotes a radical of general formula (VII) in which $R_4$ denotes a trialkylammonio radical.

The following examples, given without implying any limitation, show how the invention can be put into practice. The NMR spectra of the products illustrated in these examples and in the reference examples which follow, show general characteristics which are common to all the products of general formula (I) or of general formula (V) and individual characteristics which are specific to each of the products, depending on the substituents. Only the individual characteristics due to the changeable radicals are mentioned in the examples or reference examples which follow. For the products of general formula (I), all the protons are designated according to the numbering indicated in the following formula:

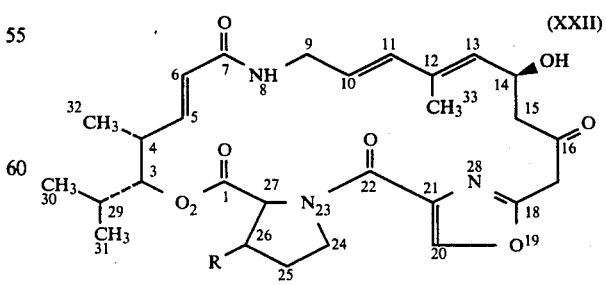

(XXII)

For the synergistins of general formula (V) all the protons are designated according to the numbering indicated in the general formula (XXIII); this numbering is that recommended by J. O. Anteunis et al., [Eur. J. Biochem., 58, 259 (1975)].

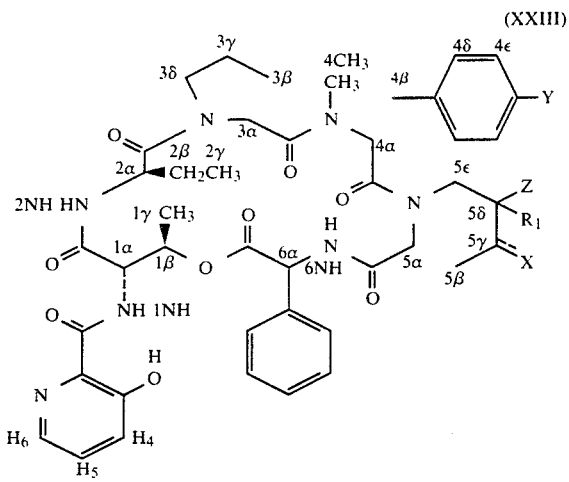

(XXIII)

Unless stated otherwise, all the spectra were recorded at 250 MHz in deuterochloroform; the chemical shifts are expressed in ppm relative to the tetramethylsilane signal. The abbreviations used in the following text are as follows:

s = singlet
d = doublet
t = triplet
mt = multiplet
m = unresolved bands
dd = doublet of doublets
dt = doublet of triplets
ddd = doublet of doublets of doublets
dddd = doublet of doublets of doublets of doublets It is to be understood that the various isomers have been classified arbitrarily according to the chemical shifts observed in NMR.

The names isomer $A_1$ and isomer $A_2$ of the products of general formula (I) in which $n=1$ are given to the isomers which have the characteristics: approximately 1.7 (s, —CH$_3$ at 33); approximately 3.8 (s, >CH$_2$ at 17); <5 (d, —H$_{27}$) isomer $A_2$ or >5 (d, —H$_{27}$) isomer $A_1$; approximately 5.50 (broad d, —H$_{13}$); approximately 6.20 (d, —H$_{11}$); approximately 6.6 (>NH at 8); >8 (s, —H$_{20}$).

The names isomer $B_1$ and isomer $B_2$ of the products of general formula (I) in which $n=1$ are given to the isomers which have the characteristics: approximately 1.5 (s, —CH$_3$ at 33); approximately 3.7 and 3.9 (2d, >CH$_2$ at 17); approximately 4.8 (mt, —H$_{13}$); <5 (d, —H$_{27}$) isomer $B_2$ or >5 (d, —H$_{27}$) isomer $B_1$; approximately 5.70 (borderline AB, —H$_{11}$ and —H$_{10}$); approximately 7.7 (>NH at 8); approximately 7.8 (s, —H$_{20}$).

The name isomer A of the product of general formula (II) is given to the isomer which has NMR characteristics identical to those listed above for the isomers $A_1$ and $A_2$ of the products of general formula (I), it being understood that the H at 27 is characterized by: 4.7 (d, $J \leq 1$ Hz).

The name isomer B of the product of general formula (II) is given to the isomer which has NMR characteristics identical to those listed above for the isomers $B_1$ and $B_2$ of the products of general formula (I), it being understood that the H at 27 is characterized by: 4.6 (d, $J \leq 2.5$ Hz).

In the following examples, the name "flash" chromatography is given to a purification technique in which a short chromatography column is used and operated under an intermediate pressure (50 kPa) with the use of a silica with a particle size distribution of 40-53 μm, according to W. C. Still, M. Kahn and A. Mitra (J. Org. Chem. 43, 2923 (1978).

In the examples described below, unless stated otherwise, all the products can be dissolved at a strength of at least 2%, in the form of hydrochloride.

EXAMPLE 1

Trifluoroacetic acid (0.4 cc), and then 85% metachlorobenzoic acid (1.06 g) are added, under a nitrogen atmosphere; while the temperature is maintained at 0° C., to 26-(2-diisopropylaminoethyl)thiopristinamycin II$_B$ (isomer A) (3.59 g) dissolved in dichloromethane (40 cc) at 0° C. After 20 hours' stirring at 25° C., the reaction mixture is added to a saturated aqueous solution of sodium bicarbonate. The organic phase is separated off and then the aqueous phase is washed with methylene chloride (3×100 cc). The organic phase are combined, dried over magnesium sulphate, filtered and then concentrated to dryness under reduced pressure (2.7 kPa) at 30° C. to give a yellow solid (4.2 g) which is purified by "flash" chromatography [(eluent: chloroform-methanol (90-10 by volume)], 20-cc fractions being collected. Fractions 22 to 28 are combined and concentrations to dryness under reduced pressure (2.7 kPa) at 30° C., to give a light-yellow solid, which is stirred in ethyl ether (10 cc). The solid obtained is separated off by filtration to give 26-(2-diisopropylaminoethyl)sulphinylpristinamycin II$_B$ (isomer $A_2$) (0.62 g) in the form of a yellow powder melting at about 155° C.

NMR spectrum:

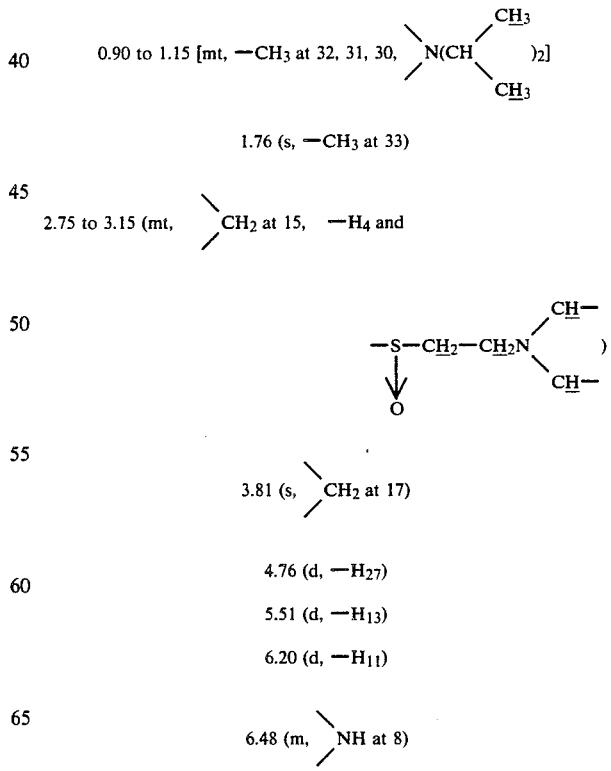

-continued 8.13 (S, —H$_{20}$)

Fractions 35 to 45 are combined and concentrated to dryness under reduced pressure (2.7 kPa) at 30° C. to give a light-yellow solid which is stirred in ethyl ether (15 cc). The solid obtained is separated off by filtration to give 26-(2-diisopropylaminoethyl)sulphinylpristinamycin II$_B$ (80% isomer A$_1$, 20% isomer A$_2$) (1.07 g) in the form of a light-yellow powder melting at about 145° C.

NMR spectrum (isomer A$_1$):

1.72 (s, —CH$_3$ at 33)

2.70 to 3.15 (mt, \>CH$_2$ at 15, —H$_4$, $$-S-CH_2-CH_2-N-CH\begin{matrix}\diagup\\\diagdown\end{matrix}\\\phantom{-S-CH_2-CH_2-N-}\big|\phantom{CH}\\\phantom{-S-CH_2-CH_2-N}CH\begin{matrix}\diagup\\\diagdown\end{matrix}$$
↓
O 3.81 (s, \>CH$_2$ at 17)

5.26 (d, —H$_{27}$)

5.46 (d, —H$_{13}$)

6.15 (d, —H$_{11}$)

8.11 (s, —H$_{20}$)

26-(2-Diisopropylaminoethyl)thiopristinamycin II$_B$ can be prepared as follows:

2-Diisopropylaminoethanethiol (16 g) dissolved in dichloromethane (30 cc) is added dropwise under a nitrogen atmosphere to pristinamycin II$_A$ (52 g) dissolved in a mixture of dichloromethane (260 cc) and methanol (520 cc), at −30° C. The solution is stirred at −20° C. for 20 hours and then concentrated under reduced pressure (2.7 kPa) at 30° C. The solid obtained is stirred with ethyl ether (2×1000 cc), separated off by filtration and then crystallized from acetonitrile (100 cc). The crystals are separated off by filtration and then dried under reduced pressure (90 Pa) at 40° C. In this manner, 26-(2-diisopropylaminoethyl)thiopristinamycin II$_B$ (isomer A) (33.6 g) is obtained in the form of white crystals melting at about 122° C.

NMR spectrum:

1 to 1.15 (mt, isopropyl-CH$_3$)
1.72 (s, —CH$_3$ at 33)
1.80 to 2.20 (mt, —H$_{25}$, —H$_{29}$)

2.50 to 3 (mt, —SCH$_2$CH$_2$—N(CH)(CH))

-continued 3.40 (broad d, —H$_{26}$)
4.74 (broad s, —H$_{27}$)
6.32 (m, —NH$_8$)
8.15 (s, —H$_{20}$)

2-Diisopropylaminoethanethiol can be prepared according to the method described by D. D. Reynolds, D. L. Fields and D. L. Johnson, J. Org. Chem. 26, 5125 (1961).

EXAMPLE 2

Sodium bicarbonate (1.22 g) is added to 26-(2-diisopropylaminoethyl)thiopristinamycin II$_B$ (isomer A) (10 g) dissolved in chloroform (300 cc). The mixture is cooled to −50° C. and 98% meta-chloroperbenzoic acid (2.98 g) dissolved in chloroform (100 cc) is added dropwise. The mixture is stirred at −50° C. for 2 hours 15 minutes and then a saturated aqueous solution of sodium bicarbonate is added to it. After 15 minutes' stirring at 25° C., the mixture is separated and then the aqueous phase is washed with dichloromethane (3×200 cc). The organic phases are combined, dried over magnesium sulphate, filtered, and then concentrated to dryness under reduced pressure (2.7 kPa) at 30° C. to give a whitish porous solid (10.62 g). The latter is dissolved in ethyl acetate (400 cc) and then treated with a 0.1N aqueous solution of hydrochloric acid (140 cc). The pH of the aqueous solution is then adjusted to 4.2 by adding a pH 4.2 buffer (400 cc). The aqueous phase is separated off and then the organic phase is washed with pH 4.2 buffer (400 cc). The aqueous phases are combined and washed with ethyl acetate (2×150 cc). After separation, the aqueous phase is adjusted to pH 7–8 adding sodium bicarbonate and is then washed with dichoromethane (3×300 cc). The organic phases are combined and then washed with pH 7.5 buffer (2×200 cc). The aqueous phase is washed with dichloromethane (50 cc) and then the organic phases are combined, dried over magnesium sulphate, filtered and concentrated to dryness under reduced pressure (2.7 kPa) at 30° C., to give a light-yellow solid (8.04 g), which is stirred in ethyl ether (100 cc), separated off by filtration and then dried under reduced pressure (90 Pa) at 40° C. In this manner, 26-(2-diisopropylaminoethyl)sulphinylpristinamycin II$_B$ (isomer A$_2$) (7.5 g) is obtained in the form of a yellow powder melting at about 158° C., the NMR characteristics of which are identical to those in Example 1.

EXAMPLE 3

The method used is that described in Example 1, but starting with 26-(2-diethylaminoethyl)thiopristinamycin II$_B$ (53.2 g), trifluoroacetic acid (6.25 cc) and meta-chloroperbenzoic acid (16.4 g). Three successive purifications by "flash" chromatography are carried out [eluent: chloroform-methanol (90–10 by volume)], 40-cc fractions being collected, according to the following scheme:

Purification scheme

BATCH A (68 g)

-continued

Purification scheme

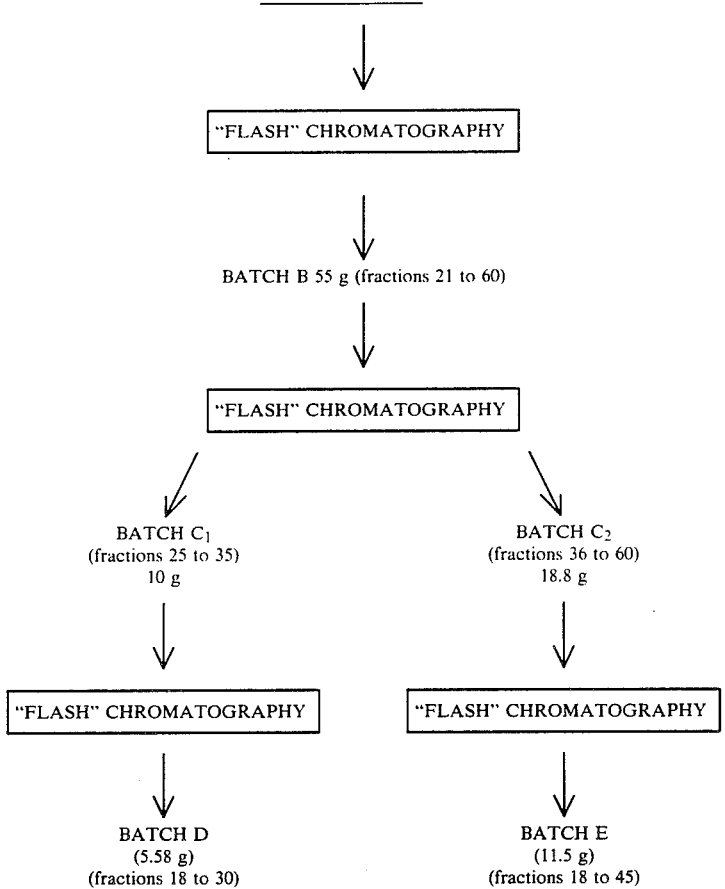

In all cases, the fractions recovered are concentrated to dryness under reduced pressure (2.7 kPa) at 30° C.

Batch D is stirred in ethyl ether (60 cc). The solid obtained is separated off by filtration. 26-(2-Diethylaminoethyl)sulphinylpristinamycin II$_B$ (isomer A$_2$) (5 g) is obtained in the form of a yellow powder melting at about 172° C.

NMR spectrum:

1.00 to 1.14 (mt, —CH$_3$ at 32 + chain CH$_3$)
1.75 (s, —CH$_3$ at 33)

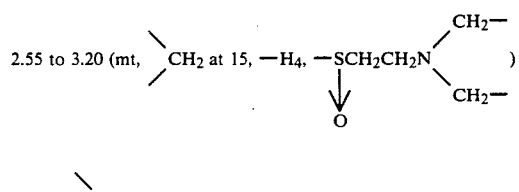

3.82 (s, $\diagdown$CH$_2$ at 17)

4.81 (d, —H$_{27}$)
5.51 (d, —H$_{13}$)
6.19 (d, —H$_{11}$)

6.46 (dd, $\diagdown$NH at 8)

8.13 (S, —H$_{20}$)

Batch E is stirred in ethyl ether (10 cc). The solid obtained is separated off by filtration. 26-(2-Diethylaminoethyl)sulphinylpristinamycin II$_B$ (60% isomer A$_2$), 15% isomer A$_1$, 12% isomer B$_1$, 13% isomer B$_2$) (10.9 g) is obtained.

NMR spectrum: 1.00 to 1.13 (mt, —CH$_3$ at 32 and —N(CH$_2$CH$_3$)$_2$ of A$_1$ and A$_2$), 1.54 (s, —CH$_3$ at 33 of B$_1$ and $\overline{B_2}$), 1.68 (s, —CH$_3$ at 33 of A$_1$), 1.75 (s, —CH$_3$ at 33 of A$_2$), 2.65 to 2.95 (mt, —S(O)CH$_2$CH$_2$N< and H$_4$ of A$_1$) 2.55 to 3.20 (mt, >CH$_2$ at 15, —H$_4$ and —S(O)CH$_2$CH$_2$N< of A$_2$), 3.77 (borderline AB, >CH$_2$ at 17 of $\overline{A_1}$), 3.82 (s, >CH$_2$ at 17 of A$_2$), 4.81 (d, —H$_{27}$ of A$_2$), 5.24 and 5.25 (2d, —H$_{27}$ of A$_1$ and of B$_1$), 5.41 (d, —H$_{13}$ of A$_1$), 5.51 (d, —H$_{13}$ of A$_2$), 5.99 and 6 (2d, —H$_6$ of B$_1$ and —H$_6$ of B$_2$), 6.11 (d, —H$_{11}$ of A$_1$), 6.19 (d, —H$_{11}$ of A$_2$), 6.46 (dd, >NH at 8 of A$_2$), 6.79 (dd, >NH at 8 of A$_1$), 7.82 (s, —H$_{20}$ of B$_1$ and B$_2$), 8.12 (s, —H$_{20}$ of A$_1$), 8.13 (s, —H$_{20}$ of A$_2$).

26-(2-Diethylaminoethyl)thiopristinamycin II$_B$ can be prepared as follows: A solution of diethylaminoethanethiol (3.7 g) in methylene chloride (15 cc) is added to a suspension of pristinamycin II$_A$ (13.1 g) in methanol (150 cc). The solution obtained is stirred at a temperature of about 20° C. for 18 hours and is then poured into distilled water (1500 cc); the mixture obtained is extracted 3 times with methylene chloride (1000 cc in total). The organic phases are combined, dried over magnesium sulphate, filtered and then concentrated to dryness under reduced pressure (2.7 kPa) at 30° C. The residue obtained is purified by "flash" chromatography [eluent: chloroform-methanol (90–10 by volume)]; after fractions 5 to 23 have been concentrated to dryness under reduced pressure (2.7 kPa) at 30° C., 26-(2-diethylaminoethyl)thiopristinamycin II$_B$ (12.4 g) is obtained in the form of a yellow powder melting at about 105° C.

NMR spectrum: 1.05 (m, —N(CH$_2$CH$_3$)$_2$+—H$_{32}$), 1.70 (s, —H$_{33}$), 1.85 to 2.15 (m, —H$_{25}$, —H$_{29}$), 2.60 (q, —N(CH$_2$CH$_3$)$_2$), 2.75 (s, —S—CH$_2$CH$_2$—), 2.9 (dd, ABX system, —H$_{15}$), 3.10 (dd, ABX system, —H$_{15}$), 3.40 (ddd, —H$_{26}$), 3.80 (s, —H$_{17}$), 4.75 (d, —H$_{27}$), 5.50 (d, —H$_{13}$), 6.15 (d, —H$_{11}$), 6.60 (broad s, >NH at 8), 8.10 (s, —H$_{20}$).

EXAMPLE 4

By using a method similar to that described in Example 1, but starting from 26-(2-dimethylaminoethyl)thiopristinamycin II$_B$ (5.5 g), trifluoroacetic acid (0.67 cc) meta-chloroperbenzoic acid (1.8 g), and after a purification by "flash" chromatography [eluent: chloroform-methanol (90–10 by volume)], 30-cc fractions being collected, and concentrating fractions 23 to 40 to dryness under reduced pressure (2.7 kPa) at 30° C., 26-(2-dimethylaminoethyl)sulphinylpristinamycin II$_B$ (70% isomer A$_2$, 15% isomer A$_1$, 7% isomer B$_1$, 8% isomer B$_2$) (0.4 g) is obtained in the form of a yellow powder melting at about 150° C.

NMR spectrum (isomer A$_2$):

1.77 (s, —CH$_3$ at 33)
2.41 (s, —N(CH$_3$)$_2$)

2.70 to 3.20 (mt, —SCH$_2$CH$_2$N$\diagdown\diagup$, $\diagdown\diagup$CH$_2$ at 15 and —H$_4$)
$\downarrow$
O 3.82 (s, $\diagdown\diagup$CH$_2$ at 17)

4.84 (mt, —H$_3$ and —H$_{27}$)
5.52 (d, —H$_{13}$)
6.19 (d, —H$_{11}$)

6.42 (m, $\diagdown\diagup$NH at 8)

8.14 (s, —H$_{20}$)

26-(2-Dimethylaminoethyl)thiopristinamycin II$_B$ can be prepared as follows:

By using a mthod similar to that described in Example 3, but starting from pristinamycin II$_A$ (2.7 g) and 2-dimethylaminoethanethiol (0.58 g) and after purification by "flash" chromatography [eluent: chloroform-methanol (90–10 by volume)] and concentrating fractions 11 to 17 to dryness under reduced pressure (2.7 kPa) at 30° C., 26-(2-dimethylaminoethyl)thiopristinamycin II$_B$ (1.1 g) is obtained in the form of a yellow powder melting at about 100° C.

NMR spectrum: 2.35 (s, 6H: —N(CH$_3$)$_2$), 2.80 (m, 4H: —S—CH$_2$CH$_2$—N<), 3.40 (ddd, 1H: —H$_{26}$), 4.75(d, 1H: —H$_{27}$), 8.10 (S, 1H: —H$_{20}$).

EXAMPLE 5

By using the same method as that described in Example 2, but startng from 26-(2-N-methyl-N-ethylaminoethyl)thiopristinamycin II$_B$ (90% isomer A 10% isomer B). (4.7 g), sodium bicarbonate (1.22 g), and 98% meta-chloroperbenzoic acid (1.41 g), and after purification by "flash" chromatography [eluent: dichloromethane-methanol (90–10 by volume)], 20-cc fractions being collected, and concentrating fractions 44 to 52 to dryness under reduced pressure (2.7 kPa) at 30° C., a yellow solid (2.47 g) is obtained, which is stirred in ethyl ether (50 cc), separated off by filtration and then dried under reduced pressure (90 Pa) at 40° C. In this manner, 2-(N-methyl-N-ethyl-2-aminoethyl)sulphinylpristinamycin II$_B$ (isomer A$_2$) (2.3 g) is obtained in the form of a yellow powder melting at about 145° C.

NMR spectrum 1.09 (t, $\diagdown\diagup$N—CH$_2$—CH$_3$)

1.76 (s, —CH$_3$ at 33)

2.31 (s, $\diagdown\diagup$N—CH$_3$)

2.54 (mt, $\diagdown\diagup$N—CH$_2$CH$_3$)

2.80 (mt, —H$_4$)

2.70 to 3.10 (mt, —S—CH$_2$—CH$_2$N$\diagup\diagdown$ )
$\downarrow$
O 2.92 to 3.12 (2dd, $\diagdown\diagup$CH$_2$ at 15)

3.24 (mt, —H$_{26}$)

3.82 (s, $\diagdown\diagup$CH$_2$ at 17)

4.82 (s, —H$_{27}$)
5.51 (d, —H$_{13}$)

6.40 (dd, $\diagdown\diagup$NH at 8)

8.13 (S, —H$_{20}$)

26-(N-Methyl-N-ethyl-2-aminoethyl)thiopristinamycin II$_B$ (90% isomer A, 10% isomer B) can be prepared by using the same procedure as that described in Example 1, but starting from pristinamycin II$_A$ (14.11 g) and N-methyl-N-ethyl-2-aminoethanethiol (3.2 g). After stirring for 4 days at −20° C. and purification by "flash" chromatography [eluent: chloroform-methanol (90–10 by volume)], 80-cc fractions being collected, followed by concentration of fractions 25 to 48 to dryness under reduced pressure (2.7 kPa) at 30° C., a yellow solid (4.75 g) is obtained, which is dried under reduced pressure (90 kPa) at 40° C. In this manner, 26-(N-methyl-N-ethyl-2-aminoethyl)thiopristinamycin $II_B$ (90% isomer A, 10% isomer B) (4.7 g) is obtained in the form of a yellow powder melting at about 140° C.

NMR spectrum: 1.1 (mt, $CH_2C\underline{H}_3$), 1.73 (s, $CH_3$ at 33), 2.30 (s, $>N—CH_3$), 2.45 to 2.6 (mt, $>N—C\underline{H}_2CH_3$), 2.68 to 2.78 (2mt, $—S—CH_2—CH_2N<$), 2.78 (mt, $—H_4$), 2.90 and 3.12 (2dd, $—CH_2—$ at 15), 3.40 (d, $—H_{26}$), 3.83 (s, $—CH_2—$ at 17), 4.76 (s, $—H_{27}$), 5.48 (d, $—H_{13}$), 6.14 (d, $—H_{11}$), 6.34 (mf, $>NH$ at 8), 8.11 (s, $—H_{20}$).

N-Methyl-N-ethyl-2-aminoethanethiol can be obtained by a method similar to that described by D. D. Reynolds et al., J. Org. Chem. 26, 5125 (1961), from N-methyl-N-ethylamine (25 g) and ethylene thiocarbonate (43.7 g). After distillation. N-methyl-N-ethyl-2-aminoethanethiol (1.3 g) is obtained in the form of a colourless liquid.

[B.p. (6.7 kPa)=52° C.]

EXAMPLE 6

Using a method similar to that described in Example 1, but starting from 26-(3-dimethylaminopropyl)thiopristinamycin $II_B$ (50:50 A/B isomers) (9.8 g), trifluoroacetic acid (1.18 cc) and meta-chloroperbenzoic acid (3.1 g) and after purification by "flash" chromatography [eluent: chloroform-methanol (80–20 by volume)], 15-cc fractions being collected, and concentrating fractions 53 to 75 to dryness under reduced pressure (2.7 kPa) at 30° C., 26-(3-dimethylaminopropyl)sulphinylpristinamycin $II_B$ (mixed isomers) (1.6 g) is obtained in the form of a yellow powder melting at about 165° C.

NMR spectrum (mixture of isomers of type $A_2\simeq 45\%$, $B_2\simeq 35\%$ and $B_1\simeq 15\%$): 1.53 (s, $—CH_3$ at 33 $B_2$ and $B_1$), 1.75 (s, $—CH_3$ at 33 of $A_2$), 2.26, 2.28 and 2.32 (3s, $>NCH_3$ of the 3 isomers), 3.82 (s, $>CH_2$ at 17 of $A_2$), 3.70 and 3.88 (2d, $>CH_2$ at 17 of $B_1$), 3.69 and 3.91 (2d, $>CH_2$ at 17 of $B_2$), 4.76 (d, $—H_{27}$ of $B_2$), 5.25 (d, $—H_{27}$ Of $B_1$), 5.50 (d, $—H_{13}$ of $A_2$), 7.63 (mt, $>NH$ at 8 of $B_2$), 7.74 (mt, $>NH$ at 8 of $B_1$), 7.82 (s, $—H_{20}$ of $B_2$ and $B_1$), 8.14 (s, $—H_{20}$ of $A_2$). 26-(3-Dimethylaminopropyl)thiopristinamycin $II_B$ can be obtained as follows:

By using a method similar to that described in Example 3, but starting from pristinamycin $II_A$ (5.25 g) and 3-dimethyl-aminopropanethiol (1.3 g), and after purification by "flash" chromatography [eluent: chloroform-methanol (90–10 by volume)] and concentrating fractions 6 to 29 to dryness under reduced pressure (2.7 kPa) at 30° C., 26-(3-dimethylaminopropyl)thiopristinamycin $II_B$ (3.3 g) is obtained in the form of a yellow powder melting at about 100° C.

NMR spectrum:

| | |
|---|---|
| 1.50 | (s, 3H × 0.5: $—H_{33}$ 1st isomer) |
| 1.70 | (s, 3H × 0.5: $—H_{33}$ 2nd isomer) |
| 1.80 | (m, 2H: $—SCH_2—C\underline{H}_2—CH_2N<$) |
| 2.20 | (s, 6H × 0.5: $—N(CH_3)_2$ 1st isomer) |
| 2.25 | (s, 6H × 0.5: $—N(CH_3)_2$ 2nd isomer) |
| 2.40 | (m, 2H: $—SC\underline{H}_2—CH_2—CH_2N<$) |
| 2.70 | (m, 2H: $—SCH_2—CH_2—C\underline{H}_2N<$) |
| 3.35, 3.45 | (2m, 1H: $—H_{26}$ of each isomer) |
| 4.60, 4.70 | (2d, 1H: $—H_{27}$ of each isomer) |
| 7.80, 8.10 | (2s, 1H: $—H_{20}$ of each isomer) |

EXAMPLE 7

By using a method similar to that described in Example 1, but starting from 26-(2-diethylaminopropyl)thiopristinamycin $II_B$ (6.3 g), trifluoroacetic acid (0.72 cc) and meta-chloroperbenzoic acid (1.91 g), and after purification by "flash" chromatography [eluent: chloroform-methanol (90–10 volume)], 60-cc fractions being collected, and after concentrating fractions 7 to 9 to dryness under reduced pressure (2.7 kPa) at 30° C., 26-(2-diethylaminopropyl)sulphinylpristinamycin $II_B$ (isomers $A_2$) (0.99 g) is obtained in the form of a yellow powder melting at about 150° C.

NMR spectrum: 1.03 to 1.20 (mt, $—CH_2—CH(CH_3)N(CH_2CH_3)_2$), $CH_3$ at 32), 1.76 (s, $—CH_3$ at 33), 3.82 (s, $CH_2$ at 17), 4.79 (m, $—H_{27}$), 5.53 (d, $—H_{13}$), 6.20 (d, $—H_{11}$), 6.42 (m, $>NH$ at 8), 8.13 (s, $—H_{20}$).

After concentrating fractions 23 to 35 to dryness under reduced pressure (2.7 kPa) at 30° C., 26-(2-diethylaminopropyl)sulphinylpristinamycin $II_B$ (isomers $A_1$) (0.64 g) is obtained in the form of a beige-yellow powder melting at about 160°–170° C.

NMR spectrum:

1.14 (mt, $—N(CH_2C\underline{H}_3)_2$)

1.24 (broad d, $C\underline{H}_3—CH—N<$)

1.73 (s, $—CH_3$ at 33)

3.81 (borderline AB, $>CH_2$ at 17)

5.28 (d, $—H_{27}$)
5.43 (d, $—H_{13}$)
6.15 (d, $—H_{11}$)

6.88 (m, $>NH$ at 8)

8.10 (s, $—H_{20}$)

26-(2-Diethylaminopropyl)thiopristinamycin $II_B$ can be prepared as follows:

By using a method similar to that described in Example 3, but starting from pristinamycin $II_A$ (3.15 g) and 2-diethylaminopropanethiol (1.8 g), and after purification by "flash" chromatography [eluent: methylene chloride-methanol (90-10 by volume)], 20-cc fractions being collected, and concentrating fractions 3 to 5 to dryness under reduced pressure (2.7 kPa) at 30° C., 26-(2-diethylaminopropyl)thiopristinamycin $II_B$ (1.4 g) is obtained in the form of a yellow powder melting at about 160° C.

NMR spectrum:

1 (m, 9H: $-H_{32}$ + $-N(CH_2C\underline{H}_3)_2$)

2.50 (m, 6H: $-S-C\underline{H}_2-C\underline{H}-N(C\underline{H}_2CH_3)_2$)
|

3.30 (m, 1H: $-H_{26}$)
4.70 (d, 1H: $-H_{27}$)
8.12 (s, 1H: $-H_{20}$)

2-(Diethylaminopropanethiol can be prepared as follows:

A 10N aqueous solution of sodium hydroxide (25 cc) is added to a solution of 3-S-isothioureido-2-diethylaminopropane dihydrochloride (29.5 g) in distilled water (150 cc). The mixture is heated to 100° C. for 1 hour, cooled to 20° C., adjusted to pH 9 by adding a 12N aqueous solution of hydrochloric acid (8 cc), and is then extracted with ethyl ether (3×100 cc). The ether phases are combined, dried over potassium carbonate, filtered and then concentrated to dryness under reduced pressure (2.7 kPa) at 30° C. The mixture is purified by distillation. 2-Diethylamino-1-propanethiol (5.8 g) is obtained in the form of a colourless liquid. [B.p. (2.7 kPa)=78° C.]

1-S-Isothioureido-2-diethylaminopropane dihydrochloride can be prepared as follows:

Thiourea (16.7 g) is added to a solution of 1-chloro-2-diethylaminopropane hydrochloride (41 g) in dimethylformamide (200 cc). The mixture is heated to 100° C. for 30 minutes, and then cooled to 20° C. The white precipitate formed is collected by filtration, washed with dimethylformamide (3×20 cc) and then with ethyl ether (3×20 cc). 1-S-Isothioureido-2-diethylaminopropane dihydrochloride (29.6 g) is obtained in the form of white crystals melting at 247°-249° C.

1-Chloro-2-diethylaminopropane hydrochloride can be obtained as follows:

2-Diethylaminopropanol hydrochloride (45.2 g) is added over 15 minutes to thionyl chloride (100 cc) and the mixture is heated to 80° C. After 2 hours' stirring, excess thionyl chloride is distilled off and the residue is taken up with ethyl ether (200 cc). 1-Chloro-2-diethylaminopropane hydrochloride crystallizes out. After filtration, white crystals (48.2 g) melting at 112° C. are obtained.

2-Diethylaminopropanol hydrochloride can be obtained as follows:

A solution of ethyl 2-diethylaminopropionate (66 g) in ethyl ether (330 cc) is added slowly at 20° C. to a suspension of lithium aluminium hydride (10.6 g) in ethyl ether (1 liter) kept under nitrogen. The reaction is maintained for 5 hours at a temperature of 35° C., and the temperature is then lowered to 0° C. Water (12.4 cc), a 5N aqueous solution of sodium hydroxide (9.1 cc) and then water (41.3 cc) are then added dropwise at 0° C., the mixture is stirred for 30 minutes and is then filtered through sintered glass and is then washed with ethyl ether. The ether phase is dried over potassium carbonate, filtered and then concentrated to dryness under reduced pressure (2.7 kPa) at 30° C. A yellow liquid (43.8 g) is obtained and is dissolved in acetone (200 cc), to which a 4.5N solution (78 cc) of hydrogen chloride gas in ethyl ether is then added. 2-Diethylaminopropanol hydrochloride crystallizes out. After filtration, white crystals (45.2 g) melting at 97°-100° C. are obtained.

Ethyl 2-diethylaminopropionate can be obtained according to Braun et al., Beilstein, 61, 1425 (1928).

EXAMPLE 8

The method used is similar to that described in Example 2, but starting from 26-(2-diethylaminopropyl)thiopristinamycin $II_B$ (isomers A) (4 g), 98% meta-chloroperbenzoic acid (1.16 g) and solid sodium bicarbonate (1 g). After purification by "flash" chromatography [eluent: chloroform-methanol (93-7) by volume)] and concentrating fractions 21 to 48 to dryness under reduced pressure (2.7 kPa) at 30° C., 25-cc fractions being collected, 26-(2-diethylaminopropyl)sulphinylpristinamycin $II_B$ (isomers $A_2$) (2.69 g) is obtained in the form of a yellow powder which has characteristics identical to those of the product obtained in Example 7.

26-(2-Diethylaminopropyl)thiopristinamycin $II_B$ (isomer A) can be obtained by using a method similar to that described in Example 1, but starting from pristinamycin $II_A$ (15 g) and 2-diethylaminopropanethiol (4.62 g). After purification by "flash" chromatography [eluent: chloroform-methanol (90-10 by volume)] and concentrating fractions 27 to 52 to dryness under reduced pressure (2.7 kPa) at 30° C., 40-cc fractions being collected, a yellow solid (12 g) is obtained and stirred in ethyl ether (60 cc), filtered off and then dried. 26-(2-Diethylaminopropyl)thiopristinamycin $II_B$ (isomer A) (8.2 g) is obtained in the form of a light-yellow powder melting at about 122° C.

NMR spectrum:

1 to 1.15 (mt, ethyl-$C\underline{H}_3$ + $CH_3-C\underline{H}-N(C_2H_5)_2$)
|

1.70 (s, $-CH_3$ at 33)

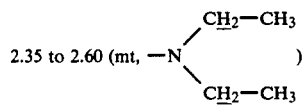
2.35 to 2.60 (mt, $-N\begin{array}{c}C\underline{H}_2-CH_3\\ \\ C\underline{H}_2-CH_3\end{array}$ )

2.50 to 3.10 (mt, $-SCH_2C\underline{H}-$)
|

2.75 (mt, $-H_4$)

2.89 and 3.05 (2dd ⎫
2.92 and 3.08 (2dd ⎬ ╲$CH_2$ at 15)
            ⎭ ╱

3.30 (mt ⎫
3.37 (mt ⎬ $-H_{26}$)
       ⎭

3.80 (s, ╲$CH_2$ at 17)
       ╱

4.69 (d ⎫
4.71 (d ⎬ $-H_{27}$)
     ⎭

5.45 (d, —H$_{13}$)

6.13 (d) 
6.14 (d) } —H$_{11}$)

6.4 to 6.60 (mt, \>NH at 8)

6.51 (dd) 
6.53 (dd) } —H$_5$)

8.09 (S, —H$_{20}$)

2-Diethylaminopropanethiol can be obtained as described earlier in Example 7.

EXAMPLE 9

The method used is similar to that described in Example 2 but starting from 26-(1-diethylamino-2-propyl)-thiopristinamycin II$_B$ (isomers A) (4.58 g), 98% meta-chloroperbenzoic acid (1.29 g) and solid sodium bicarbonate (1.14 g). After purification by "flash" chromatography [eluent: chloroform-methanol (97-3 by volume)], 20-cc fractions being collected, and concentrating, respectively, fractions 59 to 77 and fractions 79 to 97 under reduced pressure (2.7 kPa) at 30° C., there are obtained: from fractions 79 to 97, 26-(1-diethylamino-2-propyl)sulphinylpristinamycin II$_B$ (first isomer) (1.47 g) in the form of a light-yellow solid melting at about 132° C.

NMR spectrum:

1.02 (t, ethyl-CH$_3$)

1.34 (d, C$\underline{H}_3$—CH—CH$_2$N(C$_2$H$_5$)$_2$)

1.72 (s, —CH$_3$ at 33)

2.5 to 2.7 (mt, —CH$_2$—N\<CH$_2$— / CH$_2$—)

2.77 (mt, —H$_4$)

2.87 and 3.09 (2dd, \>CH$_2$ at 15)

2.97 (mt, —S—CH\< ) ↓ O 3.72 (mt, —H$_{26}$)

3.80 (s, \>CH at 17)

4.92 (mt, —H$_{27}$)
5.43 (d, —H$_{13}$)
6.15 (d, —H$_{11}$)

6.72 (dd, \>NH at 8)

8.06 (s, —H$_{20}$)

and from fractions 59 to 77, 26-(1-diethylamino-2-propyl)sulphinylpristinamycin II$_B$ (second isomer) (1.07 g) in the form of a light-yellow solid melting at about 128° C.

NMR spectrum: 1.72 (s, CH$_3$ at 33), 3.4 (mt, —H$_{26}$), 3.79 (s, CH$_2$ at 17), 4.74 (mt, —H$_{27}$), 5.48 (d, —H$_{13}$), 6.18 (d, —H$_{11}$), 6.80 (mf, \>NH at 8), 8.09 (s, —H$_{20}$).

26-(1-Diethylamino-2-propyl)thiopristinamycin II$_B$ (isomers A) can be obtained by using a method similar to that described in Example 1 but starting from pristinamycin II$_A$ (13 g) and 1-diethylamino-2-propanethiol (4 g). After purification by "flash" chromatography [eluent: chloroform-methanol (90-10 by volume)] and concentrating fractions 46 to 55 to dryness under reduced pressure (2.7 kPa) at 30° C., 50-cc fractions being collected, a pale yellow solid (8 g) is obtained and recrystallized from acetonitrile (30 cc). After filtration and drying, 26-(2-diethylamino-2-propyl)thiopristinamycin II$_B$ (isomers A) (5.91 g) is obtained in the form of white crystals melting at 136° C.

NMR spectrum:

0.9 to 1.10 (mt, —N(CH$_2$C$\underline{H}_3$)$_2$)

1.33 to 1.37 (2d, C$\underline{H}_3$—CH—CH$_2$N\< )

1.7 (s, —CH$_3$ at 33)

2.4 to 2.65 (mt, —CH$_2$N\<CH$_2$— / CH$_2$—)

2.76 (mt, —H$_4$)

3 (mt, —S—CH\< )

2.9 and 3.1 (2dd, \>CH$_2$ at 15)

3.52 (mt, —H$_{26}$)

3.81 (s, \>CH$_2$ at 17)

4.78 (mt, —H$_{27}$)
5.46 (d, —H$_{13}$)
6.14 (d, —H$_{11}$)

6.40 (mt, \>NH at 8)

-continued
8.09 and 8.10 (2s, —H$_{20}$)

1-Diethylamino-2-propanethiol can be obtained according to the method described by R. T. Wragg, J. Chem. Soc. (C), 2087 (1969).

EXAMPLE 10

A method similar to that described in Example 2 is used, but starting from 26-[(2R)-2-dimethylaminobutyl]-thiopristinamycin II$_B$ (isomer A) (1.7 g), sodium bicarbonate (0.50 g) and 98% meta-chloroperbenzoic acid (0.45 g). After purification by "flash" chromatography [eluent: ethyl actate-methanol (85–15 by volume)] and concentrating fractions 35 to 58 to dryness under reduced pressure (2.7 kPa) at 30° C., a white solid (1.1 g) is obtained which is stirred in ethyl ether (30 cc). After filtration and drying, 26-[(2R)-2-dimethylaminobutyl]-sulphinylpristinamycin II$_B$ (isomer A$_2$) (0.95 g) is obtained in the form of a white solid melting at about 126° C.

NMR spectrum:

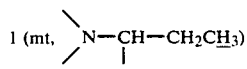

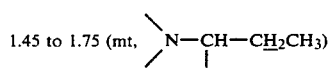

1.78 (s, —CH$_3$ at 33)

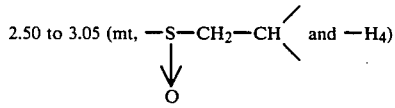

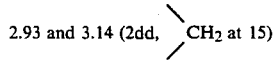

3.31 (mt, —H$_{26}$)

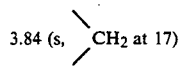

4.84 (d, —H$_{27}$)
5.51 (d, —H$_{13}$)
6.19 (d, —H$_{11}$)

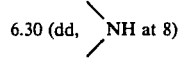

8.15 (s, —H$_{20}$)

26-[(2R)-2-Dimethylaminobutyl]thiopristinamycin II$_B$ (isomer A) can be obtained by using a method similar to that described in Example 1 but starting from pristinamycin II$_A$ (8 g) and (2R)-2-dimethylaminobutanethiol. After purification by "flash" chromatography [eluent: dichloromethane-methanol (90-10 by volume)] and concentrating fractions 36 to 55 to dryness under reduced pressure (2.7 kPa) at 30° C., 26-[((2R)-2-dimethylaminobutyl]thiopristinamycin II$_B$ (isomer A) (3 g) is obtained in the form of a light-yellow solid melting at about 120° C.

Crystallization of this product (0.9 g) from acetonitrile (5 cc) produces, after separation by filtration, 26-[(2R)-2-dimethylaminobutyl]thiopristinamycin II$_B$ (isomer A) (0.2 g) in the form of white crystals melting at 122° C.

NMR spectrum:

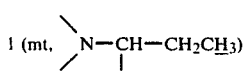

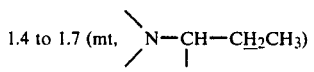

1.72 (s, —CH$_3$ at 33)
2.30 (s, —N(CH$_3$)$_2$)

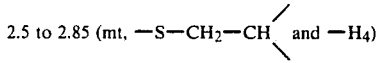

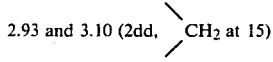

3.34 (broad d, —H$_{26}$)

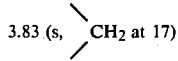

4.76 (broad s, —H$_{27}$)
5.48 (d, —H$_{13}$)
6.14 (d, —H$_{11}$)

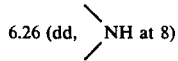

8.13 (s, —H$_{20}$)

(R)-2-Dimethylaminobutanethiol can be obtained using a method similar to that described below in Example 11, starting from triphenylphosphine (52.4 g), diisopropyl azodicarboxylate (40 cc), (R)-2-dimethylaminobutanol (12 g) and thiolacetic acid (15.2 cc) (in this case, the intermediate thioester is hydrolysed directly during the chromatography on silica gel).

After purification by "flash" chromatography [eluent: dichloromethane: 1000 cc, then dichloromethane-methanol (85-15 by volume): 2000 cc, then dichloromethane-methanol (80-20 by volume): 4000 cc], 100-cc fractions being collected, and concentrating fractions 42 to 60 to dryness under reduced pressure, a yellow oil (14 g) is obtained, which is purified by distillation. In this manner, (R)-2-dimethylaminobutanethiol (2.4 g) is obtained in the form of a colourless liquid. [B.p. (4 kPa)=70°-75° C.].

(R)-2-Dimethylamino-1-butanol can be obtained by a method identical to that described by M. Wenghoefer et al., J. Heterocycl. Chem., 7(6), 1407 (1970).

EXAMPLE 11

26-[(2S)-2-Dimethylamino-3-phenylpropyl]thiopristinamycin II$_B$ (isomer A) (2.67 g), sodium bicarbonate (0.7 g) and 98% meta-chloroperbenzoic acid (0.7 g), after purification by "flash" chromatograhy [eluent: chloroform-methanol (90-10 by volume)], 20-cc fractions being collected, and concentrating fractions 19 to 23 to dryness under reduced pressure (2.7 kPa) at 30° C., a light-yellow solid (1.3 g) is obtained, which is stirred in ethyl ether (50 cc), and separated off by filtration to give 26-[(2S)-2-dimethylamino-3-phenylpropyl]sulphinylpristinamycin II$_B$ (isomer A$_2$) (1.18 g) in the form of a light-yellow solid melting at about 150° C.

NMR spectrum (400 MHz, CDCl$_3$)

1.73 (s, —CH$_3$ at 33)

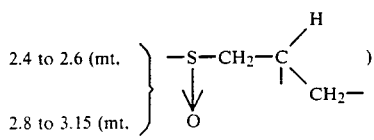

2.4 to 2.6 (mt, 2.8 to 3.15 (mt, 2.44 (s, —N(CH$_3$)$_2$)
2.77 (mt, —H$_4$)

2.89 and 3.1 (2dd, ⟩CH$_2$ at 15)

3.18 (mt, —H$_{26}$)

3.82 (s, ⟩CH$_2$ at 17)

4.68 (d, —H$_{27}$)
5.51 (d, —H$_{13}$)
6.19 (d, —H$_{11}$)

6.50 (dd, ⟩NH at 8)

7.18 (d, phenyl ortho-H)
7.23 (t, phenyl para-H)
7.31 (t, phenyl meta-H)
8.13 (s, —H$_{20}$)

An aqueous solution containing 1% of 26-[(2S)-2-dimethylamino-3-phenylpropyl]sulphinylpristinamycin II$_B$ (isomer A$_2$) is obtained with:

| product | 30 mg |
|---|---|
| 0.1 N hydrochloric acid | 0.45 cc |
| distilled water q.s. | 3 cc |

26-[(2S)-2-Dimethylamino-3-phenylpropyl]thiopristinamycin II$_B$ (isomer A) can be prepared by using a method similar to that described in Example 1 for the preparation of the starting material, but starting from pristinamycin II$_A$ (7.13 g) and (S)-2-dimethylamino-3-phenylpropanethiol (2.65 g) and after purification by "flash" chromatography [eluent: ethyl acetate-methanol (80-20) by volume)], 60-cc fractions being collected, and concentrating fractions 33 to 43 to dryness under reduced pressure (2.7 kPa) at 30° C., a light-yellow solid (4.6 g) is obtained which is stirred in ethyl ether (50 cc), filtered off and then dried under reduced pressure (90 Pa) at 45° C. In this manner, 26-[(2S)-2-dimethylamino-3-phenylpropane]thiopristinamycin II$_B$ (isomer A) (3.6 g) is obtained in the form of a pale yellow power melting at about 110° C.

NMR spectrum:

1.69 (s, —CH$_3$ at 33)

2.38 (s, —N(CH$_3$)$_2$)

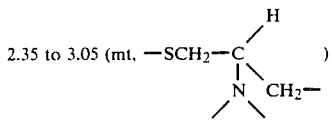

2.35 to 3.05 (mt, —SCH$_2$—C 2.73 (mt, —H$_4$)

2.89 and 3.10 (2dd, ⟩CH$_2$ at 15)

3.26 (broad d, —H$_{26}$)

3.81 (s, ⟩CH$_2$ at 17)

4.68 (broad s, —H$_{27}$)

5.47 (d, —H$_{13}$)

6.12 (d, —H$_{11}$)

6.27 (mf, ⟩NH at 8)

7.18 (d, phenyl ortho-H)

7.21 (t, phenyl para-H)

7.30 (t, phenyl meta-H)

8.11 (s, —H$_{20}$)

(S)-2-Dimethylamino-3-phenylpropanethiol can be prepared as follows:

Sodium methoxide (0.2 g) is added under a nitrogen atmosphere to (S)-2-dimethylamino-3-phenylpropanethiolacetate (20 g: crude) dissolved in methanol (50 cc) and the mixture is heated under reflux for 2 hours. The mixture is then concentrated to dryness under reduced pressure (2.7 kPa) at 30° C. to give a liquid which is purified by distillation. (S)-2-Dimethylamino-3-phenylpropanethiol (2.4 g) is obtained in the form of a colourless liquid [b.p. (14 Pa)=95° C.] which is used as such in the reaction which follows.

(S)-2-Dimethylamino-3-phenylpropanethiolacetate can be prepared as follows:

Triphenylphosphine (41.97 g) and tetrahydrofuran (310 cc) are added at 0° C. under a nitrogen atmosphere, and then diisopropyl azodicarboxylate (31.5 cc) is added dropwise and the mixture is left stirred for half an hour at 0° C. A mixture of (S)-2-dimethylamino-3-phenylpropanol (15 g) and of thiolacetic acid (11.44 cc) dissolved in tetrahydrofuran (160 cc) is added dropwise to the white suspension obtained. After being stirred for 1 hour at 0° C. and then for 1 hour 30 minutes at 25° C., the mixture is concentrated to dryness under reduced pressure (2.7 kPa) at 30° C. Methanol (190 cc) is added to the oil obtained, the white solid which precipitates is removed by filtration, and the filtrate is concentrated to dryness under reduced pressure (2.7 kPa) at 30° C. The residue is then stirred with isopropyl ether (200 cc), the white solid precipitated is again removed by filtration and the filtrate is concentrated to give a yellow oil (45 g), which is purified by "flash" chromatography [eluent: dichloromethane-methanol (90-10 by volume)], 100-cc fractions being collected. After concentrating fractions 37 to 55 to dryness under reduced pressure (2.7 kPa) at 30° C., (S)-2-dimethylamino-3-phenylpropanethiolacetate (10.4 g) is obtained in the form of an orange-yellow oil (containing triphenylphosphine oxide).

(S)-2-Dimethylamino-3-phenylpropanol can be prepared by using a method similar to that described by T. Hayashi et al., J. Org. Chem., 48, 2195 (1983).

EXAMPLE 12

By using a method similar to that described in Example 1, but starting from 26-[2-(1-pyrrolidinyl)ethyl]thiopristinamycin II$_B$ (90% isomer A), trifluoroacetic acid (1.47 cc), and meta-chloroperbenzoic acid (3.86 g), and after purification by "flash" chromatography [eluent: chloroform-methanol (85-15 by volume)], 30-cc fractions being collected, and concentrating fractions 18 to 25 to dryness under reduced pressure (2.7 kPa) at 30° C., 26-[2-(1-pyrrolidinyl)ethyl]sulphinylpristinamycin II$_B$ (isomers: 60% A$_1$, 25% A$_2$, 15% B$_1$) (3.9 g) is obtained in the form of a yellow power melting at about 175° C.

NMR spectrum (isomer A$_1$):

1.74 (s, —CH$_3$ at 33)

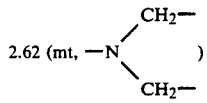
2.62 (mt, —N)

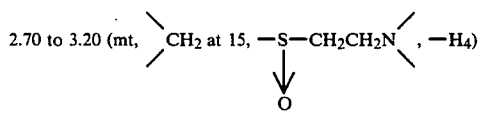
2.70 to 3.20 (mt, CH$_2$ at 15, —S—CH$_2$CH$_2$N, —H$_4$)

3.81 (s, CH$_2$ at 17)

5.28 (broad s, —H$_{27}$)
5.45 (d, —H$_{13}$)
6.14 (d, —H$_{11}$)

6.58 (mt, NH at 8)

8.12 (s, —H$_{20}$)

After concentrating fractions 26 to 43 to dryness under reduced pressure (2.7 kPa) at 30° C., 26-[2-(1-pyrrolidinyl)ethyl]sulphinylpristinamycin II$_B$ (75% isomer A$_2$, 5% isomer A$_1$, 10% isomer B$_1$, 10% isomer B$_2$) (4.36 g) is obtained in the form of a yellow powder melting at about 145° C.

NMR spectrum (isomer A$_2$):

1.76 (s, —CH$_3$ at 33)

1.82 (m, CH$_2$ at 3- and 4- of pyrrolidinyl)

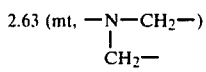
2.63 (mt, —N—CH$_2$—)
       |
       CH$_2$—

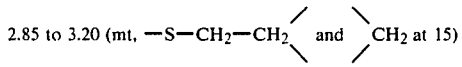
2.85 to 3.20 (mt, —S—CH$_2$—CH$_2$ and CH$_2$ at 15)

3.82 (s, CH$_2$ at 17)

4.84 (dd, —H$_3$ + d, —H$_{27}$)
5.51 (d, —H$_{13}$)
6.18 (d, —H$_{11}$)

6.47 (mt, NH at 8)

8.13 (s, —H$_{20}$)

26-[2-(1-Pyrrolidinyl)ethyl]thiopristinamycin II$_B$ can be prepared as follows:

By using a method similar to that described in Example 3 but starting from pristinamycin II$_A$ (5.25 g) and 2-(1-pyrrolidinyl)ethanethiol (1.7 g), and after purification by "flash" chromatography [eluent: chloroform-methanol (95-5by volume)] of 2-(1-pyrrolidinyl)ethanethiol, and after purification by "flash" chromatography [eluent: chloroform-methanol (95-5 by volume)] and concentrating fractions 19 to 60 to dryness under reduced pressure (2.7 kPa) at 30° C., 26-[2-(1-pyrrolidinyl)ethyl]thiopristinamycin II$_B$ (3.9 g) is obtained in the form of a yellow powder melting about 115° C.

NMR spectrum:

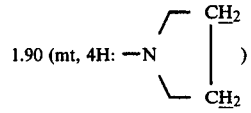
1.90 (mt, 4H: —N)

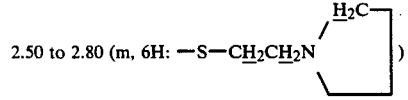
2.50 to 2.80 (m, 6H: —S—CH$_2$CH$_2$N)

3.40 (d, 1H: —H$_{26}$)
4.75 (d, 1H: —H$_{27}$)
8.10 (s, 1H, —H$_{20}$)

2-(1-Pyrrolidnyl)ethanethiol can be prepared according to the method described by J. W. Haeffele and R. W. Broge, Proc. Sci. Toilet Goods Assoc. 32, 52 (1959) [Chem. Abstr. 54, 17234e (1960)].

EXAMPLE 13

By using a method similar to that described in Example 1, but starting from 26-(2-piperidinoethyl)thiopristinamycin II$_B$ (isomer A) (6 g), trifluoroacetic acid (0.69 cc) and 85% meta-chloroperbenzoic acid (1.82 g), after purification by "flash" chromatography [eluent: chloroform-methanol (85-15 by volume)], 20-cc fractions being collected and concentrating fractions 52 to 105 to dryness under reduced pressure (2.7 kPa) at 30° C., a yellow solid (4.7 g) is obtained, which is again purified by "flash" chromatography [eluent: chloroform-methanol (85-15 by volume)], 5-cc fractions being collected. After concentrating fractions 92 to 99 under reduced pressure (2.7 kPa) at 30° C., a yellow solid (1.83 g) is obtained, which is stirred in ethyl ether (20 cc), separated off by filtration, and then dried under reduced pressure (90 Pa) at 30° C. In this manner, 26-(2-piperidinoethyl)thiopristinamycin II$_B$ (isomers: 90% A$_2$, 10% A$_1$) (1.51 g) is obtained in the form of a yellow powder melting at about 162° C.

NMR spectrum (400 MHz, CDCl$_3$)

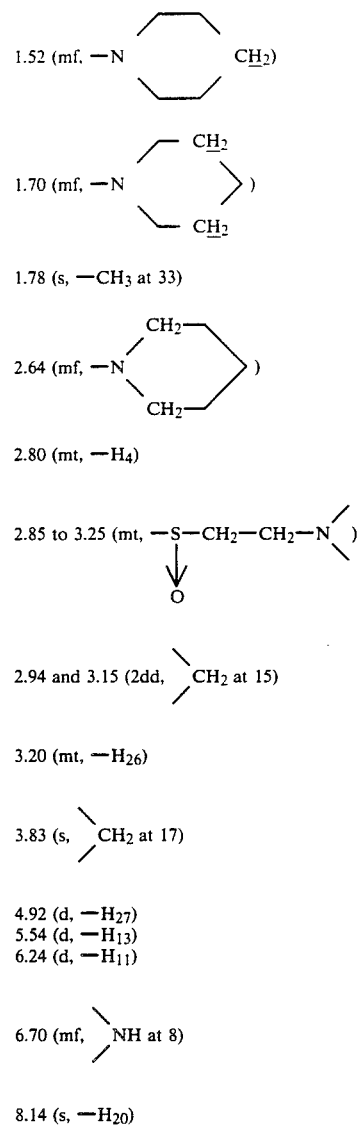

After concentrating fractions 100 to 140 to dryness under reduced pressure (2.7 kPa) at 30° C., a yellow solid (2.11 g) is obtained, which is stirred in ethyl ether (20 cc), separated off by filtration and then dried under reduced pressure (90 Pa) at 30° C. 26-(2-Piperidinoethyl)thiopristinamycin II$_B$ (isomers: 50% A$_1$, 50% A$_2$) (1.75 g) is obtained in the form of a yellow powder melting at about 152° C.

NMR spectrum (400 MHz, CDCl$_3$), 1.74 (s, —CH$_3$ at 33 isomer A$_1$), 1.78 (s, —CH$_3$ at 33 isomer A$_2$), 3.20 (mt, —H$_{26}$ isomer A$_2$), 3.46 (mt, —H$_{26}$ isomer A$_1$), 3.82 (borderline AB, >CH$_2$ at 17 isomer A$_1$), 3.83 (s, >CH$_2$ at 17 isomer A$_2$), 4.90 (d, —H$_{27}$ isomer A$_2$), 5.30 (s, —H$_{27}$ isomer A$_1$), 5.52 (d, —H$_{13}$ isomer A$_1$), 5.54 (d, —H$_{13}$ isomer A$_2$), 6.60 (dd, —H$_5$ isomer A$_2$), 6.70 (dd, —H$_5$ isomer A$_1$). 8.14 (s, —H$_{20}$, isomers A$_2$ and A$_1$)

26-(2-Piperidinoethyl)thiopristinamycin II$_B$ (isomer A) can be obtained as follows:

By using a method similar to that described in Example 1, but starting from pristinamycin II$_A$ (11.8 g) and 2-piperidinoethanethiol (3.58 g), and after purification by "flash" chromatography [eluent: chloroform-methanol (85-15 by volume)], 60-cc fractions being collected, and concentrating fractions 24 to 31 to dryness under reduced pressure (2.7 kPa) at 30° C., 26-(2-piperidinoethyl)thiopristinamycin II$_B$ (isomer A) (8.3 g) is obtained in the form of a light-yellow powder melting at about 120° C.

NMR spectrum:

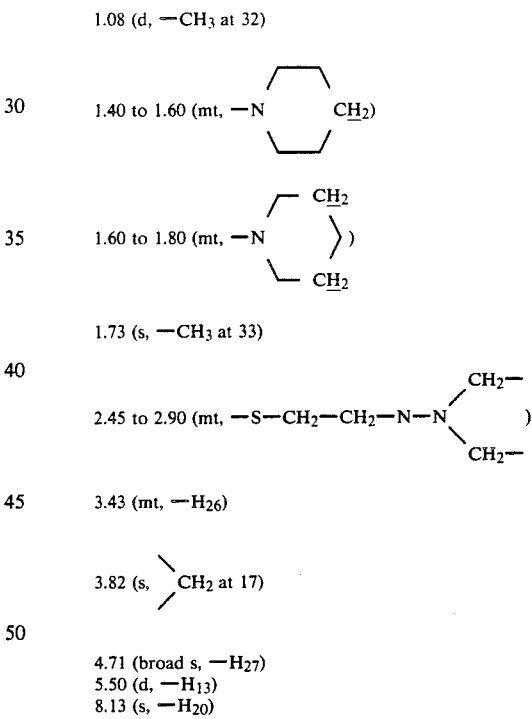

2-Piperidinoethanethiol can be obtained by a method identical to that described by D. D. Reynolds, D. L. Fields and D. J. Johnson, J. Org. Chem., 26, 5125 (1961).

EXAMPLE 14

By using a method similar to that described in Example 2, but starting from 26-[2-(1-imidazolyl)ethyl]thiopristinamycin II$_B$ (isomers: 85% A, 15% B) (3.2 g), sodium bicarbonate (1 g) and 98% meta-chloroperbenzoic acid (0.93 g), after purification by "flash" chromatography [eluent: chloroform-methanol (90-10 by volume)], 25-cc fractions being collected, and concentrating fractions 29 to 49 to dryness under reduced pressure (2.7 kPa) at 30° C., a yellow solid (1.4 g) is obtained. The solid obtained is purified again by "flash" chromatography [eluent: chloroform-methanol (90-10 by volume)], 10-cc fractions being collected. After concentrating fractions 47 to 55 to dryness under reduced pressure (2.7 kPa) at 30° C., a light-yellow solid (0.62 g) is obtained, which is stirred in ethyl ether (20 cc), separated off by filtration and then dried under reduced pressure (90 Pa) at 40° C. In this manner, 26-[2-(1-imidazolyl)ethyl)]sulphinylpristinamycin $II_B$ (isomer $A_2$) (0.6 g) is obtained in the form of a yellow solid melting at about 170° C.

NMR spectrum (400 MHz, CDCl$_3$)

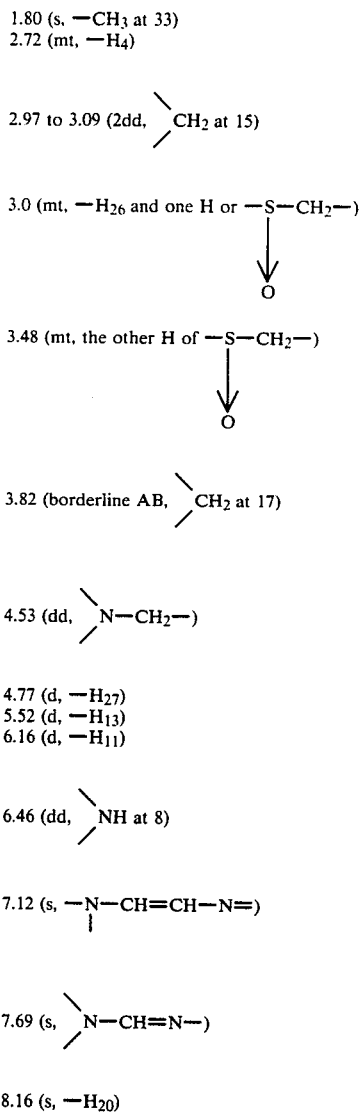

26-[2-(1-imidazolyl)ethyl]thiopristinamycin $II_B$ can be prepared by using a method similar to that described in Example 3, but starting from pristinamycin $II_A$ (14.35 g) and 2-(1-imidazolyl)ethanethiol (3.5 g), after stirring at 20° C. for 18 hours followed by purification by "flash" chromatography [eluent: ethyl acetate-methanol (80-20 by volume)] and concentrating fractions 34 to 59 to dryness under reduced pressure (2.7 kPa) at 30° C.; a yellow solid is obtained, which is stirred in ethyl ether (60 cc) and then separated off by filtration, to give 26-[2-(1-imidazolyl)ethyl]thiopristinamycin $II_B$ (isomers: 85% A, 15% B) (10.9 g) in the form of a yellow solid melting at about 160° C.

NMR spectrum: 1.53 (s, —CH$_3$ at 33 of B), 1.73 (s, —CH$_3$ at 33 of A), 2.74 (mt, —H$_4$ of A), 2.86 and 3.14 (2 dd, >CH$_2$ at 15 of A), 2.85 to 3.05 (mt, —SCH$_2$—), 3.11 (mt, —H$_{26}$ of A), 3.32 (mt, —H$_{26}$ of B), 3.82 (borderline AB, >CH$_2$ at 17 of A), 4.15 to 4.30 (mt, —CH$_2$N>), 4.58 (d, —H$_{27}$ of B), 4.68 (fine d, —H$_{27}$ of A), 5.44 (d, —H$_{13}$ of A), 6.16 (d, —H$_{11}$ of A), 6.83 (dd, >NH at 8 of A), 6.97 and 7.08 (2s, >N—CH=CHN< of B), 7.01 and 7.10 (2s, >N—CH=CHN< of A), 7.54 (s, >N—CH=N— of B), 7.61 (s, >N—CH=N— of A), 7.64 (mt, >NH at 8 of B), 7.82 (s, —H$_{20}$ of B), 8.09 (s, —H$_{20}$ of A).

2-(1-Imidazolyl)ethanethiol can be prepared by a method similar to that described in Example 11 for the preparation of the starting material, but starting from 2-(1-imidazolyl)ethanethiolacetate (21 g) and sodium methoxide (0.5 g). After purification by distillation, 2-(1-imidazolyl)ethanethiol (2.3 g) is obtained in the form of an oil [b.p. (20 Pa)=99.5° C.].

2-(1-Imidazolyl)ethanethiolacetate can be prepared by a method similar to that described in Example 11 for the preparation of the starting material, but starting from 2-(1-imidazolyl)ethanol (15 g), triphenylphosphine (70.2 g), diisopropyl azodicarboxylate (55.8 cc) and thiolacetic acid (21 cc). After purification by "flash" chromatography [eluent: methylene chloride (1500 c), followed by ethyl acetate-methanol (80-20 by volume)], 100-cc fractions being collected, and concentrating fractions 21 to 35 to dryness under reduced pressure (2.7 kPa) at 30° C., 2-(1-imidazolyl)ethylthioacetate (21.14 g) is obtained in the form of an orange-yellow oil which is used without further purification.

2-(1-Imidazolyl)ethanol can be prepared by a method similar to that described by J. Geibel et al., J. Am. Chem. Soc., 100, 3575 (1978).

EXAMPLE 15

By using a method similar to that described in Example 2, but starting from 26-(2-morpholinoethyl)thiopristinamycin $II_B$ (isomer A) (5.5 g), sodium bicarbonate (1.3 g), and 98% meta-chloroperbenzoic acid (1.4 g), after extraction of the reaction mixture, drying of the organic phase over magnesium sulphate, filtering and concentrating to dryness under reduced pressure (2.7 kPa) at 30° C., a light-yellow solid is obtained, which is stirred in isopropyl ether (100 cc), separated off by filtration, and then dried under reduced pressure (90 Pa) at 35° C. In this manner, 26-(2-morpholinoethyl)sulphinylpristinamycin $II_B$ (isomer $A_2$) (4.8 g) is obtained in the form of a light-yellow solid melting at about 126° C.

NMR spectrum:

1.77 (s, —CH$_3$ at 33)

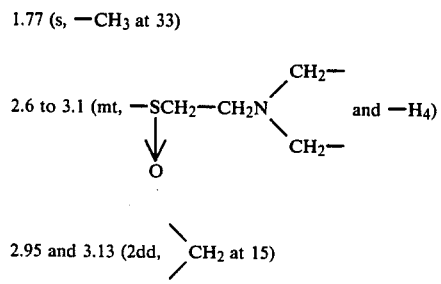

2.95 and 3.13 (2dd, >CH$_2$ at 15)

-continued 3.20 (mt, —H$_{26}$)

3.78 (mt, —CH$_2$—O—CH$_2$—)

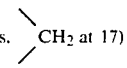
3.81 (s, >CH$_2$ at 17)

4.85 (mt, —H$_{27}$)
5.53 (d, —H$_{13}$)
6.20 (d, —H$_{11}$)

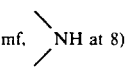
6.53 (mf, >NH at 8)

8.14 (s, —H$_{20}$)

26-(2-Morpholinoethyl)thiopristinamycin II$_B$ (isomer A) can be obtained by a method similar to that described in Example 1, but starting from pristinamycin II$_A$ (15 g) and 2-morpholinoethanethiol (6.3 g). After purification by "flash" chromatography [eluent: ethyl acetate-methanol (75-25 by volume)], 30-cc fractions being collected, and concentrating fractions 35 to 49 to dryness under reduced pressure (2.7 kPa) at 30° C., a beige solid (11 g) is obtained which is crystallized from acetonitrile (120 cc). In this manner, 26-(2-morpholinoethyl)thiopristinamycin II$_B$ (isomer A) (5.7 g) is obtained in the form of white crystals melting at 132° C.

NMR spectrum:

1.73 (s, —CH$_3$ at 33)

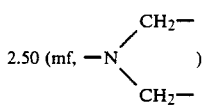
2.50 (mf, —N<CH$_2$—/CH$_2$—)

2.6 to 2.9 (mt, —H$_4$)

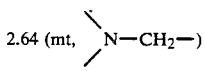
2.64 (mt, >N—CH$_2$—)

2.79 (mt, —SCH$_2$—)

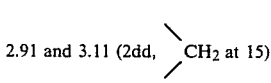
2.91 and 3.11 (2dd, >CH$_2$ at 15)

3.37 (broad d, —H$_{26}$)

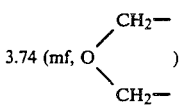
3.74 (mf, O<CH$_2$—/CH$_2$—)

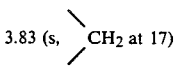
3.83 (s, >CH$_2$ at 17)

4.74 (broad s, —H$_{27}$)
5.45 (d, —H$_{13}$)
6.13 (d, —H$_{11}$)

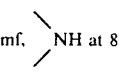
6.28 (mf, >NH at 8)

8.13 (s, —H$_{20}$)

2-Morpholinoethanethiol can be prepared by a method similar to that described by D. D. Reynolds et al., J. Org. Chem., 26, 5125 (1961).

EXAMPLE 16

By using a method similar to that described in Example 1, but starting from 26-(2-butylaminoethyl)thiopristinamycin II$_B$ (80% isomer A, 20% isomer B) (5.8 g), trifluoroacetic acid (0.68 cc) and meta-chloroperbenzoic acid (1.8 g), and after purification by "flash" chromatography [eluent: chloroform-methanol (90-10 by volume)], 15-cc fractions being collected, and concentrating fractions 9 to 15 dryness under reduced pressure (2.7 kPa) at 30° C., 26-(2-butylaminoethyl)sulphinylpristinamycin II$_B$ (70% isomer A$_2$, 15% isomer B$_1$, 15% isomer B$_2$) (1.7 g) is obtained in the form of a yellow powder melting at about 140° C.

NMR spectrum (isomer A$_2$):

0.85 to 1.00 (mt, —CH$_3$ at 31 and 30 + chain —CH$_3$)

1.34 (mt, —C$\underline{H}_2$CH$_3$)

1.48 (mt, —CH$_2$C$\underline{H}_2$CH$_2$CH$_3$)

1.75 (s, —CH$_3$ at 33)

2.50 to 3.30 (mt, —H$_{26}$, >CH$_2$ at 2,

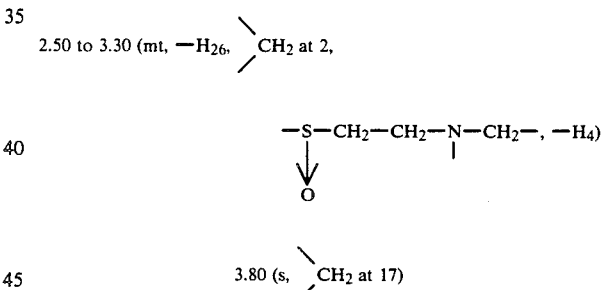
—S—CH$_2$—CH$_2$—N—CH$_2$—, —H$_4$)
↓
O

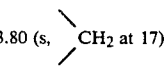
3.80 (s, >CH$_2$ at 17)

4.80 (d, —H$_{27}$)
5.50 (d, —H$_{13}$)
6.17 (d, —H$_{11}$)

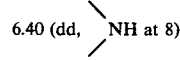
6.40 (dd, >NH at 8)

8.12 (s, —H$_{20}$)

After concentrating fractions 18 to 24 to dryness under reduced pressure (2.7 kPa) at 30° C., 26-(2-butylaminoethyl)sulphinylpristinamycin II$_B$ (85% isomer A$_1$, 15% isomer B$_1$) (0.5 g) is obtained in the form of a yellow powder melting at about 170° C.

NMR spectrum (isomer A$_1$):

0.85 to 1.00 (mt, —CH$_3$ at 31, 30 and chain —CH$_3$)

1.33 (mt, —C$\underline{H}_2$CH$_3$)

1.47 (mt, —CH$_2$CH$_2$CH$_2$CH$_3$)

1.71 (s, —CH$_3$ at 33)

2.50 to 3.25 (mt, 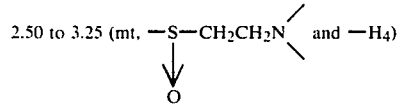 and —H$_4$)

3.79 (borderline AB, 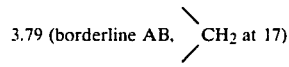 CH$_2$ at 17)

5.26 (d, —H$_{27}$)

5.44 (d, —H$_{13}$)

6.13 (d, —H$_{11}$)

6.62 (mt, 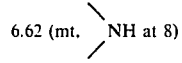 NH at 8)

8.10 (s, —H$_{20}$)

26-(2-Butylaminoethyl)thiopristinamycin II$_B$ (80% isomer A, 20% isomer B) can be prepared as described below in Example 17.

EXAMPLE 17

By using a method similar to that described in Example 1, but starting from 26-(2-butylaminoethyl)thiopristinamycin II$_B$ (isomer B) (3.15 g), trifluoroacetic acid (0.37 cc) and meta-chloroperbenzoic acid (0.97 g), and after purification by "flash" chromatography [eluent: chloroform-methanol (90-10 by volume)], 15-cc fractions being collected, and concentrating fractions 18 to 35 to dryness under reduced pressure (2.7 kPa) at 30° C., 26-(2-butylaminoethyl)sulphinylpristinamycin II$_B$ (65% isomer B$_1$, 35% isomer B$_2$) (1.18 g) is obtained in the form of a yellow powder melting at about 140° C.

NMR spectrum:

0.90 to 1.05 (mt, —CH$_3$ at 30 and 31 and chain —CH$_3$ of B$_1$ and B$_2$)

1.40 (mt, —CH$_2$CH$_3$ of B$_1$ and B$_2$)

1.50 (mt, —CH$_2$CH$_2$CH$_2$CH$_3$ of B$_1$ and B$_2$)

1.57 (s, —CH$_3$ at 33 of B$_1$ and B$_2$)

2.63 (t, 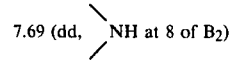 NCH$_2$CH$_2$CH$_2$CH$_3$ of B$_1$ and B$_2$)

2.65 to 3.30 (mt, 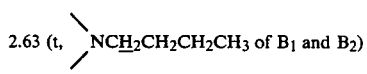, CH$_2$ at 15,

—H$_4$ of B$_1$ and B$_2$)

3.74 and 3.92 (2d, 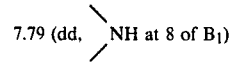 CH$_2$ at 17 of B$_1$)

3.73 and 3.94 (2d, 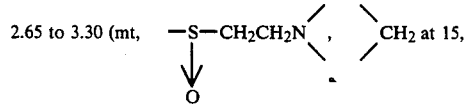 CH$_2$ at 17 of B$_2$)

4.78 (d, —H$_{27}$ of B$_2$)

4.75 to 4.90 (mt, —H$_{13}$ and —H$_{14}$ of B$_1$ and B$_2$)

5.27 (d, —H$_{27}$ of B$_1$)

5.70 (2d, —H$_{11}$ of B$_1$ and B$_2$)

7.69 (dd, NH at 8 of B$_2$)

7.79 (dd, NH at 8 of B$_1$)

7.84 (s, —H$_{20}$ of B$_2$)

7.85 (s, —H$_{20}$ of B$_1$)

By using a method similar to that described in Example 3, but starting from pristinamycin II$_A$ (25 g) and 2-butylaminoethanethiol (6.34 g), and after purification by "flash" chromatography [eluent: chloroform-methanol (90-10 by volume)], 60-cc fractions being collected, and concentrating fractions 12 to 15 to dryness under reduced pressure (2.7 kPa) at 30° C., 26-(2-butylaminoethyl)thiopristinamycin II$_B$ (isomer B) (3.15 g) is obtained in the form of a yellow powder melting at about 110° C. After concentrating fractions 15 to 25 to dryness under reduced pressure (2.7 kPa) at 30° C., 26-(2-butylaminoethyl)thiopristinamycin II$_B$ (80% isomer A, 20% isomer B) (5.89 g) is obtained.

EXAMPLE 18

By using a method similar to that described in Example 1, but starting from 26-(2-decylaminoethyl)thiopristinamycin II$_B$ (8.6 g), trifluoroacetic acid (0.9 cc) and meta-chloroperbenzoic acid (2.35 g) and after purification by "flash" chromatography [eluent: chloroform-methanol (90-10 by volume)], 40-cc fractions being collected, and concentrating fractions 12 to 15 to dryness under reduced pressure (2.7 kPa) at 30° C., 26-(2-decylaminoethyl)sulphinylpristinamycin II$_B$ (80% isomer A$_2$) (1.5 g) is obtained in the form of a yellow powder melting at about 128° C.

NMR spectrum: 0.88 (t, —(CH$_2$)$_9$—CH$_3$), 1.30 ([m, (>CH$_2$)$_8$], 1.50 [m(>CH$_2$)$_8$], 1.77 (s, —CH$_3$ at 33), 4.81 (d, —H$_{27}$), 5.51 (d, —H$_{13}$), 6.19 (d, —H$_{11}$), 6.53 (mt, >NH at 8), 8.13 (s, —H$_{20}$).

After concentrating fractions 15 to 19 to dryness under reduced pressure (2.7 kPa) at 30° C., 26-(2-decylaminoethyl)sulphinylpristinamycin II$_B$ (mixture of isomers) (2.51 g) is obtained in the form of a yellow powder melting at about 124° C.

NMR spectrum (mixture of isomers: 50% type A$_2$, 15% A$_1$, 20% B$_1$ and 15% B$_2$), 1.54 (s, —CH$_3$ at 33 of B$_1$ and B$_2$), 3.72 and 3.88 (2 d, >CH$_2$ at 17 of B$_1$), 3.70 and 3.92 (2d, >CH$_2$ at 17 of B$_2$), 4.75 (d, —H$_{27}$ of B$_2$), 5.25 (d, —H$_{27}$ of B$_1$), 7.67 (dd, >NH at 8 of B$_2$), 7.77 (dd, >NH at 8 of B$_1$), 7.81 (s, —H$_{20}$ of B$_1$ and B$_2$), (characteristic peaks of isomers A₂ and A₁, identical to those mentioned above and below, respectively).

An aqueous solution containing 1% of 26-(2-decylaminoethyl)sulphinylpristinamycin $II_B$ in the form of hydrochloride is obtained with:

| | |
|---|---|
| 26-(2-decylaminoethyl)sulphinylpristinamycin $II_B$ | 15 mg |
| 0.1 N hydrochloric acid | 0.2 cc |
| distilled water q.s. | 1.5 cc. |

After concentrating fractions 20 to 24 to dryness under reduced pressure (2.7 kPa) at 30° C., 26-(2-decylaminoethyl)sulphinylpristinamycin $II_B$ (isomers: 60% $A_1$, 20% $A_2$, 20% $B_1$) (1.12 g) is obtained in the form of a yellow powder melting at about 136° C.

NMR spectrum (isomer $A_1$):

2.50 to 3.20 (mt, \>CH₂ at 15, —H₄ and

—S—CH₂CH₂—N—CH₂—)
 ↓    |
 O 3.82 (borderline AB, \>CH₂ at 17)

5.27 (d, —H₂₇)
5.46 (d, —H₁₃)
6.15 (d, —H₁₁)

6.62 (mt, \>NH at 8)

8.12 (s, —H₂₀)

26-(2-Decylaminoethyl)thiopristinamycin $II_B$ can be prepared as follows:

By using a method similar to that described in Example 3, but starting from pristinamycin $II_A$ (5.25 g) and 2-decylaminoethanethiol (3.26 g), and after purification by "flash" chromatography [eluent: methylene chloride-methanol (95-5 by volume)], and concentrating fractions 20 to 43 to dryness under reduced pressure (2.7 kPa) at 30° C., 26-(2-decylaminoethyl)thiopristinamycin $II_B$ (1.2 g) is obtained in the form of a yellow powder melting at about 80° C.

NMR spectrum (70-30 mixture of A and B isomers):

0.88 (t, —CH₃)

1.30 }
1.53 } (mt, —(CH₂)₈—)

1.54 (s, —CH₃ at 33 of B)
1.72 (s, —CH₃ at 33 of A)

2.6 to 3 (mt, —SCH₂—CH₂—N—CH₂—)
                       |

3.38 (broad d, —H₂₆ of A)
3.50 (mt, —H₂₆ of B)
4.64 (d, J = 3.5, —H₂₇ of B)
4.72 (broad s, —H₂₇ of A)

-continued
7.80 (s, —H₂₀ of B)
8.12 (s, —H₂₀ of A)

EXAMPLE 19

By using a method similar to that described in Example 1, starting from 26-(2-cyclohexylaminoethyl)sulphinylpristinamycin $II_B$ (isomers: 80% A, 20% B) (4.4 g), trifluoroacetic acid (0.5 cc) and meta-chloroperbenzoic acid (1.15 g), and after purification by "flash" chromatography [eluent: chloroform-methanol (90-10 by volume)], 40-cc fractions being collected, and concentrating fractions 24 to 29 to dryness under reduced pressure (2.7 kPa) at 30° C., 26-(2-cyclohexylaminoethyl)sulphinylpristinamycin $II_B$ (90% isomer $A_2$) (0.38 g) is obtained in the form of a light-yellow powder melting at about 166° C.

NMR spectrum:

1.05 to 1.35 [mt, cyclohexyl \>CH₂ (partly)]

1.77 (s, —CH₃ at 33)

1.55 to 2.25 [mt, \>CH₂ at 25, —H₂₉ and cyclohexyl \>CH₂ (partly)]

2.45 to 3.35 (mt, —H₂₆, \>CH₂ at 15, —H₄ and

—S—CH₂CH₂N—CH\< )
 ↓    |
 O 3.82 (s, \>CH₂ at 17)

4.82 (d, —H₂₇)
5.52 (d, —H₁₃)
6.19 (d, —H₁₁)

6.38 (dd, \>NH at 8)

8.14 (s, —H₂₀)

26-(2-Cyclohexylaminoethyl)thiopristinamycin $II_B$ can be obtained as follows:

By using a method similar to that described in Example 3, but starting from pristinamycin $II_A$ (5.25 g) and 2-cyclohexylaminoethanethiol (3.6 g), and after purification by "flash" chromatography [eluent: chloroform-methanol (93-7 by volume)] and concentrating fractions 7 to 18 to dryness under reduced pressure (2.7 kPa) at 30° C., 26-(2-cyclohexylaminoethyl)thiopristinamycin II$_B$ (1.7 g) is obtained in the form of a beige powder melting at about 120° C.

NMR spectrum: 1 to 1.4 [mt, cyclohexyl >CH$_2$ (partly)], 1.54 (s, —CH$_3$ at 33 isomer B), 1.73 (s, —CH$_3$ at 33 isomer A), 1.6 to 2 [mt, cyclohexyl >CH$_2$ (partly)], 2.80 (mt, >NCH$_2$—), 2.93 (t, —SCH$_2$—), 3.36 (broad d, —H$_{26}$ isomer A), 3.50 (mt, —H$_{26}$ isomer B), 4.64 (d, J=3, —H$_{27}$ isomer B), 4.72 (broad s, —H$_{27}$ isomer A), 6.50 (mt, —NH$_8$ isomer A), 7.75 (mt, —NH$_8$ isomer B), 7.80 (s, —H$_{20}$ isomer B), 8.12 (s, —H$_{20}$ isomer A).

2-Cyclohexylaminoethanethiol can be prepared according to the method described by D. D. Reynolds, M. K. Massad, D. L. Fields and D. L. Johnson, J. Org. Chem. 26, 5109 (1961).

EXAMPLE 20

By using a method similar to that described in Example 2, but starting from 26-(N-cyclohexyl-N-methyl-2-aminoethyl)thiopristinamycin II$_B$ (isomers: 80% A, 20% B) (5 g), sodium bicarbonate (1.17 g) and 98% metachloroperbenzoic acid (1.2 g), after purification by "flash" chromatography [eluent: dichloromethane-methanol (80-20 by volume)], 30-cc fractions being collected, and concentrating fractions 40 to 60 to dryness under reduced pressure (2.7 kPa) at 30° C., a yellow solid (3.5 g) is obtained, which is purified again by "flash" chromatography [eluent: ethyl acetate-methanol (80-20 by volume)], 25-cc fractions being collected. After concentrating fractions 11 to 18 to dryness under reduced pressure (2.7 kPa) at 30° C., a yellow solid (1.2 g) is obtained, which is stirred in ethyl ether (30 cc), separated off by filtration and then dried under reduced pressure (90 Pa) at 35° C. In this manner, 26-(N-cyclohexyl-N-methyl-2-aminoethyl)sulphinyl-pristinamycin II$_B$ (isomer A$_2$) (1.1 g) is obtained in the form of a yellow powder melting at about 126° C.

NMR spectrum:

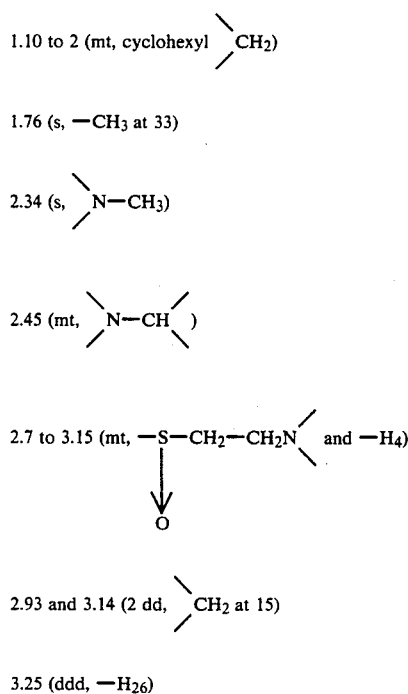

1.10 to 2 (mt, cyclohexyl >CH$_2$)

1.76 (s, —CH$_3$ at 33)

2.34 (s, >N—CH$_3$)

2.45 (mt, >N—CH<)

2.7 to 3.15 (mt, —S—CH$_2$—CH$_2$N< and —H$_4$)
↓
O 2.93 and 3.14 (2 dd, >CH$_2$ at 15)

3.25 (ddd, —H$_{26}$)

3.82 (s, >CH$_2$ at 17)

4.82 (d, —H$_{27}$)
5.52 (d, —H$_{13}$)
6.18 (d, —H$_{11}$)

6.43 (dd, >NH at 8)

8.13 (s, —H$_{20}$)

26-)N-Cyclohexyl-N-methyl-2-aminoethyl)thiopristinamycin II$_B$ (isomers: 80% A, 20% B) can be obtained by a method similar to that described in Example 3 for the preparation of the starting material, but starting from pristinamycin II$_A$ (10.5 g) and N-cyclohexyl-N-methyl-2-aminoethanethiol (4 g). After purification by "flash" chromatography [eluent: ethyl acetate-methanol (80-20 by volume)], 30-cc fractions being collected, and concentrating fractions 42 to 96 to dryness under reduced pressure (2.7 kPa) at 30° C., a yellow solid is obtained which is stirred in isopropyl ether (80 cc), separated off by filtration and then dried under reduced pressure (90 Pa) at 35° C. In this manner, 26-(N-cyclohexyl-N-methyl-2-aminoethyl)thiopristinamycin II$_B$ (isomers: 80% A and 20% B) (7.9 g) is obtained in the form of a yellow powder melting at about 116° C.

NMR spectrum (80/20 mixture of two isomers A and B): 1.25 and 1.6 to 1.9 (mt, cyclohexyl >CH$_2$ for A and B), 1.56 (s, —CH$_3$ at 33 of B), 1.73 (s, —CH$_3$ at 33 of A), 2.25 to 2.5 (mt, cyclohexyl >CH— for A and B), 2.32 (s, >N—CH$_3$ of B), 2.35 (s, >N—CH$_3$ of A), 2.6 to 2.8 (mt, —H$_4$ of A and B), 2.78 (borderline AB, —SCH$_2$CH$_2$N< of A and B), 2.9 and 3.14 (2dd, >CH$_2$ at 15 of A), 3.41 (broad d, —H$_{26}$ of A), 3.73 and 3.91 (2d, >CH$_2$ at 17 of B), 3.83 (s, >CH$_2$ at 17 of A), 4.65 (d, —H$_{27}$ of B), 4.76 (broad s, —H$_{27}$ of A), 5.49 (d, —H$_{13}$ of A), 6.16 (d, —H$_{11}$ of A), 6.36 (mf, >NH at 8 of A), 7.73 (mf, >NH at 8 of B), 7.82 (s, —H$_{20}$ of B), 8.13 (s, —H$_{20}$ of A).

N-Cyclohexyl-N-methyl-2-aminoethanethiol can be obtained as follows:

A 6N aqueous solution of sodium hydroxide (23 cc) is added under a nitrogen atmosphere to S-(N-cyclohexyl-N-methyl-2-aminoethyl)isothiouronium dihydrochloride (20 g). After being stirred at 100° C. for 2 hours, the mixture is cooled to 25° C. and then a concentrated solution of hydrochloric acid is added to it to a pH of 9. The solution is washed with dichloromethane (3×50 cc) and then the organic phases are combined, dried over magnesium sulphate, filtered, and then concentrated to dryness under reduced pressure (2.7 kPa) at 30° C. to give an oil, which is purified by distillation under reduced pressure (130 Pa). N-Cyclohexyl-N-methyl-2-aminoethanethiol (4.3 g) is obtained in the form of a colourless liquid [b.p. (130 Pa) =68° C.].

N-Cyclohexyl-N-methyl-2-aminoethanethiouronium dihydrochloride can be obtained as follows:

Thiourea (10.7 g) is added to 2-(N-cyclohexyl-N-methyl-amino)-1-chloroethane hydrochloride (30 g) in ethanol (300 cc). The solution obtained is heated for 18 hours at 78° C. After cooling, the white solid obtained is filtered off and then washed with ethanol. In this manner, N-cyclohexyl-N-methyl-2-aminoethanethiouronium dihydrochloride (21.5 g) is obtained in the form of a white solid melting at 248° C.

2-(N-Cyclohexyl-N-methyl-amino)-1-chloroethane hydrochloride can be obtained as follows:

N-Cyclohexyl-N-methyl-2-aminoethanol (25 g) is added dropwise to thionyl chloride (120 cc) and then the mixture is heated for 24 hours at 70° C. After the excess thionyl chloride has been distilled off, the orange oil obtained is stirred into ethyl ether (200 cc) to give a white solid, which is separated off by filtrattion and then washed with ether. 2-(N-Cyclohexyl-N-methyl-amino)-1-chloroethane (30 g) is obtained in the form of a white solid melting at 154° C.

EXAMPLE 21

By using a method similar to that described in Example 1, but starting from 26-[(4-methyl-1-piperazinyl)-2-carbonyloxyethyl]thiopristinamycin $II_B$ (isomer A) (4.3 g) trifluoroacetic acid (0.45 cc) and meta-chloroperbenzoic acid (1.2 g), and after purification by "flash" chromatography [eluent: chloroform-methanol (90-10 by volume)], 30-cc fractions being collected, and concentrating fractions 42 to 56 to dryness under reduced pressure (2.7 kPa) at 30° C., 26-[(4-methyl-1-piperazinyl)-2-carbonyloxyethyl]sulphinylpristinamycin $II_B$ (isomer $A_2$) (1.2 g) is obtained in the form of a light-yellow powder melting at about 135° C.

NMR spectrum:

1.78 (s, —CH$_3$ at 33)

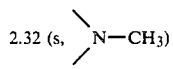
2.32 (s, \N—CH$_3$)

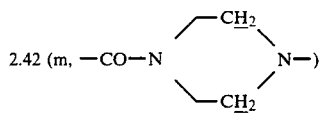
2.42 (m, —CO—N)

2.95 to 3.28 (2mt, —S—CH$_2$—)
↓
O

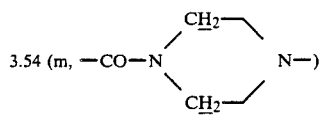
3.54 (m, —CO—N)

3.82 (s, \CH$_2$ at 17)

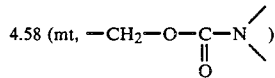
4.58 (mt, —CH$_2$—O—C—N)
            ‖
            O 4.82 (d, —H$_{27}$)
5.50 (d, —H$_{13}$)
6.20 (d, —H$_{11}$)

6.39 (dd, \NH at 8)

8.14 (s, —H$_{20}$)

After concentrating fractions 65 to 95 to dryness under reduced pressure (2.7 kPa) at 30° C., 26-[(4-methyl-1-piperazinyl)-2-carbonyloxyethyl]sulphinylpristinamycin $II_B$ (isomer $A_1$) (0.65 g) is obtained in the form of a light-yellow powder melting at about 140° C.

NMR spectrum:

1.75 (s, —CH$_3$ at 33)

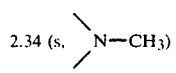
2.34 (s, \N—CH$_3$)

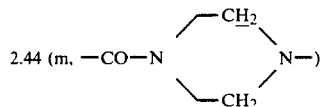
2.44 (m, —CO—N)

2.90 to 3.15 (mt, —S—CH$_2$—)
↓
O

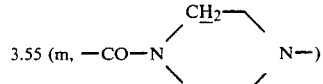
3.55 (m, —CO—N)

3.83 (s, \CH$_2$ at 17)

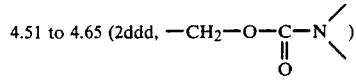
4.51 to 4.65 (2ddd, —CH$_2$—O—C—N)
              ‖
              O 5.28 (d, —H$_{27}$)
6.19 (d, —H$_{11}$)

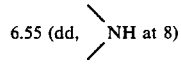
6.55 (dd, \NH at 8)

8.14 (s, —H$_{20}$)

26-[(4-Methyl-1-piperazinyl)-2-carbonyloxyethyl]thiopristinamycin $II_B$ can be prepared as follows:

By using a method similar to that described in Example 3, starting from pristinamycin $II_A$ (5.25 g) and (4-methyl-1-piperazinyl)-2-carbonyloxyethanethiol (3.76 g), and after purification by "flash" chromatography [eluent: chloroform-methanol (90-10 by volume)] and concentrating fractions 10 to 18 to dryness under reduced pressure (2.7 kPa) at 30° C., 26-[(4-methyl-1-piperazinyl)-2-carbonyloxyethyl]thiopristinamycin $II_B$ is obtained in the form of a beige powder melting at about 100° C.

NMR spectrum:

1.54 (s, —CH$_3$ at 33 of isomer B)
1.73 (s, —CH$_3$ at 33 of isomer A)

2.3 (s, \N—CH₃/)

2.4 (m, 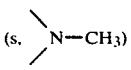)

3.55 (m, —OOC—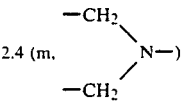)

3.98 (mt, —CH₂—OCO—)
4.59 (d, J = 4, —H₂₇ of isomer B)
4.69 (broad s, —H₂₇ of isomer A)

7.05 (t, \NH at 8 of isomer A /)

7.7 (m, \NH at 8 of isomer B /)

7.80 (s, —H₂₀ of isomer B)
8.10 (s, —H₂₀ of isomer A)

(4-Methyl-1-piperazinyl)-2-carbonyloxyethanethiol can be prepared according to the method described by D. D. Reynolds, D. L. Fields and D. L. Johnson, J. Org. Chem. 26, 5111 (1961).

EXAMPLE 22

By using a method similar to that described in Example 1, but starting from 26-[(S)-1-methyl-2-pyrrolidinyl]methylthiopristinamycin II$_B$ (isomer A) (7.8 g), trifluoroacetic acid (0.91 cc) and meta-chloroperbenzoic acid (2.4 g), and after purification by "flash" chromatography [eluent: chloroform-methanol (90-10 by volume)], 60-cc fractions being collected, and concentrating fractions 26 to 36 to dryness under reduced pressure (2.7 kPa) at 30° C., 26-[(S)-1-methyl-2-pyrrolidinyl]methylsulphinylpristinamycin II$_B$ (isomer A₂) (2.3 g) is obtained in the form of a light-yellow powder melting at about 140° C.

NMR spectrum:

1.76 (s, —CH₃ at 33)

2.48 (s, \NCH₃ /)

1.70 to 2.60 (mt, —H₂₉ and \CH₂ at 25 and / )

2.75 to 3.25 (mt, 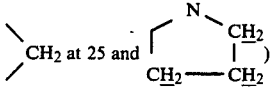)

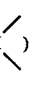

3.82 (s \CH₂ at 17 /)

4.81 (d, —H₂₇)
5.52 (d, —H₁₃)
6.20 (d, —H₁₁)

6.42 (dd, \NH at 8 /)

8.14 (s, —H₂₀)

After concentrating fractions 46 to 59 to dryness under reduced pressure (2.7 kPa) at 30° C., 26-[(S)-1-methyl-2-pyrrolidinyl]methylsulphinylpristinamycin II$_B$ (isomer A₁) (1.1 g) is obtained in the form of a light-yellow powder melting at about 148° C.

NMR spectrum:

1.73 (s, —CH₃ at 33)

1.70 to 2.50 (mt, 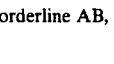, —H₂₉)

2.41 (s, \NCH₃ /)

2.65 to 3.25 (mt, \CH₂ at 15, —H at 4, 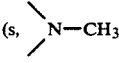)

3.82 (borderline AB, \CH₂ at 17 /)

5.45 (d, —H₁₃)
6.17 (d, —H₁₁)
8.11 (s, —H₂₀)

26-(1-Methyl-2-pyrrolidinyl)methylthiopristinamycin II$_B$ can be prepared as follows:

By using a method similar to that described in Example 3, but starting from pristinamycin II$_A$ (10.5 g) and [(S)-1-methyl-2-pyrrolidinyl]methanethiol (3.14 g), and after purification by "flash" chromatography [eluent: chloroform-methanol (90-10 by volume)] and concentrating fractions 20 to 35 to dryness under reduced pressure (2.7 kPa) at 30° C., the A isomer (7.8 g) is obtained in the form of a yellow powder melting at approximately 120° C.

NMR spectrum:

1.70 (s, —CH₃ at 33)

2.38 (s, 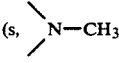)

1.70 to 2.50 (mt, —H29, \\CH2/ at 25 and  ⌈N(CH2)(CH2)—CH2—CH2⌉)

2.6 to 3.20 (mt, —S—CH2—CH\\/)

3.82 (s, \\CH2/ at 17)

4.73 (d, —H27)
5.45 (d, —H13)
6.15 (d, —H11)

6.41 (dd, \\NH/ at 8)

8.11 (s, —H20)

A 4N aqueous solution of sodium hydroxide (100 cc) is added to crude S-[(S)-1-methyl-2-pyrrolidinylmethyl-]isothiouronium dihydrochloride (25 g) dissolved in distilled water (100 cc), and then the mixture is stirred for 2 hours at 90° C. under a nitrogen atmosphere. The reaction mixture is cooled to 0° C., a 12N aqueous solution of hydrochloric acid (25 cc) is added to it, and then it is extracted with methylene chloride (2×200 cc). The organic phase is dried over sodium sulphate, filtered, and then concentrated to dryness under reduced pressure (2.7 kPa) at 30° C. In this manner [(S)-1-methyl-2-pyrrolidinyl]methanethiol (5.9 g) is obtained in the form of a light-yellow oil, which is used in the subsequent reaction without additional purification.

Rf=0.15; silica gel chromatographic plate; eluent: chloroform-methanol (90-10 by volume).

Thiourea (10.7 g) is added to [(S)-1-methyl-2-pyrrolidinyl]chloromethane hydrochloride (11.9 g) dissolved in ethanol (50 cc), and then the mixture is stirred for 48 hours under reflux. The mixture is concentrated to dryness under reduced pressure (2.7 kPa) at 40° C. The residue is taken up again with hot ethanol (100 cc) and then filtered through activated plant charcoal. After the filtrate has been concentrated to dryness under reduced pressure (2.7 kPa) at 40° C., a light-yellow oil (25 g) consisting of S-[(S)-1-methyl-2-pyrrolidinylmethyl]isothiouronium dihydrochloride and excess thiourea, is obtained.

Rf=0.1; silica gel chromatographic plate; eluent: chloroform-methanol (90-10 by volume).

[(S)-1-Methyl-2-pyrrolidinyl]chloromethane hydrochloride can be prepared according to the method described by T. Hayashi et al., J. Org. Chem., 48, 2195 (1983).

EXAMPLE 23

By using a method similar to that described in Example 1, but starting from 26-(1-methyl-4-piperidinyl)-thiopristinamycin II$_B$ (2.6 g), trifluoroacetic acid (0.3 cc) and meta-chloroperbenzoic acid (0.8 g), and after purification by "flash" chromatography [eluent: chloroform-methanol (90-10 by volume)], 40-cc fractions being collected, and concentrating fractions 20 to 35 to dryness under reduced pressure (2.7 kPa) at 30° C., 26-(1-methyl-4-piperidinyl)sulphinylpristinamycin II$_B$ (isomer A$_2$) (0.33 g) is obtained in the form of a yellow powder melting at about 170° C.

NMR spectrum:

1.76 (s, —CH3 at 33)

2.2 to 3.00 (mt, —CH(CH2—CH2)(CH2—CH2)N—)

2.32 (s, \\N—CH3/)

3.82 (s, \\CH2/ at 17)

4.85 (d, —H27)
5.50 (d, —H13)
6.19 (d, —H11)

6.37 (dd, \\NH/ at 8)

8.15 (s, —H20)

26-(1-Methyl-4-piperidinyl)thiopristinamycin II$_B$ can be obtained as follows:

By using a method similar to that described in Example 3, but starting from pristinamycin II$_A$ (3.15 g) and 2-methyl-4-piperidinethiol (1.6 g), and adding triethylamine (0.6 g) to the reaction mixture, and after purification by "flash" chromatography [eluent: methylene chloride-methanol (92-8 by volume)], and concentrating fractions 4 to 20 to dryness under reduced pressure (2.7 kPa) at 30° C., 26-(1-methyl-4-piperidinyl)thiopristinamycin II$_B$ (0.9 g) is obtained in the form of a yellow powder melting at about 180° C.

NMR spectrum:

2.10 (m, 4H: —S—⟨CH2\\/CH2⟩N—)

2.25 (s, 3H: —S—⟨⟩N—CH3)

2.80 (m, 4H: —S—⟨CH2\\/CH2⟩N—)

3.55 (m, 1H: —H26)
4.62 (m, 1H: —H27)
7.70 (m, 1H: —H8)
8.10 (s, 1H: —H20)

2-Methyl-4-piperidinethiol can be prepared by the method described by H. Barrer and R. E. Lyle, J. Org. Chem., 27, 641 (1962).

EXAMPLE 24

Trifluoroacetic acid (0.92 cc) is added under a nitrogen atmosphere to 26-(2-diethylaminoethyl)thiopristinamycin $II_B$ (7.8 g) dissolved in methanol (60 cc), at 0° C. After 15 minutes at 0° C., the temperature is raised to 15° C., and then selenium dioxide (1.37 g) is added. When all the selenium dioxide has dissolved, a 30% strength aqueous solution of hydrogen peroxide (7 cc) is added slowly at a temperature below 25° C. After being stirred at 25° C. for 1 hour, the reaction mixture is cooled to 10° C., a saturated aqueous solution of sodium bicarbonate (50 cc) is added to it, and then it is extracted with methylene chloride (4×50 cc). The organic phases are combined, dried over magnesium sulphate, filtered, and then concentrated to dryness under reduced pressure (2.7 kPa) at 30° C. The yellow solid obtained is purified by "flash" chromatography [eluent: chloroform-methanol (90-10 by volume)], 40-cc fractions being collected. After concentrating fractions 31 to 38 to dryness under reduced pressure (2.7 kPa) at 30° C., a yellow solid is obtained, which is purified by "flash" chromatography [eluent: ethyl acetate-methanol (80-20 by volume)], 40-cc fractions being collected. After concentrating fractions 27 to 33 to dryness under reduced pressure, a white solid is obtained, which is stirred in ethyl ether (50 cc), separated off by filtration and then dried under reduced pressure (90 Pa) at 30° C. In this manner, 26-(2-diethylaminoethyl)sulphonylpristinamycin $II_B$ (isomer A) (0.5 g) is obtained in the form of a white solid melting at about 150° C.

NMR spectrum:

0.97 (d, —$CH_3$ at 30 and 31 and ethyl —$CH_3$)
1.75 (s, —$CH_3$ at 33)

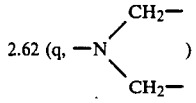
2.62 (q, —N)

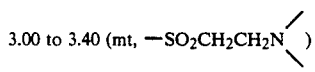
3.00 to 3.40 (mt, —$SO_2CH_2CH_2N$)

3.82 (s, $CH_2$ at 17)

5.34 (d, —$H_{13}$)
5.43 (d, —$H_{13}$)
6.16 (d, —$H_{11}$)

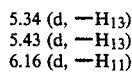
6.54 (dd, NH at 8)

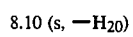
8.10 (s, —$H_{20}$)

EXAMPLE 25

A method similar to that described in Example 24 is used, but starting from 26-(2-diisopropylaminoethyl)thiopristinamycin $II_B$ (isomer A) (6.86 g), trifluoroacetic acid (0.77 cc), selenium dioxide (1.15 g), and a 30% strength aqueous solution of hydrogen peroxide (6.33 cc). After purification by "flash" chromatography [eluent: ethyl acetate-methanol (80-20 by volume)], 40-cc fractions being collected, and concentrating fractions 28 to 31 to dryness under reduced pressure (2.7 kPa) at 30° C., a yellow solid (0.7 g) is obtained, which is purified again by "flash" chromatography [eluent: ethyl acetate-methanol (85-15 by volume)], 30-cc fractions being collected. After concentrating fractions 26 to 33 to dryness under reduced pressure, a yellow solid is obtained, which is stirred in ethyl ether (30 cc), separated off by filtration and then dried under reduced pressure (90 Pa) at 30° C. 26-(2-Diisopropylaminoethyl)sulphonylpristinamycin $II_B$ (isomer A) (0.6 g) is obtained in the form of a light-yellow solid melting at about 140° C.

NMR spectrum:

1.06 (d, isopropyl —$CH_3$)
1.75 (s, —$CH_3$ at 33)
2.79 (mt, —$H_4$)

2.92 and 3.10 (2dd, $CH_2$ at 15)

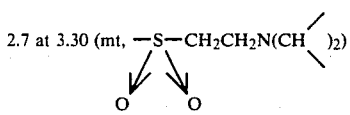
2.7 at 3.30 (mt, —S—$CH_2CH_2N(CH)_2$)

3.52 (broad d, —$H_{26}$)

3.82 (s, $CH_2$ at 17)

5.27 (fine d, —$H_{27}$)
5.47 (d, —$H_{13}$)
6.17 (d, —$H_{11}$)

6.42 (mt, NH at 8)

8.12 (s, —$H_{20}$)

Reference Example 1

Pristinamycin $I_A$ (0.5 g) and sodium cyanoborohydride (20 mg) are added to a solution of 3-dimethylaminopropylamine (0.41 cc) in methanol (15 cc) containing a 2N methanolic solution (2.4 cc) of hydrogen chloride gas, maintained at 55° C. The solution obtained is then allowed to regain a temperature of about 20° C. over approximately 2 hours, and it is then concentrated to dryness under reduced pressure (2.7 kPa) at 30° C. The residue obtained is triturated with a mixture of methylene chloride (50 cc) and of a saturated aqueous solution of sodium bicarbonate (50 cc); the organic phase is separated off and the aqueous phase is extracted twice with methylene chloride (20 cc in total). The organic phases are combined, dried over magnesium sulphate, filtered, and then concentrated to dryness under reduced pressure (2.7 kPa) at 30° C. The residue obtained is purified by "flash" chromatography [eluent: chloroform-methanol (80-20 by volume)]. Fractions 15 to 30 are combined and concentrated to dryness under reduced pressure (2.7 kPa) at 30° C.; the residue obtained is triturated with ethyl ether (5 cc), filtered off and dried under reduced pressure (0.027 kPa) at 20° C. In this manner 5γ-deoxy(3-dimethylaminopropyl)-5γ-aminopristinamycin $I_A$ (60 mg) is obtained in the form of a cream-colored powder melting at about 160° C.

The complete NMR spectrum shows the following characteristics:

| δ (ppm) | Form of signal | Attribution |
|---|---|---|
| 8.40 | d | 6 NH |
| 8.25 | d | 1 NH |
| 7.55 | dd | $H_6$ |
| 7.05 | m | 6γ + 6δ + 6ε |
| 7 | dd | $H_4$ |
| 6.90 | dd | $H_5$ |
| 6.70 | d | } 4δ + 4ε |
| 6.40 | d | |
| 6.50 | d | 2 NH |
| 5.75 | ddd | 1β |
| 5.45 | d | 6α |
| 5.25 | dd | 4α |
| 5 | s (broad) | 5α |
| 4.75 | dd | 1α |
| 4.60 | m | 2α |
| 4.45 | (d broad) | 5ε₁ |
| 4.40 | dd | 3α |
| 3.4 | (dd broad) | 3δ₁ |
| 3.20 | (dd broad) | 3δ₂ |
| 3 | s | 4 $CH_3$ |
| 3 | m | 5γ + 4β₁ and 2 |
| 2.80 | s | 4 $N(CH_3)_2$ |
| 2.65 | t | —$NCH_2$— (chain) |
| 2.35 | m | 5ε₂ + 5β₁ |
| 2.25 | t | —$NCH_2$— (chain) |
| 2.20 | s | —$N(CH_3)_2$ (chain) |
| 1.60 | m | —$CH_2$— (chain) 2β + 3γ |
| 1.25 | d | 1γ |
| 0.90 | t | 2γ |
| 0.50 | dddd | 5β₂ |

An aqueous solution at a concentration of 10% of 5γ-deoxy-(3-dimethylaminopropyl)-5γ-amino-pristinamycin $I_A$ (product A), in the form of hydrochloride, is obtained with:

| | |
|---|---|
| product A | 0.1 g |
| 2 N hydrochloric acid | 0.52 cc |
| distilled water q.s. | 1 cc |

By using a method similar to that described in the reference Example 1, the following synergistins of general formula (V), which can be combined with the products according to the invention, are prepared:

[The symbols ====, Z and $R_1$ are defined as at (1) for the general formula (V)].

| Reference example | Y | X | (1) Melting point (2) Solubility |
|---|---|---|---|
| 2 | —$N(CH_3)_2$ | —$NH(CH_2)_2N(CH_3)_2$ | (1) Yellow powder M. abt 180° C. (2) 10% aqueous solution of hydrochloride |
| 3 | —$N(CH_3)_2$ |  —N‾‾N—$CH_3$ | (1) White powder M. abt. 195° C. (2) 10% aqueous solution of hydrochloride |
| 4 | —$N(CH_3)_2$ | 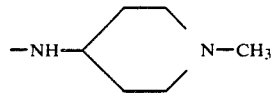 —NH—‾‾N—$CH_3$ | (1) Beige powder (2) M. abt. 195° C. 3.7% aqueous solution of hydrochloride |
| 5 | —$N(CH_3)_2$ | —NHOH | (1) White powder M. abt. 170° C. (2) 10% aqueous solution of hydrochloride |
| 6 | —$N(CH_3)_2$ | —$NH(CH_2)_3OH$ | (1) Cream powder M. abt. 160° C. (2) 2% aqueous solution of hydrochloride |
| 7 | —H | —$NH(CH_2)_3N(CH_3)_2$ | (1) Beige powder M. abt. 140° C. (2) 10% aqueous solution of hydrochloride |

Reference Example 8

A 5N ethanolic solution (2.8 cc) of dimethylamine, followed by a 5N methanolic solution (2 cc) of hydrogen chloride gas are added to a solution of pristinamycin $I_A$ (2 g) in methanol (25 cc). Sodium cyanoborohydride (76 mg) are added to the solution thus obtained, and the mixture is then stirred at a temperature of about 20° C. for 48 hours. The reaction mixture is then concentrated to dryness under reduced pressure (2.7 pKa) at 30° C. The residue is triturated with a mixture of methylene chloride (25 cc) and of a saturated aqueous solution of sodium bicarbonate (25 cc); the organic phase is separated off and the aqueous phase is extracted twice with methylene chloride (50 cc in total). The organic phases are combined, dried over magnesium sulphate, filtered, and then concentrated to dryness under reduced pressure (2.7 kPa) at 30° C. The residue is purified by "flash" chromatography [eluent: chloroform-methanol (92-8 by volume)]. Fractions 5 to 12 are combined and concentrated to dryness under reduced pressure (2.7 kPa) at 30° C. In this manner 5γ-deoxy-5γ-dimethylaminopristinamycin $I_A$ (0.7 g) is obtained in the form of a beige powder melting at about 170° C.

NMR spectrum: 0.70 (dt, 1H: 5$\beta_2$), 2.10 to 2.60 (m, 4H: 5$\delta_1$+5$\delta_2$+5$\beta_1$+5$\gamma$) 2.15 (s, 3H×0.8: —N(CH$_3$)$_2$ 1st isomer), 2.20 (s, 3H×0.2: —N(CH$_3$)$_2$ 2nd isomer).

An aqueous solution at a concentration of 2% of 5$\gamma$-deoxy-5$\gamma$-dimethylaminopristinamycin I$_A$ (product B), in the form of hydrochloride, is obtained with:

| product B | 0.05 g |
| 0.1 N hydrochloric acid | 0.56 cc |
| distilled water q.s. | 2.5 cc |

Reference Example 9

By using a method similar to that described in reference Example 8, 5$\gamma$-deoxy-5$\gamma$-methylaminopristinamycin I$_A$ (0.35 g) is obtained in the form of a yellow powder melting at about 185° C.

An aqueous solution at a concentration of 1% of 5$\gamma$-deoxy-5$\gamma$-methylaminopristinamycin I$_A$, in the form of hydrochloride, is obtained.

Reference Example 10

By using a method similar to that described in reference Example 8, 5$\gamma$-deoxy-5$\gamma$-[N-(2-dimethylaminoethyl)-N-methylamino]pristinamycin I$_A$ is obtained in the form of a white powder melting at about 120° C.

An aqueous solution at a concentration of 10% of 5$\gamma$-deoxy-5$\gamma$-[N-(2-dimethylaminoethyl)-N-methylamino]pristinamycin I$_A$ (product D), in the form of hydrochloride, is obtained.

Reference Example 11

A 3-Å molecular sieve (5 g) is added to a solution of pristinamycin I$_A$ (3 g), 4-diethylamino-2-methylbutylamine (3.3 g), sodium cyanoborohydride (0.11 g) and a 5N methanolic solution (9 cc) of hydrogen chloride gas in methanol (75 cc). The suspension obtained is stirred at a temperature of about 20° C. for 4 days, and is then filtered; the filtrate is concentrated to dryness under reduced pressure (2.7 kPa) at 30° C. The residue is triturated with a mixture of methylene chloride (50 cc) and a saturated aqueous solution of sodium bicarbonate (50 cc); the organic phase is separated off and the aqueous phase is extracted twice with methylene chloride (50 cc in total). The organic phases are combined, dried over magnesium sulphate, filtered and then concentrated to dryness under reduced pressure (2.7 kPa) at 30° C. The residue is purified by "flash" chromatography [eluent: chloroform-methanol (90-10 by volume)]. In this manner, 5$\gamma$-deoxy-15 5$\gamma$-(4-diethylamino-2-methylbutyl)aminopristinamycin I$_A$ (0.7 g) is obtained in the form of a beige powder melting at about 160° C.

NMR spectrum:

1.10 (mt, 9H: —N(CH$_2$C<u>H</u>$_3$)$_2$ + 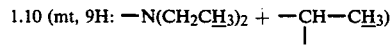

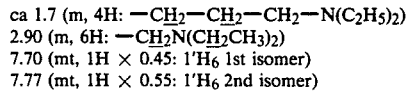

ca 1.7 (m, 4H: —C<u>H</u>$_2$—C<u>H</u>$_2$—C<u>H</u>$_2$—N(C$_2$H$_5$)$_2$)
2.90 (m, 6H: —C<u>H</u>$_2$N(C<u>H</u>$_2$CH$_3$)$_2$)
7.70 (mt, 1H × 0.45: 1'H$_6$ 1st isomer)
7.77 (mt, 1H × 0.55: 1'H$_6$ 2nd isomer)

An aqueous solution at a concentration of 10% of 5$\gamma$-deoxy-5$\gamma$-(4-diethylamino-2-methylbutyl)aminopristinamycin I$_A$ (product F) in the form of hydrochloride, is obtained with:

| product F | 0.1 g |
| 0.1 N hydrochloric acid q.s. | 1 cc |

Reference Example 12

Sodium cyanoborohydride (0.7 g) is added to a solution of 5$\gamma$-deoxy-5$\gamma$-hydroxyiminopristinamycin I$_A$ (12.5 g) in methanol (300 cc) containing a 2N methanolic solution (10 cc) of hydrogen chloride gas. The solution obtained is stirred at a temperature of about 20° C. for 2 days, and is then concentrated to dryness under reduced pressure (2.7 kPa) at 30° C. The residue is triturated in a mixture of methylene chloride (200 cc) and a saturated aqueous solution of sodium bicarbonate (100 cc); the organic phase is separated off and the aqueous phase is extracted with methylene chloride (100 cc). The organic phases are combined, dried over magnesium sulphate, filtered, and concentrated to dryness under reduced pressure (2.7 kPa) at 30° C. After purification by "flash" chromatography [eluent: chloroform-methanol (95-5 by volume)], 5$\gamma$-deoxy-5$\gamma$-hydroxyaminopristinamycin I$_A$ (6.8 g) is obtained in the form of a white powder melting at about 170° C.

NMR spectrum: 0.4 (m, 1H: 5$\beta_2$), 2.45 (d, 1H: 5$\beta_1$), 3.1 (d: 5$\gamma$ in complex unresolved bands), 7.80 (mt, 1H×0.75: 1'H$_6$ 1st isomer), 7.95 (mt, 1H×0.25: 1'H$_6$ 2nd isomer).

5$\gamma$-Deoxy-5$\gamma$-hydroxyiminopristinamycin I$_A$ can be obtained by stirring pristinamycin I$_A$ (15 g) and hydroxylamine hydrochloride (7.5 g) dissolved in methanol (150 cc) containing a 2N methanolic solution (8 cc) of hydrogen chloride gas for 5 hours at a temperature of about 20° C. The reaction mixture is then concentrated to dryness under reduced pressure (2.7 kPa) at 30° C. The residue is triturated with a mixture of chloroform (100 cc) and of a saturated aqueous solution of sodium bicarbonate (100 cc); the organic phase is separated off and the aqueous phase is extracted twice with chloroform (200 cc in total). The organic phases are combined, dried over magnesium sulphate, filtered, and concentrated to dryness under reduced pressure (2.7 kPa) at 30° C. In this manner, 5$\gamma$-deoxy-5$\gamma$-hydroxyiminopristinamycin I$_A$ (14 g) is obtained in the form of a beige powder melting at 210° C.

NMR spectrum: 0.35 (dd, 1H: 5$\beta_2$), 3.25 (m, 2H: 4$\epsilon_2$+5$\beta_1$), 5.05 (d, 1H: 5$\alpha$), 5.5 (m, 2H including 5$\epsilon_1$), 7.80 (dd, 1H×0.40: 1'H$_6$ 1st isomer), 7.90 (dd, 1H×0.60: 1'H$_6$ 2nd isomer).

Reference Example 13

By using a method similar to that described in reference Example 11, 5$\gamma$-[N-(carboxymethyl)methylamino]-5$\gamma$-deoxypristinamycin I$_A$ (0.8 g) is obtained in the form of a cream-coloured powder melting at about 140° C.

An aqueous solution at a concentration of 2% of 5$\gamma$-[N-(carboxymethyl)methylamino]-5$\gamma$-deoxypristinamycin I$_A$ (product K) is obtained with:

| product K | 0.2 g |
| distilled water q.s. | 10 cc |

Reference Example 14

Acetyl chloride (0.3 cc) is added to a solution of 5γ-deoxy-5γ-(2-dimethylaminoethyl)aminopristinamycin $I_A$ (3.2 g) in chloroform (50 cc) containing triethylamine (0.6 cc). The reaction mixture is stirred at a temperature of about 20° C. for 30 minutes and is then concentrated to dryness under reduced pressure (2.7 kPa) at 30° C. The residue is purified by "flash" chromatography [eluent: chloroform-methanol (90-10 by volume)]; by concentrating fractions 10 to 21 to dryness under reduced pressure (2.7 kPa) at 30° C., 5γ-deoxy-5γ-[N-(2-dimethylaminoethyl)acetamido]pristinamycin $I_A$ (1.8 g) is obtained in the form of a white powder melting at about 170° C.

NMR spectrum: 0.9 (m, 4H: 2γ+5β$_2$), 2.05 to 2.15 (m, 3H: 5δ$_1$+5δ$_2$+5γ), 2.15 (S, 3H: —COCH$_3$), 2.45 (s, 6H: —N(CH$_3$)$_2$), 2.35 to 2.60 (m, 5H: >N—C$\underline{H}_2$—C$\underline{H}_2$—N<+5β$_1$), 7.8 (mt, 1H×0.75: 1'H$_6$ 1st isomer), 8.25 (mt, 1H×0.25: 1'H$_6$ 2nd isomer).

An aqueous solution at a concentration of 10% of 5γ-deoxy-5γ-[N-(2-dimethylaminoethyl)acetamido]pristinamycin $I_A$ (product L), in the form of hydrochloride, is obtained with:

| product L | 0.1 g |
|---|---|
| 0.2 N hydrochloric acid | 0.51 cc |
| distilled water q.s. | 1 cc |

5γ-Deoxy-5γ-(2-dimethylaminoethyl)aminopristinamycin $I_A$ can be prepared as described in Reference Example 2.

Reference Example 15

By using a method similar to that described in Reference Example 14, 5γ-deoxy-5γ-[N-(3-dimethylaminopropyl)acetamido]pristinamycin $I_A$ (1.6 g) is obtained in the form of an ochre powder melting at 210° C.

An aqueous solution at a concentration of 10% of 5γ-deoxy-5γ-[N-(3-dimethylaminopropyl)acetamido]pristinamycin $I_A$ (product M), in the form of hydrochloride, is obtained.

Reference Example 16

3-Dimethylaminopropanethiol (1.95 g) is added to a solution of 5δ-methylenepristinamycin $I_A$ (3.6 g) in a mixture of methanol (25 cc) and chloroform (5 cc), and then the solution obtained is stirred at a temperature of about 20° C. for 20 hours. The reaction mixture is then poured into distilled water (250 cc); the emulsion obtained is extracted 3 times with methylene chloride (250 cc in total). The organic phases are combined, dried over magnesium sulphate, filtered, and then concentrated to dryness under reduced pressure (2.7 kPa) at 30° C. The residue obtained is purified by "flash" chromatography [eluent: chloroform-methanol (95-5 by volume)]; fractions 10 to 38 are concentrated to dryness under reduced pressure (2.7 kPa) at 30° C. The residue obtained is triturated in ethyl ether (30 cc); the crystals obtained are separated off by filtration, and then dried under reduced pressure (27 Pa) at 20° C. In this manner, 5δ-(3-dimethylaminopropyl)thiomethylpristinamycin $I_A$ is obtained in the form of white crystals melting at 234° C.

NMR spectrum:

| δ (ppm) | Form | Attribution |
|---|---|---|
| 11.65 | s (broad) | OH |
| 8.70 | d | 6NH |
| 8.40 | d | 1NH |
| 7.80 | dd | 1'H$_6$ |
| 7.45 | m | 1'H$_4$ + 1'H$_5$ |
| 7.27 | m | 6γ + 6δ + 6ε |
| 7.17 | m | |
| 7.05 | d ⎫ AB system | 4δ + 4ε |
| 6.60 | d ⎭ | |
| 6.47 | d | 2 \NH / |
| 5.87 | ddd | 1β |
| 5.83 | d | 6α |
| 5.24 | m | 5α + 4α |
| 5.03 | ddd | 5ε$_1$ |
| 4.85 | dd | 1α |
| 4.80 | m | 2α |
| 4.53 | dd | 3α |
| 3.53 | m | 3δ$_1$ |
| 3.35 | dd ⎫ ABX system | —C$\underline{H}_2$—S—SC$\underline{H}_2$— |
| 3.15 | dd ⎭ | |
| 3.25 | s | 4 \NCH$_3$ / |
| 3.25 | m | 3δ$_2$ |
| 2.90 | s | 4-N(CH$_3$)$_2$ |
| 2.90 | m | 4β |
| 2.55 | t | —C$\underline{H}_2$N(CH$_3$)(CH$_3$) |
| 2.50 | dd | 5ε$_2$ |
| 2.40 | t | —CH$_2$SCH$_2$— |
| 2.40 to 2.20 | m | 5δ + 5β$_1$ |
| 2.25 | s | —CH$_2$N(CH$_3$)$_2$ |
| 2 | m | 3β$_1$ |
| 1.75 | m | —SCH$_2$CH$_2$CH$_2$— |
| 1.8 to 1.45 | m | 2β$_1$ + 2β$_2$ + 3γ$_1$ |
| 1.30 | d | 1γ |
| 1.25 to 1.05 | m | 3γ$_2$ + 3β$_2$ |
| 0.9 | t | 2γ |
| 0.60 | dd | 5β$_2$ |

An aqueous solution at a concentration of 10% of 5δ-(3-dimethylaminopropyl)thiomethylpristinamycin $I_A$ (product AA) is obtained with:

| product AA | 30 mg |
|---|---|
| 0.1 N hydrochloric acid q.s. | 0.3 cc |

5δ-methylenepristinamycin $I_A$ can be prepared as follows:

Sodium cyanoborohydride (0.43 g) is added to a solution of 5δ-dimethylaminomethylenepristinamycin $I_A$ (12 g) in tetrahydrofuran (230 cc) containing trifluoroacetic acid (1.2 cc). The solution obtained is stirred at a temperature of about 20° C. for 4 hours and is then concentrated to dryness under reduced pressure (2.7 kPa) at 30° C. The residue obtained is purified by "flash" chromatography [eluent: chloroform-methanol (95-5 by volume)]; fractions 4 to 15 are concentrated to dryness under reduced pressure (2.7 kpa) at 30° C. In this manner 5δ-methylenepristinamycin I$_A$ (5.5 g) is obtained in the form of white crystals melting at 245° C.

NMR spectrum:

0.55 (d, 1H: 5β$_2$)
2.40 (d, 1H: 5β$_1$)
3.55 (dd, 1H: 5ε$_2$)
5.25 (m, 2H: 5α + 5ε$_1$)

5.30 and 6.10 (2s, 2H: =C$\begin{smallmatrix}H\\H\end{smallmatrix}$ )

7.85 (dd, 1H: 1'H$_6$)

5δ-Dimethylaminomethylenepristinamycin I$_A$ can be prepared as follows:

tert-Butoxybis(dimethylamino)methane (230 cc) is added to a solution of pristinamycin I$_A$ (46 g) in 1,2-dichloroethane (460 cc); the solution obtained is stirred at a temperature of about 20° C. for 18 hours. The reaction mixture is diluted with methylene chloride (1 liter) and then washed 3 times with a 0.4% strength aqueous solution of ammonium chloride (3 liters in total). The organic phase is dried over magnesium sulphate, filtered and then concentrated to dryness under reduced pressure (2.7 kPa) at 30° C. The residue obtained is triturated with distilled water (600 cc); the mixture is filtered and the solid product is dried under reduced pressure (2.7 kPa) at 20° C. Crude 5δ-dimethylaminomethylenepristinamycin I$_A$ (41 g) is obtained in the form of a beige powder. This product is of an adequate quality to be used as such as in the subsequent steps. It can, however, be purified as follows:

Crude 5δ-dimethylaminomethylelenpristinamycin I$_A$ (23.5 g) is purified by "flash" chromatography [eluent: chloroform-methanol (98-2 by volume)]. Fractions 16 to 25 are combined and concentrated to dryness under reduced pressure (2.7 kPa) at 30° C. In this manner, 5δ-dimethylaminomethylenepristinamycin I$_A$ (12 g) is obtained in the form of a beige powder melting at about 195° C.

NMR spectrum: 0.9 (t, 3H: 2γ), 1.0 (dd, 1H: 5β$_2$), 2.50 (d, 1H, 5β$_1$), 3.10 (s, 6H: —N(CH$_3$)$_2$), 3.70 (d, 1H: 5ε$_2$), 5.50 (d, 1H: 5ε$_1$), 7.40 (s, 1H: =CHN(CH$_3$)$_2$), 7.75 (dd, 1H: 1'H$_6$).

Reference Example 17

By using a method similar to that described in Reference Example 16, but starting from 5δ-methylenevirginiamycin S (0.9 g) and 3-dimethylaminopropanethiol (0.52 g) and after purification by "flash" chromatography [eluent: chloroform-methanol (90-10 by volume)], and concentrating fractions 13 to 25 to dryness under reduced pressure (2.7 kPa) at 30° C., 5δ-(3-dimethylaminopropyl)thiomethylvirginiamycin S (0.3 g) is obtained in the form of a white powder melting at about 142° C.

NMR spectrum:

0.45 (dd, 1H: 5β$_2$)

1.90 (m, 2H: —SCH$_2$CH$_2$CH$_2$N$\diagup\diagdown$ )

2.40 (s, 6H: —CH$_2$—N$\begin{smallmatrix}\diagup CH_3\\ \diagdown CH_3\end{smallmatrix}$ )

2.60 (m, 4H: —S—CH$_2$—CH$_2$—CH$_2$—N$\diagup\diagdown$ )

3.45 (d, 1H: 5ε$_2$)

4.85 (m, 3H including 5ε$_1$)

5.25 (dd, 1H: 5α)

7.78 (dd, 1H: 1'H$_6$)

An aqueous solution at a concentration of 10% of 5δ-(3-dimethylaminopropyl)thiomethylviginiamycin S (product AB), in the form of hydrochloride, is obtained with:

| | |
|---|---|
| product AB | 0.1 g |
| hydrochloric acid q.s. | 1 cc |

5δ-Methylenevirginiamycin S can be prepared by a method similar to that described in Reference Example 16 for 5δ-methylenepristinamycin I$_A$, but starting from 5δ-dimethylaminomethylenevirginiamycin S (2 g) and sodium cyanoborohydride (74 mg). After purification by "flash" chromatography [eluent: chloroform-methanol (98-2 by volume)] and concentrating fractions 2 to 5 to dryness under reduced pressure (2.7 kPa) at 30° C., 5δ-methylenevirginiamycin S (1 g) is obtained in the form of a beige powder melting at about 190° C.

NMR spectrum:

0.35 (dd, 1H: 5β$_2$)
2.45 (dd, 1H: 5β$_1$)
3.55 (dd, 1H: 5ε$_2$)
5.25 (dd, 1H: 5ε$_1$)
5.25 (m, 1H: 5α)

5.30 and 6.15 (2s, 2H: =C$\begin{smallmatrix}H\\H\end{smallmatrix}$ )

7.75 (dd, 1: 1'H$_6$)

5δ-Dimethylaminomethylenevirginiamycin S can be obtained by using a method similar to that described in Reference Example 16 for 5δ-dimethylaminomethylenepristinamycin I$_A$, but starting from virginiamycin S (2 g) and bis(dimethylamino)tert-butoxymethane (10 cc) and, after purification by "flash" chromatography [eluent: chloroform-methanol (98-2 by volume)] and concentrating fractions 9 to 12 to dryness under reduced pressure (2.7 kPa) at 30° C., 5δ-dimethylaminomethylenevirginiamycin S (0.8 g) is obtained in the form of a yellow powder melting at about 175° C.

NMR spectrum: 0.9 (m, 4H: 2γ+5β$_2$), 3.05 (s, 6H: =CH—N(CH$_3$)$_2$), 3.65 (d, 1H: 5ε$_2$), 4.85 (d, 1H: 5ε$_1$), 5.15 (dd, 1H: 5α), 7.10 to 7.40 (m: aromatics+=CH—N<), 7.70 (dd, 1H: 1'H$_6$). Reference Example 18

By using a method similar to that described in Reference Example 16, but starting from 5δ-methylenepristinamycin I$_A$ (6 g) and 2-(4-methylpiperazinyl)ethanethiol (4 cc), and after purification by "flash" chromatography [eluent: chloroform-methanol (97-3 by volume)], and concentrating fractions 8 to 20 to dryness under reduced pressure (2.7 pKa) at 30° C., 5δ-[2-(4-methyl-piperazinyl)ethyl]thiomethylpristinamycin $I_A$ (2.6 g) is obtained in the form of white crystals melting at 216° C.

NMR spectrum:

0.60 (dd, 1H: 5β$_2$)

2.27 (s, 3H: \N—CH$_3$)

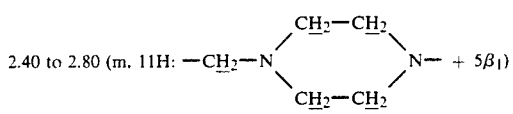

2.40 to 2.80 (m, 11H: —CH$_2$—N group + 5β$_1$)

5.05 (dd, 1H: 5ε$_1$)
5.27 (m, 2H: 5α + 4α)
7.85 (mt, 1H × 0.8: 1'H$_6$ 1st isomer)
7.95 (mt, 1H × 0.2: 1'H$_6$ 2nd isomer)

An aqueous solution at a concentration of 5% of 5δ-[2-(4-methyl-1-piperazinyl)ethyl]thiomethylpristinamycin $I_A$ (product AC), in the form of hydrochloride, is obtained with:

| product AC | 0.1 g |
|---|---|
| 0.1 N hydrochloric acid | 0.96 cc |
| distilled water q.s. | 2 cc |

Reference Example 19

By using a method similar to that described in reference Example 16, but starting from 5δ-methylenepristinamycin $I_A$ (2 g) and 3-(4-methyl-1-piperazinyl)-propanethiol (3 cc), and after purification by "flash" chromatography [eluent: chloroform-methanol (90-10 by volume)], and concentrating fractions 10 to 25 to dryness under reduced pressure (2.7 pKa) at 30° C., 5δ-[3-(4-methyl-1-piperazinyl)propyl]thiomethylpristinamycin $I_A$ (1.9 g) is obtained in the form of a white powder melting at about 156° C.

NMR spectrum:

0.65 (dd, 1H: 5β$_2$)

2.30 (s, 3H: \N—CH$_3$)

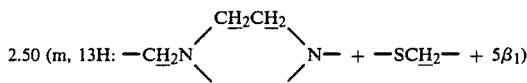

2.50 (m, 13H: —CH$_2$N group + —SCH$_2$— + 5β$_1$)

5.27 (m, 2H: 5α + 4α)
7.85 (dd, 1H × 0.8: 1'H$_6$ 1st isomer)
7.95 (dd, 1H × 0.2: 1'H$_6$ 2nd isomer)

An aqueous solution at a concentration of 10% of 5δ-[3-(4-methyl-1-piperazinyl)propyl]thiomethylpristinamycin $I_A$ (product AD), in the form of hydrochloride, is obtained with:

| product AD | 0.1 g |
|---|---|
| 0.5 N hydrochloric acid | 0.38 cc |
| distilled water q.s. | 1 cc |

Reference Example 20

By using a method similar to that described in Reference Example 16, but starting from 5δ-methylenepristinamycin $I_A$ (4 g) and 1,3-bisdimethylamino-2-propanethiol (4 cc), and after purification by "flash" chromatography [eluent: chloroform-methanol (95-5 by volume)], and concentrating fractions 20 to 60 to dryness under reduced pressure (2.7 kPa) at 30° C., 5δ-[1,3-bis(dimethylamino)-2-propyl]thiomethylpristinamycin $I_A$ (0.59 g) is obtained in the form of a white powder melting at about 170° C.

NMR spectrum:

0.63 (dd, 1H: 5β$_2$)
2.40 (s, 6H: —N(CH$_3$)$_2$)

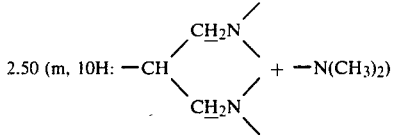

2.50 (m, 10H: —CH group + —N(CH$_3$)$_2$)

4.97 (s, 1H: 5ε$_1$)
5.30 (m, 2H: 5α + 4α)
7.85 (mt, 1H × 0.85: 1'H$_6$ 1st isomer)
7.95 (mt, 1H × 0.15: 1'H$_6$ 2nd isomer)

An aqueous solution at a concentration of 7.5% of 5δ-[1,3-bis(dimethylamino)-2-propyl]thiomethylpristinamycin $I_A$ (product AE), in the form of hydrochloride, is obtained with:

| product AE | 0.03 g |
|---|---|
| 0.1 N hydrochloric acid | 0.3 cc |
| distilled water q.s. | 0.4 cc |

Reference Example 21

By using a method similar to that described in reference Example 16, but starting from 5δ-methylenepristinamycin $I_A$ (3 g) and 2-methyl-4-mercaptopiperidine (0.97 g), and after purification by "flash" chromatography [eluent: chloroform-methanol (95-5 by volume)], and concentrating fractions 10 to 16 to dryness under reduced pressure (2.7 kPa) at 30° C., 5δ-(1-methyl-4-piperidyl)thiomethylpristinamycin $I_A$ (1.1 g) is obtained in the form of a white powder melting at 260° C.

NMR spectrum:

0.6 (dd, 1H: 5β$_2$)

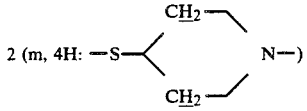

2 (m, 4H: —S group N—)

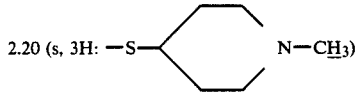

2.20 (s, 3H: —S group N—CH$_3$)

2.35 (m, 1H: 5β₁)

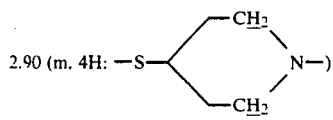

5.30 (m, 2H: 5α + 4α)
7.85 (dd, 1H: 1'H₆)

An aqueous solution at a concentration of 5% of 5δ-(1-methyl-4-piperidyl)thiomethylpristinamycin I$_A$ (product AF), in the form of hydrochloride, is obtained with:

| product AF | 0.03 g |
|---|---|
| 0.1 N hydrochloric acid | 0.3 cc |
| distilled water q.s. | 0.6 cc |

Reference Example 22

By repeating Reference Example 16, but starting from 5δ-methylenepristinamycin I$_A$ (2 g) and 2-diethylaminoethanethiol (0.66 g), after purification by "flash" chromatography [eluent: chloroform-methanol (95-5 by volume)], and concentrating fractions 9 to 18 to dryness under reduced pressure (2.7 kPa) at 30° C., 5δ-(2-diethylaminoethyl)thiomethylpristinamycin I$_A$ (0.8 g) is obtained in the form of a beige powder melting at 230° C.

NMR spectrum:

0.65 (dd, 1H: 5β₂)
2.38 (d, 1H: 5β₁)

2.3 to 2.8 (m, 8H: —SCH₂CH₂N$\diagup^{CH_2-}_{\diagdown CH_2-}$ )

3.15 (dd, 1H: —CH₂S—)
3.35 (dd, 1H: —CH₂S—)
5.01 (dd, 1H: 5ε₁)
7.81 (dd, 1H × 0.9: 1'H₆ 1st isomer)
7.90 (dd, 1H × 0.1: 1'H₆ 2nd isomer)

An aqueous solution at a concentration of 5% of 5δ-(2-diethylaminoethyl)thiomethylpristinamycin I$_A$ (product AF₁) in the form of hydrochloride, is obtained with:

| product AF₁ | 30 mg |
|---|---|
| 0.1 N hydrochloric acid | 0.29 cc |
| distilled water q.s. | 0.6 cc |

Reference Example 23

2-Dimethylaminoethylamine (5.3 g) is added dropwise, so as not to exceed 25° C., to a solution of 5δ-dimethylaminomethylenepristinamycin I$_A$ (5.5 g) in acetic acid (60 cc). The solution obtained is stirred at a temperature of about 20° C. for 20 hours and is then poured slowly into a saturated aqueous solution of sodium bicarbonate; the mixture obtained is extracted twice with methylene chloride (750 cc in total). The organic phases are combined, dried over magnesium sulphate, filtered, and concentrated to dryness under reduced pressure (2.7 kPa) at 30° C. The residue is purified by "flash" chromatography [eluent: chloroform-methanol (90-10 by volume)]; fractions 10 to 12 are concentrated to dryness under reduced pressure (2.7 kPa) at 30° C. In this manner 5δ-(2-dimethylaminoethyl)aminomethylenepristinamycin I$_A$ (3 g) is obtained in the form of a beige powder melting at about 180° C.

NMR spectrum:

0.90 (mt, 4H: 2γ + 5β₂)
2.25 (mt, 6H: —N(CH₃)₂)

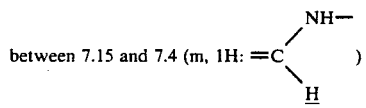

3.25 (mt, 2H: $\diagdown$N—CH₂—)
              $\diagup$ 3.50 (mt, 2H: 5ε₂ + 3δ₁)
4.90 (mt, 1H: 5ε₁)

between 7.15 and 7.4 (m, 1H: =C$\diagup^{NH-}_{\diagdown H}$ )

9.90 (mt, 1H (exchangeable with D₂O): —NH—)

An aqueous solution at a concentration of 1% of 5δ-(2-dimethylaminoethyl)aminomethylenepristinamycin I$_A$ (product AG) is obtained with:

| product AG | 0.1 g |
|---|---|
| distilled water q.s. | 10 cc |

Reference Example 24

By using a method similar to that described in Reference Example 23, but starting from 5δ-dimethylaminomethylenepristinamycin I$_A$ (13.8 g) and 4-amino-2-methylpiperidine (3.4 g), and after purification by "flash" chromatography [eluent: chloroform-methanol (92.5-7.5 by volume)], and concentrating fractions 15 to 20 to dryness under reduced pressure (2.7 kPa) at 30° C., 5δ-(1-methyl-4-piperidyl)aminomethylenepristinamycin I$_A$ (4.0 g) is obtained in the form of a yellow powder melting at 208° C.

NMR spectrum:

0.40 (m, 4H: 2γ + 2β₂)

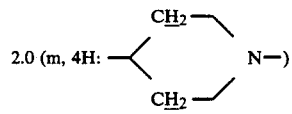

2.35 (s, 3H: $\diagdown$N—CH₃)
              $\diagup$ 2.45 (d, 1H: 5β₁)

2.90 (— 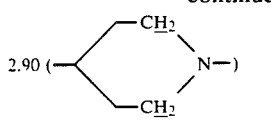

3.20 (under unresolved bands, 1H: —C$\underline{H}$ 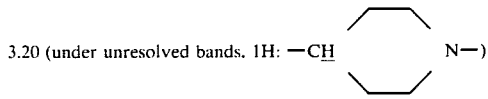

3.50 (d, 1H: 5ε$_2$)
4.85 (under unresolved bands, 1H: 5ε$_1$)
6.65 (d, 1H: =C$\underline{H}$NH—)
9.70 (dd, 1H × 0.15: =CH—NH— 1st isomer)
10.03 (dd, 1H × 0.85: =CH—N$\underline{H}$— 2nd isomer)

An aqueous solution at a concentration of 10% of 5δ-(1-methyl-4-piperidyl)aminomethylenepristinamycin I$_A$ (product AT), in the form of hydrochloride, is obtained with:

| | | |
|---|---|---|
| product AT | 0.03 | g |
| 0.1 N hydrochloric acid | 0.3 | cc |
| distilled water q.s. | 0.3 | cc |

4-Amino-2-methylpiperidine can be prepared by the method described by E. F. Elslager, L. M. Werbel, A. Curry, N. Headen, J. Johnson, J. Med. Chem. 17, 99 (1974).

By using the method of Reference Example 23, the following synergistins of general formula (V), which can be combined with the products according to the invention, are prepared.

[The symbols =====, X and Z are defined as at 2b) for the general formula (V) and, unless stated otherwise, Y denotes a dimethylamino radical].

| Reference example | Y | R$_4$ | | |
|---|---|---|---|---|
| | | | (1) | Melting point |
| | | | (2) | Solubility |
| 25 | | —NH—(CH$_2$)$_2$N(C$_2$H$_5$)$_2$ | (1) | Yellow powder M abt. 150° C. |
| | | | (2) | 5% aqueous solution as hydrochloride |
| 26 | | —NH(CH$_2$)$_2$NHCH$_3$ | (1) | Yellow powder M = 174° C. |
| | | | (2) | 1% aqueous solution as hydrochloride |
| 27 | | —NH(CH$_2$)$_3$N(CH$_3$)$_2$ | (1) | Yellow powder M abt. 155° C. |
| | | | (2) | 6.6% aqueous solution as hydrochloride |
| 28 | | —NH—CH—CH$_2$N(CH$_3$)$_2$ <br>         \|<br>        CH$_3$ | (1) | Yellow powder M abt. 160° C. |
| | | | (2) | 1% aqueous solution as hydrochloride |
| 29 | | —NHCH$_2$CH—N(CH$_3$)$_2$ <br>           \|<br>          CH$_3$ | (1) | Orange powder M abt. 175° C. |
| | | | (2) | 10% aqueous solution as hydrochloride |
| 30 | | —NH—CH—(CH$_2$)$_3$N(C$_2$H$_5$)$_2$ <br>         \|<br>        CH$_3$ | (1) | Beige powder M abt. 160° C. |
| | | | (2) | 1% aqueous solution as hydrochloride |
| 31 | | —NH—(CH$_2$)$_2$—N | (1) | Yellow powder M = 183° C. |
| | | | (2) | 1% aqueous solution as hydrochloride |
| 32 | | —NH(CH$_2$)$_3$—N | (1) | Yellow powder M = 170° C. |
| | | | (2) | 1% aqueous solution |
| 33 | | —NH(CH$_2$)$_2$—N | (1) | Yellow powder M = 162° C. |
| | | | (2) | 1% aqueous solution as hydrochloride |
| 34 | | —NH(CH$_2$)$_2$—N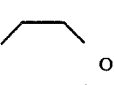O | (1) | Beige powder M abt. 172° C. |
| | | | (2) | 1% aqueous solution as hydrochloride |

-continued

| Reference example | Y | R₄ | (1) Melting point (2) Solubility |
|---|---|---|---|
| 35 | | —NH—CH₂—[pyrrolidine with N-CH₂CH₃] | (1) Beige powder M abt. 160° C. (2) 1% aqueous solution as hydrochloride |
| 36 | | —NH—[piperidine with N-CH₃] | (1) Beige powder M = 177° C. (2) 1% aqueous solution as hydrochloride |
| 37 | H | —NH—[piperazine]—N—CH₃ | (1) Beige powder M abt. 195° C. (2) 5% aqueous solution as hydrochloride |
| 38 | —N(CH₃)₂ | —NH(CH₂)₂—N[homopiperazine]N—CH₃ | (1) Yellow powder M = 150° C. (2) 10% aqueous solution as hydrochloride |
| 39 | —N(CH₃)₂ | —NH—(CH₂)₂—[imidazole ring with N, NH] | (1) Yellow powder M = 138° C. (2) 10% aqueous solution as hydrochloride |

Reference Example 40

2-Dimethylaminoethanethiol (2.1 g) is added to a solution of 5δ-dimethylaminomethylenepristinamycin I$_A$ (1.84 g) in acetic acid (40 cc). The solution obtained is stirred at a temperature of about 20° C. for 20 hours and is then poured slowly into a saturated aqueous solution of sodium bicarbonate; the mixture obtained is extracted 3 times with methylene chloride (400 cc in total). The organic phases are combined, dried over magnesium sulphate, filtered, and concentrated to dryness under reduced pressure (2.7 kPa) at 30° C. The residue obtained is purified by "flash" chromatography [eluent: chloroform-methanol (96-4 by volume)]; fractions 5 and 6 are combined and concentrated to dryness under reduced pressure (2.7 kPa) at 30° C. In this manner, 5δ-(2-dimethylaminoethyl)thiomethylenepristinamycin I$_A$ (0.8 g) is obtained in the form of a yellow powder melting at about 150° C.

NMR spectrum: 0.68 (dd, 1H: 5β₂), 2.32 (s, 6H×0.85: —CH₂N(C$\underline{H}$₃)₂ 1st isomer), 2.35 (s, 6H×0.15: —CH₂N(C$\underline{H}$₂ 2nd isomer), 2.45 (d, 1H: 5β₁), 2.65 (mt, 2H: —SC$\underline{H_2}$—), 3.05 (t, 2H: —CH₂N<), 3.43 (dd, 1H: 5ε₂), 5.15 (in unresolved bands: 5ε₁), 7.60 (broad s, 1H: =CHS—), 7.83 (mt, 1H: 1'H₆, two isomers).

An aqueous solution at a concentration of 1% of 5δ-(2-dimethylaminoethyl)thiomethylenepristinamycin I$_A$ (product AX), in the form of hydrochloride, is obtained with:

| product AX | 0.1 g |
|---|---|
| 0.1 N hydrochloric acid | 1 cc |
| distilled water q.s. | 10 cc |

By using the method of reference Example 40, the following synergistins of general formula (V) which can be combined with the products according to the invention, are prepared.

[The symbols =====, X and Z are defined as in (2b) for the general formula (V), and, unless mentioned otherwise, Y denotes a dimethylamino radical].

| Reference example | Y | R₄ | (1) Melting point (2) Solubility |
|---|---|---|---|
| 41 | —N(CH₃)₂ | —S—(CH₂)₂N(C₂H₅)₂ | (1) Beige powder M abt. 192° C. (2) 1% aqueous solution as hydrochloride |
| 42 | —N(CH₃)₂ | —S—(CH₂)₃N(CH₃)₂ | (1) Beige powder M abt. 170° C. (2) 1% aqueous solution as hydrochloride |
| 43 | —H | —S(CH₂)₃N(CH₃)₂ | (1) Beige powder M abt. 140° C. (2) 10% aqueous solution as hydrochloride |

| Reference example | Y | R₄ | (1) Melting point (2) Solubility |
|---|---|---|---|
| 44 | —N(CH₃)₂ | —S—CH₂—CH(CH₃)—CH₂N(CH₃)₂ | (1) Beige powder M = 234° C. (2) 10% aqueous solution as hydrochloride |
| 45 | —N(CH₃)₂ | —S—CH₂—C(CH₃)₂—N(CH₃)₂ | (1) Beige powder M abt. 200° C. (2) 1% aqueous solution as hydrochloride |
| 46 | —N(CH₃)₂ | —S(CH₂)₂—N⟨pyrrolidine⟩ | (1) Beige powder M abt. 180° C. (2) 1% aqueous solution as hydrochloride |
| 47 | | —S—(CH₂)₂—(N-methylpyrrolidinyl) | (1) Beige powder M abt. 215° C. (2) 0.6% aqueous solution as hydrochloride |
| 48 | | —S—(N-methylpiperidinyl) | (1) Yellow powder M abt. 170° C. (2) 1% aqueous solution as hydrochloride |
| 49 | | —S—(N-ethylpiperidinyl) | (1) Beige powder M abt. 175° C. (2) 1% aqueous solution as hydrochloride |
| 50 | | —S—(CH₂)₂N(CH₃)—(CH₂)₂N(CH₃)₂ | (1) Yellow powder M abt. 160° C. (2) 1% aqueous solution |
| 51 | | —S—CH[CH₂N(CH₃)₂]₂ | (1) Beige powder M abt. 190° C. (2) 1% aqueous solution as hydrochloride |
| 52 | | —S(CH₂)₂—N(N'-methylpiperazinyl) | (1) Beige powder M abt. 170° C. (2) 1% aqueous solution as hydrochloride |
| 53 | | —S(CH₂)₃—N(N'-methylpiperazinyl) | (1) Beige powder M abt. 190° C. (2) 10% aqueous solution as hydrochloride |
| 54 | | —S—CH₂—CH(CH₃)—CH₂—N(CH₃)₃⁺ | (1) Ochre powder M abt. 150° C. (2) 1% aqueous solution as hydrochloride |
| 55 | | —S(CH₂)₂SO₃H | (1) Yellow powder M > 280° C. (2) 5% aqueous solution |

Reference Example 56

A solution of 5δ-(4-methylphenyl)sulphonyloxymethylenepristinamycin I$_A$ (5.2 g) in methylene chloride (50 cc) is added to a solution of 1-(2-mercaptopropyl)-4-methylpiperazine (0.87 g) in ethanol (50 cc), to which sodium ethoxide (0.34 g) has been added. The reaction mixture is stirred at a temperature of about 20° C. for 16 hours and is then diluted with methylene chloride (500 cc) and distilled water (100 cc). After stirring, the aqueous phase is extracted twice with methylene chloride (50 cc in total). The organic phases are combined, dried over magnesium sulphate, filtered, and then concentrated to dryness under reduced pressure (2.7 pKa) at 30° C. The residue is purified by "flash" chromatography [eluent: chloroform-methanol (97.5-2.5 by volume)]. Fractions 33 to 80 are combined and concentrated to dryness under reduced pressure (2.7 kPa) at 30° C. In this manner, 5δ-[3-(4-methyl-1-piperazinyl)-2-propyl]thiomethylenepristinamycin $I_A$ (1.25 g) is obtained in the form of a beige powder melting at about 195° C.

NMR spectrum:

0.70 (dd, 1H: 5$\beta_2$)

1.25 (d, 3H: —C$\underline{H}$—C$\underline{H}_3$)

2.30 (s, 3H: \N—C$\underline{H}_3$)

2.50 (m, 10H: —C$\underline{H}_2$—N⟨C$\underline{H}_2$C$\underline{H}_2$ / C$\underline{H}_2$C$\underline{H}_2$⟩N—CH$_3$)

3.40 (dd, 1H: 5$\epsilon_2$)
7.85 (broad dd, 1H: 1'H$_6$)

An aqueous solution at a concentration of 10% of 5δ-[3-(4-methyl-1-piperazinyl)-2-propyl]thiomethylenepristinamycin $I_A$ (product AAN) in the form of hydrochloride is obtained with:

| product AAN | 0.03 g |
|---|---|
| 0.1 N hydrochloric acid | 0.3 cc |

1-(2-Mercaptopropyl)-4-methylpiperazine is prepared by heating a mixture of propylene sulphide (19 cc) and N-methylpiperazine (29 cc) at 100° C. for 16 hours. In this manner, a colourless oil (32 g) which distils at 105° C. at 1.3 kPa is obtained.

5δ-(4-Methylphenyl)sulphonyloxymethylenepristinamycin $I_A$ can be obtained as follows:

Triethylamine (0.42 cc), and then p-toluenesulphonyl chloride (0.57 g) are added to a solution of 5δ-hydroxymethylenepristinamycin $I_A$ (2.7 g) in methylene chloride (30 cc), at a temperature of about −30° C. The reaction mixture is then stirred at a temperature of about 20° C. for 2 hours and is then concentrated to dryness under reduced pressure (2.7 kPa) at 30° C.; the residue obtained is purified by "flash" chromatography [eluent: methylene chloride-methanol (96-4 by volume)]. After concentrating fractions 4 to 6 to dryness under reduced pressure (2.7 kPa) at 30° C., 5δ-(4-methylphenyl)sulphonyloxymethylenepristinamycin $I_A$ (2.2 g) is obtained in the form of a white powder melting at about 265° C.

NMR spectrum:

0.50 (dd, 1H: 5$\beta_2$)

2.35 (s, 3H: —SO$_2$—⟨C$_6$H$_4$⟩—CH$_3$)

3.30 (dd, 1H: 5$\epsilon_2$)

-continued 5.25 (d, 1H: 5α)
5.30 (dd, 1H: 5$\epsilon_1$)
7.35 to 7.90 (AB system + m, 8H: 4δ + 4ε +

—SO$_2$—⟨C$_6$H$_4$⟩—CH$_3$)

7.85 (dd, 1H: 1'H$_6$)

5δ-Hydroxymethylenepristinamycin $I_A$ can be prepared as follows:

5δ-Dimethylaminomethylenepristinamycin $I_A$ (10.6 g) is added to a 0.1N aqueous solution (420 cc) of hydrochloric acid. The solution obtained is then stirred at a temperature of about 20° C. for 3 hours. A saturated aqueous solution (30 cc) of sodium bicarbonate is then added dropwise so as to produce a pH of about 4. The product which precipitates is separated off by filtration and is then washed 3 times with distilled water (30 cc in total). After drying under reduced pressure (2.7 kPa) at a temperature of about 20° C., 5δ-hydroxymethylenepristinamycin $I_A$ (9.5 g) is obtained in the form of a beige powder. This product is of adequate quality to be used as such in the subsequent steps. It can, however, be purified as follows:

Crude 5δ-hydroxymethylenepristinamycin $I_A$ (9.5 g) is dissolved in ethyl acetate (50 cc); the solution obtained is poured onto silica gel (100 g) contained in a column 2.8 cm in diameter. Ethyl acetate (400 cc) is used for the initial elution, and the corresponding eluate is discarded; elution is then continued with ethyl acetate (1600 cc), and the corresponding eluate is concentrated to dryness under reduced pressure (2.7 kPa) at 30° C. In this manner 5δ-hydroxymethylenepristinamycin $I_A$ (6.3 g) is obtained in the form of white crystals melting at 220° C.

NMR spectrum: 0.69 (dd, 1H: 5$\beta_2$), 2.43 (d, 1H: 5$\beta_1$), 3.40 (d, 1H: 5$\epsilon_2$), 4.0 to 4.2 (m, 3H: 4α+5$\epsilon_1$+5α), 8.15 (s, 1H: =C$\underline{H}$—OH), 11.63 (broad s, 1H: =CH—O$\underline{H}$).

Reference Example 57

By using a method similar to that described in Reference Example 56, 5δ-(3-dimethylamino-2-propyl)thiomethylenepristinamycin $I_A$ (1 g) is obtained in the form of a yellow powder melting at 172° C.

An aqueous solution at a concentration of 5% of 5ε-(3-dimethylamino-2-propyl)thiomethylenepristinamycin $I_A$, in the form of hydroxychloride, is obtained.

Reference Example 58

By using a method similar to that described in Reference Example 56, 5δ-(5-diethylamino-2-pentyl)thiomethylenepristinamycin $I_A$ (1.32 g) is obtained in the form of a beige powder melting at about 185° C.

An aqueous solution at a concentration of 10% of 5δ-(5-diethylamino-2-pentyl)thiomethylenepristinamycin $I_A$ in the form of hydrochloride, is obtained.

Reference Example 59

A solution of 5δ-[(4-methylphenyl)sulphonyloxymethylene]pristinamycin $I_A$ (7.6 g) in tetrahydrofuran (60 cc) is cooled to a temperature of about −10° C. While maintaining this temperature, a solution is added to it, consisting of 2-dimethylaminoethanol (0.65 g) in tetrahydrofuran (60 cc), to which a 50% strength dispersion (0.35 g) of sodium hydride in mineral oil has been added. When the addition is complete, the temperature is allowed to rise slowly to about 20° C. The reaction mixture is stirred at this temperature for 24 hours and is then diluted with methylene chloride (500 cc) and washed with a saturated solution of ammonium chloride (2×50 cc). The organic phase is dried over magnesium sulphate, filtered, and then concentrated to dryness under reduced pressure (2.7 kPa) at 40° C. The residue obtained is purified by "flash" chromatography [eluent: chloroformmethanol (95-5 by volume)]. Fractions 12 to 17 are combined and concentrated to dryness under reduced pressure (2.7 kPa) at 25° C. In this manner, 5δ-(2-dimethylaminoethoxymethylene)pristinamycin $I_A$ (1.5 g) is obtained in the form of a beige powder melting at about 160° C.

NMR spectrum:

0.65 (dd, 1H: $5\beta_2$), 2.3 (s, 6H: —N(CH$_3$)$_2$), 2.65 (m, 2H: —CH$_2$N<), 3.42 (dd, 1H: $5\epsilon_2$), 4.15 (t, 2H: —OCH$_2$—), 5.15 (d, 1H: $5\epsilon_1$), 7.45 (under the aromatics, 1H: >C=CHO), 7.80 (dd, 1H: $1'H_6$).

An aqueous solution at a concentration of 1% of 5δ-(2-dimethylaminoethoxymethylene)pristinamycin $I_A$ (product AAQ), in the form of hydrochloride, is obtained with:

| product AAQ | 0.03 g |
|---|---|
| 0.1 N hydrochloric acid | 0.3 cc |
| distilled water q.s. | 3 cc |

The present invention also relates to the medications consisting of a product of general formula (I) in free form or preferably in the form of a salt of addition with a pharmaceutically acceptable acid in the form of a combination with known synergistins or preferably with synergistins of general formula (V), the combination being moreover capable of containing any other pharmaceutically compatible, inert or physiologically active, product. The medications according to the invention can be administered by parenteral, oral, rectal or topical route.

Sterile compositions for parenteral administration can be, preferably, aqueous or nonaqueous solutions, suspensions or emulsions. Water, propylene glycol, a poly(ethylene glycol), vegetable oils, especially olive oil, injectable organic esters, for example ethyl oleate, or other suitable organic solvents, can be used as a solvent or vehicle. These compositions can also contain adjuvants, especially wetting agents, isotonizing agents, emulsifiers, dispersants and stabilizers. Sterilization can be carried out in various ways, for example by an aspecticizing filtration, by adding sterilizing agents to the composition, by irradiation or by heating. They can also be prepared in the form of sterile solid compositions which can be dissolved in an injectable sterile medium at the time of use.

Tablets, pills, powders or granules can be employed as solid compositions for oral administration. In these compositions, the active product according to the invention (optionally combined with another pharmaceutically compatible product) is mixed with one or more inert diluents or adjuvants such as sucrose, lactose or starch. These compositions can also comprise substances over than diluents, for example a lubricant such as magnesium stearate.

Pharmaceutically acceptable emulsions, solutions, suspensions, syrups and elixirs containing inert diluents such as water or paraffin oil can be used as liquid compositions for oral administration. These compositions can also comprise substances other than the diluents, for example wetting agents, sweeteners or flavourings.

Compositions for rectal administration are suppositories or rectal capsules which contain, in addition to the active substance, excipients such as cocoa butter, semi-synthetic glycerides or poly(ethylene glycols).

Compositions for topical administration can be, for example, creams, salves, lotions, eye lotions, mouth washes, nasal drops or aerosols.

In human therapy, the products according to the invention, which are combined with known synergistins or preferably with synergistins of general formula (V), are especially useful in the treatment of infections of a microbial origin. The dosages depend on the required effect and on the duration of treatment; for an adult, they are generally between 500 and 2000 mg per day by parenteral route, especially by an intravenous route such as a slow perfusion, the dosage of synergistin of general formula (V) itself being between 500 and 2000 mg per day.

As a general rule, the practitioner will determine the dosage which he or she considers the most suitable, depending on the age, weight and all the other individual characteristics of the subject to be treated.

The following example, given without implying any limitation, illustrates the compositions according to the invention.

EXAMPLE

An injectable solution for perfusion, containing 1 g/l of active mixture having the following composition is prepared:

| 26-(2-diethylaminoethyl)sulphinyl-pristinamycin $II_B$ | 0.6 g |
|---|---|
| 5δ-[2-(4-methyl-1-piperazinyl)ethyl]-thiomethylpristinamycin $I_A$ | 0.4 g |
| 0.1 N aqueous solution of hydrochloric acid | 12.7 cc |
| distilled water q.s. | 1000 cc |

We claim:
1. A pristinamycin $II_B$ of the formula:

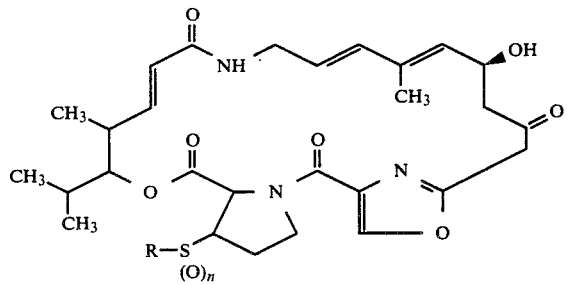

in which R denotes
ether a 3-azetidinyl, 3-pyrrolidinyl, 3- or 4-piperidinyl or 3- or 4-azepinyl radical each of which is unsubstituted or substituted by alkyl,
or alkyl of 2 to 4 carbon atoms substituted by 1 or 2 radicals chosen from phenyl, cycloalkylamino of 3 to 6 ring atoms, N-alkyl-N-cycloalkylamino of 3 to 6 ring atoms, alkylamino, dialkylamino, and dialkylcarbamoyloxy, the alkyl moieties of the said dialkylamino and dialkylcarbamoyloxy radicals being unjoined or joined to form, with the nitrogen atom to which they are attached, and, if required, an oxygen, sulphur, or other nitrogen atom, a 1-azetidinyl, 1-pyrrolidinyl, piperidino, 1-azepinyl, morpholino, thiomorpholino in the form of sulphoxide or sulphone, 1-piperazinyl, 4-alkyl-1-piperazinyl, N-alkyl-1-homopiperazinyl or imidazolyl radical, all of which may be unsubstituted or substituted by alkyl, or R denotes an alkyl of 2 to 4 carbon atoms substituted by 2- or 3-azetidinyl, 2- or 3-pyrroliidinyl, 2-, 3- or 4-piperidyl, 2- 3- or 4-azepinyl, piperazinyl, 4-alkyl-piperazinyl, quinolyl, isoquinolyl, or imidazolyl radical, each of which is unsubstituted or substituted by alkyl, these heterocyclic rings being linked to the alkyl of 2 to 4 carbon atoms by a carbon atom of the ring, n is 1 or 2 and, unless stated otherwise, the abovementioned alkyl radicals are linear or branched and contain 1 to 10 carbon atoms each, in its isomeric forms or their mixtures, or a pharmaceutically acceptable acid addition salt thereof.

2. A pristinamycin $II_B$ according to claim 1, wherein R denotes alkyl of 2 to 4 carbon atoms substituted by 1 or 2 radicals chosen from phenyl, cycloalkylamino of 5 or 6 ring atoms, N-alkyl-N-cycloalkylamino of 5 or 6 ring atoms, alkylamino of 1 to 4 carbon atoms, or dialkylamino in which each alkyl is of 1 to 3 carbon atoms or the alkyls form, with the nitrogen atom to which they are attached, a 1-azetidinyl, 1-pyrrolidinyl, piperidino, or 1-azepinyl radical, or R denotes a 3-azetidinyl, 3-pyrrolidinyl, 3- or 4-piperidyl or 3- or 4-azepinyl radical each of which is unsubstituted or substituted by alkyl of 1 to 4 carbon atoms, at least one of the substituents carried by the said alkyl being in a 1- or a 2-position, in its isomeric forms and their mixtures, or a pharmaceutically acceptable acid addition salt thereof.

3. A pristinamycin $II_B$ according to claim 1 which is 26-(2-diethylamino-1-methylethyl)sulphinylpristinamycin $II_B$, its isomeric forms and their mixtures, or a pharmaceutically acceptable addition salt thereof.

4. A pristinamycin $II_B$ according to claim 1 which is 26-[(2R)2-dimethylaminobutyl]sulphinylpristinamycin $II_B$, its isomeric forms and their mixtures, or a pharmaceutically acceptable addition salt thereof.

5. A pristinamycin $II_B$ according to claim 1 which is 26-(2-diethylaminopropyl)sulphonylpristinamycin $II_B$, its isomeric forms and their mixtures, or a pharmaceutically acceptable acid addition salt thereof.

6. A pristinamycin $II_B$ according to claim 1 which is 26-(2-diisopropylaminoethyl)sulphonylpristinamycin $II_B$, its isomeric forms and their mixtures, or a pharmaceutically acceptable acid addition salt thereof.

7. A antibacterial or antimicrobial composition which contains a pristinamycin $II_B$ according to claim 1 in combination with a synegistically effective amount of a known synergistin or a soluble synergistin of formula:

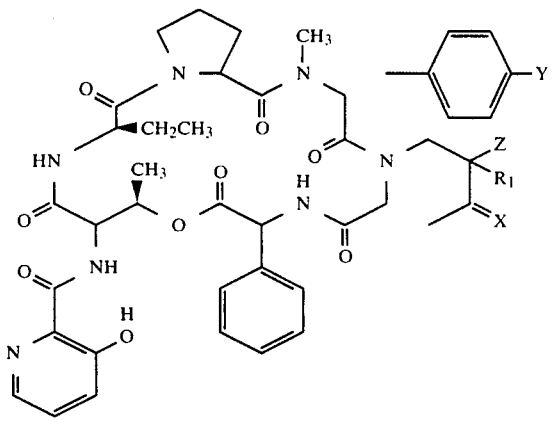

in which Y denotes a hydrogen atom or a dimethylamino radical and
(1) either ⋯ denotes a single bond, Z and $R_1$ denote a hydrogen atom and X denotes a radical of formula:

in which:
either $R_2$ denotes a hydrogen atom and $R_3$ denotes a hydroxy or alkyl radical unsubstituted or substituted by a carboxy, alkyloxycarbonyl, hydroxy, alkylamino or dialkylamino radical whose alkyl radicals can form, with the nitrogen atom to which they are attached, a 4 to 7-member heterocyclic ring chosen from azetidinyl, pyrrolidinyl, piperidinyl, piperazinyl, N-alkylpiperazinyl and azepinyl, or $R_3$ denotes a cycloalkyl radical containing 3 to 7 carbon atoms or a saturated 4 to 7-membered heterocyclic ring chosen from the azetidine, pyrrolidine, piperidine and azepine rings, these heterocyclic rings being unsubstituted or substituted by an alkyl radical on the nitrogen atom, $R_2$ denotes a formyl or alkylcarbonyl radical and $R_3$ denotes an alkyl radical substituted by a carboxy, alkylamino or dialkylamino radical whose alkyl radicals can form, with the nitrogen atom to which they are attached, a 4 to 7-membered heterocyclic ring chosen from azetidinyl, pyrrolidinyl, piperidinyl, piperazinyl, N-alkylpiperazinyl and azepinyl, or $R_3$ denotes a 4 to 7-membered heterocyclic ring chosen from azetidine, pyrrolidine, piperidine and azepine, these heterocyclic rings being unsubstituted or substituted by an alkyl radical on the nitrogen atom, or $R_2$ and $R_3$, which are identical or different, each denote an alkyl radical which is unsubstituted or substituted by carboxy, alkyloxycarbonyl, hydroxy, alkylamino or dialkylamino whose alkyl radicals optionally form, with the nitrogen atom to which they are attached, a 4 to 7-membered heterocyclic ring chosen from azetidinyl, pyrrolidinyl, piperidinyl, piperazinyl, N-alkylpiperazinyl and azepinyl-or $R_2$ and $R_3$ form, together with the nitrogen atom to which they are attached, a 4 to 7-membered heterocyclic ring chosen from the azetidine, pyrrolidine, piperidine, morpholine and piperazine rings, optionally substituted by an alkyl radical, (2) or $====$ denotes a double bond, X denotes an oxygen atom and Z denotes a radical of formula:

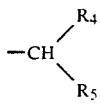

in which:

(a) either $R_1$ and $R_5$ each denote a hydrogen atom and $R_4$ denotes a 3-pyrrolidinylthio or 3- or 4-piperidylthio radical (these radicals being optionally substituted by an alkyl radical) or $R_4$ denotes an alkylthio radical substituted by one or two hydroxysulphonyl, alkylamino or dialkylamino (optionally substituted by a mercapto or dialkylamino radical) radicals or by one or two rings chosen from piperazino (optionally substituted by an alkyl or mercaptoalkyl radical), morpholino, thiomorpholino, piperidino, 1-pyrrolidinyl, 2, 3 or 4-piperidyl and 2- or 3-pyrrolidinyl (these last two rings being optionally substituted by an alkyl radical on the nitrogen atom), (b) or $R_1$ and $R_5$ together form a valency bond and $R_4$ denotes a 3-pyrrolidinylamino, 3- or 4-piperidylamino, 3-pyrrolidinyloxy, 3- or 4-piperidyloxy, 3-pyrrolidinylthio, 3- or 4-piperidylthio radical (these radicals being optionally substituted by an alkyl radical on the nitrogen atom in the ring), or $R_4$ denotes an alkylamino, alkyloxy or alkylthio radical substituted by one or two hydroxy-sulphonyl, alkylamino, dialkylamino (optionally substituted by a dialkylamino radical), trialkylammonio or 4- or 5-imidazolyl radicals, or by one or two rings chosen from piperazino (optionally substituted by an alkyl or mercaptoalkyl radical), morpholino, thiomorpholino, piperidino, 1-pyrrolidinyl, 2, 3 or 4-piperidyl and 2- or 3-pyrrolidinyl (these two latter rings being optionally substituted by an alkyl radical on the nitrogen atom), it being understood that the alkyl radicals and alkyl moieties referred to in the symbols defined above contain 1 to 5 carbon atoms and form a linear or branched chain, if appropriate in the form of one of its isomers or their mixtures, and optionally in the form of an acid addition salt, a metal salt or an addition salt with a nitrogen-containing organic base.

8. A pharmaceutical composition according to claim 7 which also contains a compatible pharmaceutically acceptable carrier and/or adjuvant.

9. A pharmaceutical composition comprising an effective amount of a pristinamycin $II_B$ according to claim 1 in association with a compatible pharmaceutically acceptable carrier and/or adjuvant.

10. Method of controlling bacterial growth which comprises exposing said bacteria to the effect of a pristinamycin $II_B$ according to claim 1 in sufficient concentration to control said bacteria.

* * * * *

UNITED STATES PATENT AND TRADEMARK OFFICE
CERTIFICATE OF CORRECTION

PATENT NO.: 4,668,669

DATED: May 26, 1987

INVENTOR(S): Jean-Claude Barriere et al.

It is certified that an error appears in the above-identified patent and that said Letters Patent is hereby corrected as shown below:

On the Title Page, second column, delete the second formula and substitute:

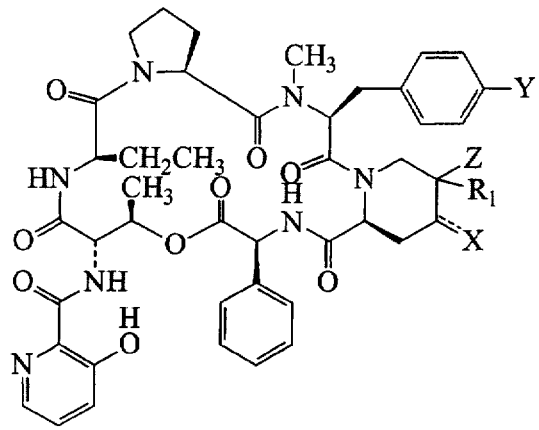

UNITED STATES PATENT AND TRADEMARK OFFICE
CERTIFICATE OF CORRECTION

PATENT NO.: 4,668,669

DATED: May 26, 1987

INVENTOR(S): Jean-Claude Barriere et al.

It is certified that an error appears in the above-identified patent and that said Letters Patent is hereby corrected as shown below:

Column 13, lines 1-18, delete Formula (V) and substitute:

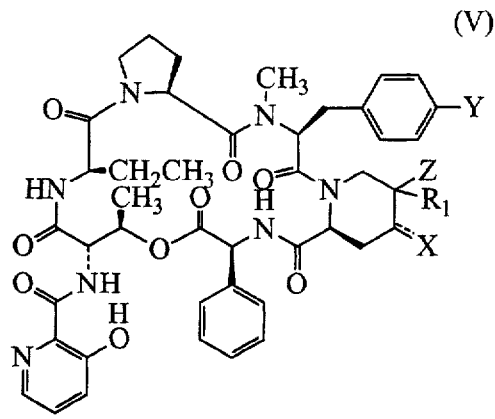

UNITED STATES PATENT AND TRADEMARK OFFICE
CERTIFICATE OF CORRECTION

PATENT NO.: 4,668,669

DATED: May 26, 1987

INVENTOR(S): Jean-Claude Barriere et al.

It is certified that an error appears in the above-identified patent and that said Letters Patent is hereby corrected as shown below:

Column 15, lines 1-18, delete Formula (IX) and substitute:

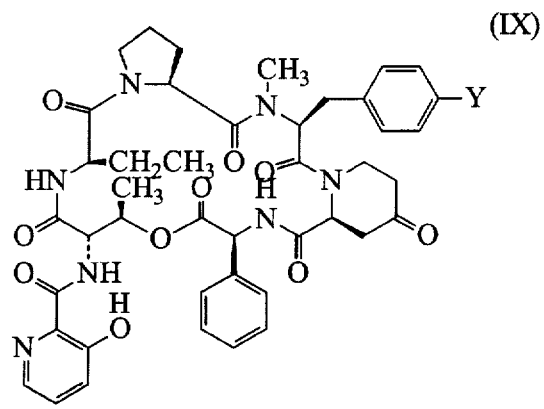

UNITED STATES PATENT AND TRADEMARK OFFICE
CERTIFICATE OF CORRECTION

PATENT NO.: 4,668,669            Page 4 of 10

DATED: May 26, 1987

INVENTOR(S): Jean-Claude Barriere et al.

It is certified that an error appears in the above-identified patent and that said Letters Patent is hereby corrected as shown below:

Column 16, lines 1-18, delete Formula (XI) and substitute:

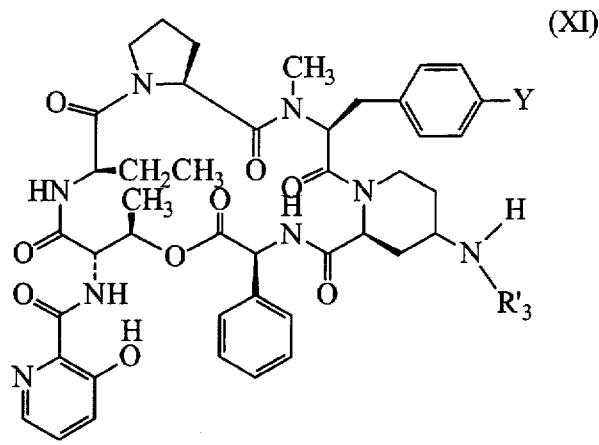

UNITED STATES PATENT AND TRADEMARK OFFICE
CERTIFICATE OF CORRECTION

PATENT NO.: 4,668,669

DATED: May 26, 1987

INVENTOR(S): Jean-Claude Barriere et al.

It is certified that an error appears in the above-identified patent and that said Letters Patent is hereby corrected as shown below:

Column 17, lines 1-18, delete Formula (XIII) and substitute:

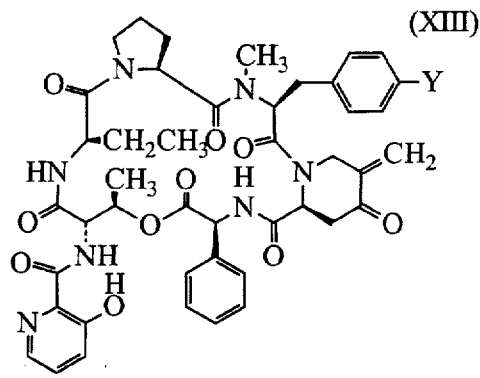

UNITED STATES PATENT AND TRADEMARK OFFICE
CERTIFICATE OF CORRECTION

PATENT NO.: 4,668,669

DATED: May 26, 1987

INVENTOR(S): Jean-Claude Barriere et al.

It is certified that an error appears in the above-identified patent and that said Letters Patent is hereby corrected as shown below:

Column 17, lines 32-48, delete Formula (XIV) and substitute:

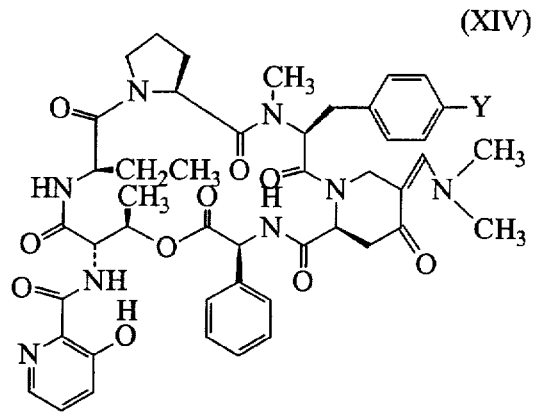

UNITED STATES PATENT AND TRADEMARK OFFICE
CERTIFICATE OF CORRECTION

PATENT NO.: 4,668,669

DATED: May 26, 1987

INVENTOR(S): Jean-Claude Barriere et al.

It is certified that an error appears in the above-identified patent and that said Letters Patent is hereby corrected as shown below:

Column 18, lines 47-62, delete Formula (XVIII) and substitute:

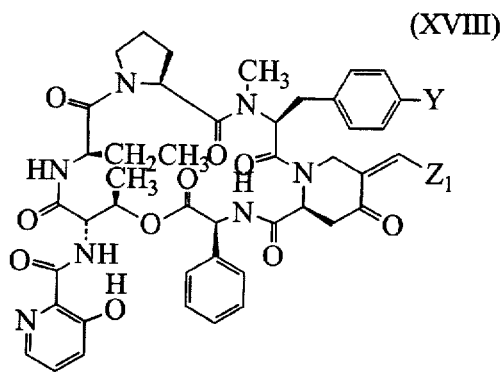

(XVIII)

UNITED STATES PATENT AND TRADEMARK OFFICE
CERTIFICATE OF CORRECTION

PATENT NO.: 4,668,669

DATED: May 26, 1987

INVENTOR(S): Jean-Claude Barriere et al.

It is certified that an error appears in the above-identified patent and that said Letters Patent is hereby corrected as shown below:

Column 23, lines 4-22, delete Formula (XXIII) and substitute:

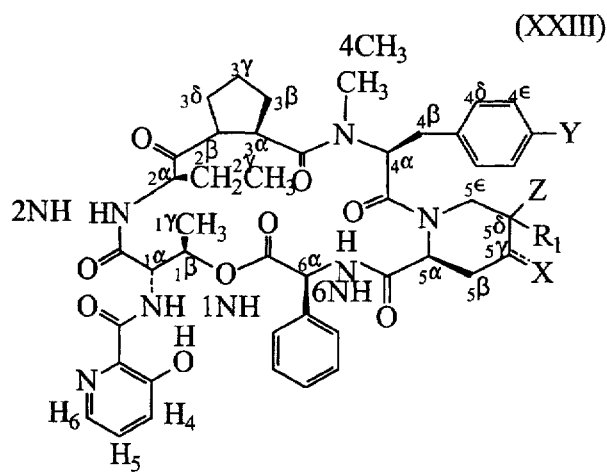

UNITED STATES PATENT AND TRADEMARK OFFICE
CERTIFICATE OF CORRECTION

PATENT NO.: 4,668,669

DATED: May 26, 1987

INVENTOR(S): Jean-Claude Barriere et al.

It is certified that an error appears in the above-identified patent and that said Letters Patent is hereby corrected as shown below:

In claim 5, delete line 2 (col. 85, line 56) and substitute --26(2-diethylaminoethyl) sulphonylpristinamycin $II_B$ --

In claim 7 (col. 86, lines 1-17) delete the formula and substitute:

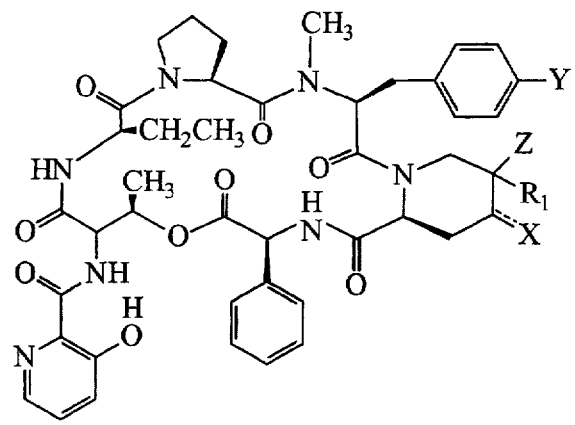

UNITED STATES PATENT AND TRADEMARK OFFICE
CERTIFICATE OF CORRECTION

PATENT NO.: 4,668,669

DATED: May 26, 1987

INVENTOR(S): Jean-Claude Barriere et al.

It is certified that an error appears in the above-identified patent and that said Letters Patent is hereby corrected as shown below:

Claim 7, line 22 (col. 86), after "either" insert -- --- --

Signed and Sealed this

Twenty-fourth Day of October, 2000

Attest:

Q. TODD DICKINSON

*Attesting Officer*     *Director of Patents and Trademarks*

UNITED STATES PATENT AND TRADEMARK OFFICE

(12)        CERTIFICATE EXTENDING PATENT TERM
UNDER 35 U.S.C. § 156

| | | | |
|---|---|---|---|
| (68) | PATENT NO. | : | 4,668,669 |
| (45) | ISSUED | : | May 26, 1987 |
| (75) | INVENTOR | : | Jean-Claude Barriere, et al. |
| (73) | PATENT OWNER | : | Aventis Pharma S.A. |
| (95) | PRODUCT | : | SYNERCID® (quinupristin and dalfopristin) |

This is to certify that an application under 35 U.S.C. § 156 has been filed in the United States Patent and Trademark Office, requesting extension of the term of U.S. Patent No. 4,668,669 based upon the regulatory review of the product SYNERCID® (quinupristin and dalfopristin)(NDA 50-747) by the Food and Drug Administration. Since it appears that the requirements of the law have been met, this certificate extends the term of the patent for the period of

(94)              1,333 days from January 10, 2006, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 7th day of January 2004.

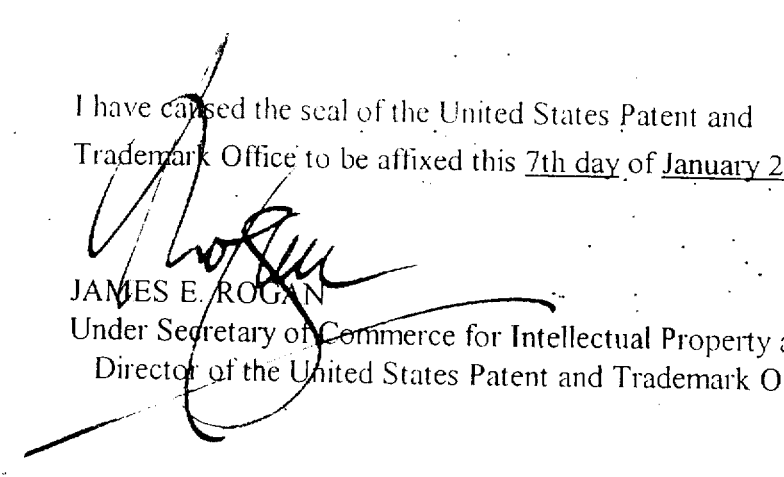

JAMES E. ROGAN
Under Secretary of Commerce for Intellectual Property and
Director of the United States Patent and Trademark Office